US006495656B1

(12) United States Patent
Haile et al.

(10) Patent No.: US 6,495,656 B1
(45) Date of Patent: Dec. 17, 2002

(54) COPOLYESTERS AND FIBROUS MATERIALS FORMED THEREFROM

(75) Inventors: William A. Haile; Leron R. Dean; Richard L. McConnell; Mark E. Tincher; Alan W. White; Charles M. Buchanan, all of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/570,456

(22) Filed: May 12, 2000

Related U.S. Application Data

(63) Continuation of application No. 09/121,212, filed on Jul. 23, 1998, which is a division of application No. 08/763,562, filed on Dec. 10, 1996, now Pat. No. 5,900,322, which is a continuation of application No. 08/427,944, filed on Apr. 26, 1995, now Pat. No. 5,599,858, which is a division of application No. 08/163,441, filed on Dec. 7, 1993, now Pat. No. 5,446,079, which is a division of application No. 07/797,512, filed on Nov. 21, 1991, now Pat. No. 5,292,783, which is a continuation-in-part of application No. 07/736,262, filed on Jul. 23, 1991, now abandoned, which is a continuation-in-part of application No. 07/620,225, filed on Nov. 30, 1990, now abandoned.

(51) Int. Cl.[7] .............................................. C08G 63/02
(52) U.S. Cl. .................................................... 528/272
(58) Field of Search ............................................ 521/41

(56) References Cited

U.S. PATENT DOCUMENTS

| | | | |
|---|---|---|---|
| 2,901,466 A | 8/1959 | Kibler et al. ................ 260/75 |
| 3,589,956 A | 6/1971 | Kranz et al. ............... 156/62.4 |
| 3,907,754 A | 9/1975 | Tershansy et al. ............ 260/75 |
| 3,962,189 A | 6/1976 | Russin et al. ............. 260/75 R |
| 4,010,145 A | 3/1977 | Russin et al. ............. 260/75 R |
| 4,081,428 A | 3/1978 | Thompson .................... 260/75 |
| 4,093,603 A | 6/1978 | Jackson, Jr. et al. ...... 260/75 R |
| 4,094,721 A | 6/1978 | Sturm et al. ................. 156/309 |
| 4,116,942 A | 9/1978 | Weinberg et al. ........... 528/283 |
| 4,189,338 A | 2/1980 | Ejima et al. ................. 156/167 |
| 4,217,426 A | 8/1980 | McConnell et al. ......... 525/173 |
| 4,340,526 A | 7/1982 | Petke et al. .................. 524/292 |
| 4,356,299 A | 10/1982 | Cholod et al. .............. 528/279 |
| 4,419,507 A | 12/1983 | Sublett ....................... 528/302 |
| 4,450,250 A | 5/1984 | McConnell et al. ......... 524/141 |
| 4,468,490 A | 8/1984 | Meyer, Jr. et al. .......... 524/311 |
| 4,521,556 A | 6/1985 | Adams ......................... 524/88 |
| 4,540,749 A | 9/1985 | Meyer, Jr. et al. .......... 525/437 |
| 4,576,977 A | 3/1986 | Miyuazaki et al. ......... 523/137 |
| 4,576,997 A | 3/1986 | Trotter et al. ............... 525/444 |
| 4,668,453 A | 5/1987 | Ebnesajjad et al. ........... 264/78 |

(List continued on next page.)

FOREIGN PATENT DOCUMENTS

| | | | |
|---|---|---|---|
| DE | 28 47 533 | 5/1980 | |
| DE | 197 15 682 A1 | 10/1997 | |
| EP | 0 036 062 | 9/1981 | |
| EP | 0 517 171 A2 | 12/1992 | |
| EP | 0 526 645 A1 | 2/1993 | |
| EP | 532 988 A1 | 3/1993 | |
| EP | 542 239 A1 | 5/1993 | |
| EP | 11032596 | 9/1999 | .......... A01G/13/02 |
| FR | 2 138 728 | 1/1973 | |
| FR | 2 279 784 | 2/1976 | |
| GB | 1 029 136 | 5/1962 | |
| GB | 977 104 | 12/1964 | |
| GB | 1047072 | 11/1966 | ........... C08G/17/08 |
| GB | 1053374 | 12/1966 | |
| GB | 1344492 | 1/1974 | ............. D01F/7/04 |
| GB | 2 089 824 | 6/1982 | |
| JP | 51-148793 | 12/1976 | |
| JP | 53-147815 | 12/1978 | |
| JP | 57-101018 | 6/1982 | |
| JP | 57-133217 | 8/1982 | |
| JP | 58-8121 | 1/1983 | |
| JP | 59-1715 | 1/1984 | |
| JP | 63-112723 | 5/1988 | |
| JP | 63-175119 | 7/1988 | |
| JP | 63-182414 | 7/1988 | |

(List continued on next page.)

OTHER PUBLICATIONS

Negi, Yuvraj S.et al., "Structure–Property Relationship in Copolyesters. I. Preparation and Characterization of Ethylene Terephthalate–Hexamethylene Terephthalate Copolymers," Journal of Applied Polymer Science, 28, pp. 2291–2302 (1983).

"Chemical Substances of Melty," Unitika Ltd., Product Brochure, Apr. 1993.

"Types of Bellcombi," Kanebo Ltd., Product Brochure.

"Textile Fibers Group Hoechst Celanese Corporation," Hoechst Celanese, Product Brochure.

"Improved Color Poly(ethylene/1,4–cyclohexylenedimethylene terephthalate)," Research Disclosure, No. 359, Mar. 1994, pp. 142–144.

R. Bass, "PCT and PETG Polyester Fibers for Nonwovens," INDA–TEC 96, Nonwovens Conference, 1996, pp. 19.1–19.9.

International Search Report, dated Apr. 8, 1999, in International Application No. PCT/US98/23599.

International Search Report, dated Feb. 2, 1999, in International Application No. PCT/US98/17813.

International Search Report, dated Nov. 29, 1999, in PCT/US99/17828.

International Search Report, dated Nov. 29, 1999, in PCT/US99/17830.

Primary Examiner—Terressa M. Boykin
(74) Attorney, Agent, or Firm—Bernard J. Graves; Cheryl J. Tubach, Esq.

(57) ABSTRACT

This invention relates to binary blends of cellulose esters and aliphatic-aromatic copolyesters, cellulose esters and aliphatic polyesters as well as ternary blends of cellulose esters and/or aliphatic polyesters and/or aliphatic-aromatic copolyesters and/or polymeric compounds as well as fibers, nonwovens, molded objects, and films prepared therefrom.

11 Claims, 7 Drawing Sheets

U.S. PATENT DOCUMENTS

| | | | | |
|---|---|---|---|---|
| 4,668,764 | A | 5/1987 | Satou | 528/308 |
| 4,740,581 | A | 4/1988 | Pruett et al. | 528/289 |
| 4,745,174 | A | 5/1988 | Pruett et al. | 528/289 |
| 4,749,772 | A | 6/1988 | Weaver et al. | 528/288 |
| 4,749,773 | A | 6/1988 | Weaver et al. | 528/288 |
| 4,749,774 | A | 6/1988 | Weaver et al. | 528/288 |
| RE32,765 | E | 10/1988 | Callander et al. | 524/382 |
| 4,950,732 | A | 8/1990 | Weaver et al. | 528/288 |
| 4,999,388 | A | 3/1991 | Okamoto | 523/400 |
| 5,017,680 | A | 5/1991 | Sublett | 528/274 |
| 5,057,561 | A | 10/1991 | Manica et al. | 524/68 |
| 5,106,944 | A | 4/1992 | Sublett | 528/279 |
| 5,166,311 | A | 11/1992 | Nichols | 528/285 |
| 5,219,941 | A | 6/1993 | Meyer, Jr. et al. | 525/173 |
| 5,252,699 | A | 10/1993 | Chamberlin et al. | 528/289 |
| 5,292,783 | A | 3/1994 | Buchanan et al. | 524/37 |
| 5,312,797 | A | 5/1994 | Takiguchi et al. | 503/227 |
| 5,340,907 | A | 8/1994 | Yau et al. | 528/274 |
| 5,340,910 | A | 8/1994 | Chamberlin et al. | 528/289 |
| 5,348,699 | A | 9/1994 | Meyer et al. | 264/176.1 |
| 5,372,864 | A | 12/1994 | Weaver et al. | 428/36.92 |
| 5,384,377 | A | 1/1995 | Weaver et al. | 525/437 |
| 5,385,773 | A | 1/1995 | Yau et al. | 428/221 |
| 5,393,863 | A | 2/1995 | Yau et al. | 528/308.4 |
| 5,393,871 | A | 2/1995 | Yau et al. | 528/308.4 |
| 5,446,079 | A | 8/1995 | Buchanan et al. | 524/41 |
| 5,453,479 | A | 9/1995 | Borman et al. | 528/279 |
| 5,559,171 | A | 9/1996 | Buchanan et al. | 524/41 |
| 5,563,236 | A | 10/1996 | Murata et al. | 528/295 |
| 5,580,911 | A | 12/1996 | Buchanan et al. | 524/41 |
| 5,599,858 | A | 2/1997 | Buchanan et al. | 524/41 |
| 5,608,031 | A | 3/1997 | Yau et al. | 528/281 |
| 5,643,991 | A | 7/1997 | Stipe et al. | 524/496 |
| 5,656,715 | A | 8/1997 | Dickerson et al. | 528/271 |
| 5,656,716 | A | 8/1997 | Schmidt et al. | 528/279 |
| 5,668,243 | A | 9/1997 | Yau et al. | 528/280 |
| 5,681,918 | A | 10/1997 | Adams et al. | 528/279 |
| 5,688,899 | A | 11/1997 | Strand et al. | 528/279 |
| 5,744,571 | A | 4/1998 | Hilbert et al. | 528/272 |
| 5,773,554 | A | 6/1998 | Dickerson et al. | 528/271 |
| 5,889,135 | A | 3/1999 | Warzelhan et al. | 528/176 |
| 5,900,322 | A | 5/1999 | Buchanan et al. | 428/480 |

FOREIGN PATENT DOCUMENTS

| | | | |
|---|---|---|---|
| JP | 63-203818 | 8/1988 | |
| JP | 63-270812 | 11/1988 | |
| JP | 3-180530 | 8/1991 | |
| JP | 05-005212 | 1/1993 | |
| JP | 5059616 | 3/1993 | |
| JP | 5097985 | 4/1993 | |
| JP | 5-132548 | 5/1993 | |
| JP | 6-2217 | 1/1994 | |
| JP | 8092816 | 4/1996 | |
| JP | 8245778 | 9/1996 | |
| WO | WO 84/02144 | 6/1984 | |
| WO | WO 92/09654 | 6/1992 | C08L/1/14 |
| WO | WO 96/04422 | 2/1996 | |
| WO | WO 96/15173 | 5/1996 | |
| WO | WO 96/15174 | 5/1996 | |
| WO | WO 96/15175 | 5/1996 | |
| WO | WO 96/15176 | 5/1996 | |
| WO | WO 96/25446 | 8/1996 | |
| WO | WO 96/25448 | 8/1996 | |
| WO | WO 96/25466 | 8/1996 | |
| WO | 97/30102 | 8/1997 | |
| WO | WO 98/12245 | 3/1998 | |
| WO | 99/10573 | 3/1999 | |
| WO | 99/24648 | 5/1999 | |
| WO | WO 00/12792 | 3/2000 | D01F/6/84 |

FIG. 6A  FIG. 6B

COPOLYESTERS AND FIBROUS MATERIALS FORMED THEREFROM

PRIORITY DATA

This application is a continuation of U.S. application Ser. No. 09/121,212 filed Jul. 23, 1998 which is a divisional application of Ser. No. 08/763,562, filed Dec. 10, 1996, now U.S. Pat. No. 5,900,322, which is a continuation of Ser. No. 08/427,944, filed Apr. 26, 1995, now U.S. Pat. No. 5,599,858, which is a divisional of application Ser. No. 08/163,441 filed on Dec. 7, 1993 now U.S. Pat. No. 5,446,079, which is a divisional of Ser. No. 07/797,512 filed on Nov. 21, 1991, now U.S. Pat. No. 5,292,783 which issued on Mar. 8, 1994; which is a continuation-in-part of Ser. No. 07/736,262 filed on Jul. 23, 1991, now abandoned; which is a continuation-in-part of Ser. No. 07/620,225 filed on Nov. 30, 1990, now abandoned; the disclosures of which are herein incorporated by reference in their entirety.

FIELD OF THE INVENTION

This invention concerns binary blends of cellulose esters with aliphatic polyesters or aliphatic-aromatic copolyesters as well as ternary blends of cellulose esters with aliphatic polyesters and/or aliphatic-aromatic copolyesters and/or other polymers. These resins are useful as molded or extruded plastic objects, fibers, or films. This invention also concerns random aliphatic-aromatic copolyesters which are useful as molded or extruded plastic objects, fibers, or films. Moreover, various additives can be added to the blends or to the random aliphatic-aromatic copolyesters to enhance properties such as water vapor transmission rates or biodegradability. Additionally, the copolyesters of the invention may be formed into a variety of products, especially fibers, such as binder fibers, for nonwovens, textile/industrial yarns and fabrics, composites, laminates and other molded articles.

BACKGROUND OF THE INVENTION

It is well known that cellulose esters are important as commercial plastics and as fibers. In general, cellulose esters are used in plastic applications where hard but clear plastics are required. For example, cellulose esters are used in tool handles, eyeglass frames, toys, toothbrush handles, and the like. All of these applications require a combination of high melting and glass transition temperatures as well as high modulus and good tensile strength. Formulations based on cellulose esters which provide plastic films with low modulus but good tensile strength while maintaining sufficient melting and glass transition temperatures (Tg) to allow thermal processing are generally unknown. Formulations based on cellulose esters which allow thermal extrusion of fibers are also generally unknown.

Because of the high melt temperatures and low melt stability of many of the cellulose esters, plasticizers such as dioctyl adipate or triphenyl phosphate are often added to the cellulose ester to lower the melt temperatures during melt processing of the polymer. Although this technique is effective, addition of a monomeric plasticizer often creates secondary problems related to volatile or extractable plasticizers such as die drip during melt extrusion or long-term dimensional stability (creep) in an object made from the cellulose ester.

The most basic requirement for polymer-polymer miscibility is that the free energy of mixing be negative ($\Delta G<0$). Although on the surface it would seem that polymer-polymer miscibility would be common, in reality there are only a few known miscible binary blends and even fewer known miscible ternary blend systems (Brannock, G. R.; Paul, D. R., *Macromolecules,* 23, 5240–5250 (1990)). The discovery of miscible binary or ternary blends is very uncommon.

The classical experimental techniques for determiing polymer blend miscibility involve the determination of the optical clarity of a film made from the blend, measurement of the appropriate mechanical properties, and measurement of the glass transition temperature by an appropriate thermal analysis technique such as dynamic mechanical thermal analysis (DMTA) or differential scanning calorimeter (DSC). If a blend is miscible, films made from the blend will generally be clear. Likewise, mechanical properties of a blend, such as tensile strength or tangent modulus, are often intermediate between those of the blend components. Furthermore, a miscible amorphous blend will show a single Tg intermediate between that of the component homopolymers while an immiscible or partially miscible blend will show multiple Tg's. In the case of a completely immiscible blend, the Tg's will be those of the homopolymers. For partially miscible blends, the Tg's will be intermediate values corresponding to partially miscible phases rich in one of the components. The variation in binary blend Tg can be modeled by the Fox-Flory equation, $Tg_{12}=Tg_1(W_1)+Tg_2(W_2)$, where $Tg_{12}$ is the Tg of the blend, $Tg_1$ and $Tg_2$ are the Tg's of homopolymers, and $W_1$ and $W_2$ are the weight percent of each component in the blend. Since the Fox equation does not take into account specific interaction between the blend components the Gordon-Taylor equation, $Tg_{12}=Tg_{1+}[kW_2(Tg_2-Tg_{12})/W_1]$ where k is a constant, is often preferred in blend analysis. For a homogenous, well mixed system, a plot of $Tg_{12}$ versus $W_2(Tg_2-Tg_{12})/W_1$ will yield a straight line the slope of which is equal to k and the ordinate intercept will be equal to $Tg_1$. The constant k is often taken as a measure of secondary interactions between the blend components. When k is equal to one, the Gordon-Taylor equation reduces to a simple weight average of the component Tg's.

Miscible blends of cellulose esters and other polymers are generally unknown. The most notable exceptions include the work disclosed by Koleske, et al. (U.S. Pat. No. 3,781,381 (1973)), Bogan and Combs (U.S. Pat. No. 3,668,157 (1972)), Waniczek et al., (U.S. Pat. No. 4,506,045 (1985)), and Wingler et al. (U.S. Pat. No. 4,533,397 (1985)). Koleske et al. reported that blends, formed by solution casting of polycaprolactone and cellulose ester mixtures, are miscible. Later work by Hubbell and Cooper (*J. Appl. Polym. Sci.,* 1977, 21, 3035) demonstrated that cellulose acetate butyrate/polycaprolactone blends are in fact immiscible. Bogan and Combs have reported that block copolymers of polyether-polyesters form miscible blends with some cellulose esters. Critical to the invention of Bogan and Combs was the use of an elastomeric block copolymer; they report that the corresponding homopolymeric elastomers were incompatible with cellulose esters. Waniczek et al., have disclosed that polyester carbonate and polyether carbonate copolymers form miscible blends with many cellulose esters and are useful as thermoplastic resins. Wingler et al. report that contact lenses can be prepared from blends consisting of (A) 97–70% by weight of one or more cellulose esters and (B) 3–30% by weight of an aliphatic polymeric compound having ester moieties, carbonate moieties, or both ester and carbonate moieties in the same polymer chain. The invention of Wingler et al. is limited to aliphatic polymeric compounds; no reference is made to random copolymers consisting of aliphatic diacids, aromatic diacids, and suitable diols or polyols. The invention of Wingler is further limited to cellulose mixed esters having a weight percent hydroxyl of 1.2% to 1.95% ($DS_{OH}$=0.11–0.19 where "DS" or "DS/AGU" refers to the number of substituents per anhydroglucose unit where the maximum DS/AGU is three). The invention of Wingler et al. is also limited to binary miscible blends and by the composition range of the blends (3–30% aliphatic polymeric compound). No reference is made to blends containing an immiscible component where the immiscible component is useful for enhancing properties such as water vapor transmission rates or biodegradability. Immiscible blends of cellulose esters and aromatic polyesters have also been disclosed by Pollock et al. (U.S. Pat. No. 4,770,931 (1988)) which are useful in applications such as paper substitutes.

One time use, disposable items are common. Examples of such disposable articles include items such as infant diapers, incontinence briefs, sanitary napkins, tampons, bed liners, bedpads, bandages, food bags, agricultural compost sheets, and the like. Examples of other disposable items include razor blade handles, toothbrush handles, disposable syringes, fishing lines, fishing nets, packaging, cups, clamshells, and the like. For disposable items, environmental non-persistence is desirable.

Disposable articles are typified by disposable diapers. A disposable diaper typically has a thin, flexible polyethylene film cover, an absorbent filler as the middle layer, and a porous inner liner which is typically nonwoven polypropylene. The diaper construction also requires tabs or tape for fastening the diaper (typically polypropylene) as well as various elastomers and adhesives. Although the absorbent filler is usually biodegradable or easily dispersed in an aqueous environment, currently neither the outer or inner liner nor the other parts such as the tabs or adhesives will degrade from microbial action. Consequently, disposable absorbent materials such as diapers accumulate in landfills and place enormous pressure on waste systems. Other disposable articles such as plastic bags or plastic compost sheets suffer from similar problems.

Numerous studies have demonstrated that cellulose or cellulose derivatives with a low degree of substitution, i.e., less than one, are biodegradable. Cellulose is degraded in the environment by both anaerobic or aerobic microorganisms. Typical end products of this microbial degradation include cell biomass, methane(anaerobic only), carbon dioxide, water, and other fermentation products. The ultimate end products will depend upon the type of environment as well as the type of microbial population that is present. However, it has been reported that cellulose esters with a DS greater than about one are completely resistant to attack by microorganisms. For example, Stutzenberger and Kahler (*J. Appl. Bacteriology*, 66, 225 (1986)) have reported that cellulose acetate is extremely recalcitrant to attack by *Thermomonospora curvata*.

Polyhydroxyalkanoates (PHA), such as polyhydroxybutyrate (PHB), polycaprolactone (PCL), or copolymers of polyhydroxybutyrate and polyhydroxyvalerate (PHBV), have been known for at least twenty years. With the exception of polycaprolactone, they are generally prepared biologically and have been reported to be biodegradable (M. Kunioka et al., *Appl. Microbiol. Biotechnol.*, 30, 569 (1989)).

Polyesters prepared from aliphatic diacids or the corresponding carboxylic ester of lower alcohols and diols have also been reported to be biodegradable. For example, Fields and Rodriguez ("Proceedings of the Third International Biodegradation Symposium", J. M. Sharpley and A. M. Kaplan, Eds., Applied Science, Barking, England, 1976, p. 775) prepared polyesters from C2–C12 diacids coupled with C4–C12 diols and found that many were biodegradable.

Aliphatic polyesters have been used in very few applications mainly because of their low melting points and low glass transition temperatures (generally less than 65° C. and −30° C., respectively). At room temperature, the physical form of many of the aliphatic polyesters is as a thick, viscous liquid. Therefore, aliphatic polyesters are not expected to be generally useful.

On the other hand, aromatic polyesters, such as poly (ethylene terephthalate), poly(cyclohexanedimethanol terephthalate), poly(ethylene terephthalate-co-isophthalate), and poly(ethylene napthalatate) have proven to be very useful materials. Aromatic polyesters, however, are generally very resistant to biodegradation (J. E. Potts in "Kirk-Othmer Encyclopedia of Chemical Technology", Suppl. Vol, Wiley-Interscience, New York, 1984, pp. 626–668). Block copolyesters containing both aliphatic and aromatic structures have been prepared and have been shown to be biodegradable. Examples of aliphatic-aromatic block copolyester-ethers include the work of Reed and Gilding (*Polymer*, 22,499 (1981)) using poly(ethylene terephthalate)/poly(ethylene oxide) where these block copolymers were studied and found to be biodegradable in vitro. Tokiwa and Suzuki have investigated block copolyesters such as those derived from poly(caprolactone) and poly(butylene terephthalate) and found them to be degraded by a lipase (*J. Appl. Polym. Sci.*, 26, 441–448 (1981)). Presumably, the biodegradation is dependent upon the aliphatic blocks of the copolyesters; the blocks consisting of aromatic polyester are still resistant to biodegradation. Random aliphatic-aromatic copolyesters have not been investigated in this regard.

While random copolyesters with low levels of aliphatic diacids are known (e.g., Droscher and Horlbeck, *Ange. Makromol. Chemie*, 128, 203–213(1984)), copolyesters with high levels (>30%) of aliphatic dicarboxylic components are generally unknown. Copolyesters with as much as 40% aliphatic dicarboxylic acid components have been disclosed in adhesive applications; however, these copolyesters adhesives contain at least two dialcohol components in order to achieve the desired adhesive properties (Cox, A., Meyer, M. F., U.S. Pat. No. 4,966,959 (1990)).

There are many references to the preparation of films from polymers such as polyhydroxybutyrate (PHB). Production of films from PHB generally involves solvent casting principally because PHB polymers tend to remain sticky or tacky for a substantial time after the temperature has dropped below the melting point of the PHB. To circumvent this problem, Martini et al. (U.S. Pat. Nos. 4,826,493 and 4,880,592) teach the practice of co-extruding PHB with a thermoplastic that is non-tacky. Such thermoplastics remain as a permanent layer on the PHB film or may be a sacrificial film which is removed following extrusion.

PHB has also been reported to be useful in the preparation of disposable articles. Potts (U.S. Pat. Nos. 4,372,311 and 4,503,098) has disclosed that water soluble polymers such as poly(ethylene oxide) may be coated with biodegradable water insoluble polymers such as PHB. In these inventions, the PHB layer, which is distinct from the water soluble layer, degrades exposing the water soluble layer which will then disperse in an aqueous environment.

There have been other reports of the preparation of a biodegradable barrier film for use in disposable articles.

Comerford et al. (U.S. Pat. No. 3,952,347) have disclosed that finely divided biodegradable materials such as cellulose, starch, carbohydrates, and natural gums may be dispersed in a matrix of nonbiodegradable film forming materials which are resistant to solubility in water. Wielicki (U.S. Pat. No. 3,602,225) teaches the use of barrier films made of plasticized regenerated cellulose films. Comerford (U.S. Pat. No. 3,683,917) teaches the use of a cellulosic material coated with a water repellent material.

There exists in the market place the need for thermoplastics which are useful in molding, fiber, and film applications. For these applications, it is desirable that the thermoplastic blend be processable at a low melt temperature and have a high glass transition temperature. These thermoplastics should not contain volatile or extractable plasticizers. Moreover, there is a need in the marketplace for a biodegradable material for use in disposable articles such as diapers, razors, and the like. As an example, unlike films prepared from polymers such as PHB, the material should be amenable to both solvent casting and melt extrusion. In melt extruding this material, coextrusion with other thermoplastics should not be a requirement. The barrier properties of this new biodegradable material should be adequate so that coating with a water insoluble polymer is not required. The new material should disperse completely in the environment and not require coating with a water-soluble polymer. The mechanical properties of the material should be such that films of low modulus but of high tensile strength can be prepared.

Additionally, it is noted that there exists a need for biodegradable nonwoven articles. Nonwovens are widely used in a variety of products. For example, nonwoven fabrics are suitable for use in hygiene, sanitary and absorbent products, medical/surgical/hospital articles and applications, filter media, wipes, face masks, protective apparel, geotextiles, pressed board and other construction materials, composites, automotive applications, facing and backing materials, scrims, linings, insulation, agricultural fabrics, paint rollers, bedding, tablecloths, napkins, and many other disposable, limited use, durable and recyclable products. High loft nonwoven battings are used in a wide variety of products, including comforters, robe wear, and bra cups. Disposables include wipes, diapers, sanitary napkins and incontinent products. Generally nonwoven fabrics are based on polyester, cellulosic, acrylic, nylon, carbon, glass and other fibers which may be bonded with latex adhesives, binder fibers, scrims and nonwoven binder forms, or polymers in powder form. The bonding of nonwoven fabrics with binder fibers (webs, scrims or adhesive powders) provides a convenient method for making nonwoven fabrics without the need for water- or solvent-based adhesives which are less environmentally friendly. Nonwoven fabrics bonded with binder fibers are economical to produce, and provide a method for making articles, which are unique or superior in performance. Other applications are uses in yarns to increase strength and reduce pilling or linting, as well as in prepregs, preforms and a wide range of engineered composite structures.

Generally, as described in U.S. Pat. Nos. 4,217,426 and 4,419,507, linear, crystalline or partially crystalline polymers have been reported as useful for forming fusible interlining adhesives and in some instances as binder fibers. Indeed, binder fibers and powders made from poly (hexamethylene terephthalate) copolyesters (PHT) have been sold. Such adhesive powders and binder fibers include Eastobond® FA-300 which was formed from a copolyester having 20 mole % 1,4-butanediol and had a melting point of 125° C. as well as Eastobond® FA-250 which contained 20 mole % isophthalic acid and 20 mole % 1,4-butanediol and had a melting point of 104° C.

While previous polyesters and binder fibers may be suitable for certain purposes, such polyesters have not proven effective for applications where elasticity, compostability and/or biodegradability are needed.

SUMMARY OF THE INVENTION

The present invention, in part, concerns binary blends of cellulose esters and aliphatic-aromatic copolyesters, cellulose esters and aliphatic polyesters as well as ternary blends of cellulose esters and/or aliphatic polyesters and/or aliphatic-aromatic copolyesters and/or polymeric compounds as well as fibers, molded objects, and films prepared therefrom which have one or more of the above or below described desirable properties. More specifically, the present invention is directed to a blend comprising:

I.
- (A) about 5% to about 98% of a C1–C10 ester of cellulose having a DS/AGU of about 1.7 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and
- (B) about 2% to about 95% of an aliphatic-aromatic copolyester having an inherent viscosity of about 0.2 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

II.
- (A) about 5% to about 98% of a C1–C10 ester of cellulose having a DS/AGU of about 1.7 to 2.75 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and
- (B) about 2% to about 95% of an aliphatic polyester having an inherent viscosity of about 0.2 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

III.
- (A) about 4% to about 97% of a C1–C10 ester of cellulose having a DS/AGU of about 1.7 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane,
- (B) about 2% to about 95% of an aliphatic polyester and/or an aliphatic-aromatic copolyester having an inherent viscosity of about 0.2 to about 2.0 deciliters/gram as measured at a temperature of 25° C. for a 0.5 g sample in 100 ml of a 60/40 parts by weight solution of phenol/tetrachloroethane,
- (C) about 1% to about 94% of immiscible, partially miscible, or miscible polymeric compounds having an inherent viscosity of about 0.2 to about 2.0 deciliters/gram as measured at a temperature of 25° C. for a 0.5 g sample in 100 ml of a 60/40 parts. by weight solution of phenol/tetrachloroethane, said percentages being based on the weight of component (A) plus component (B) plus component (C);

IV.
(A) about 50% to about 99% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane,
(B) about 1% to about 50% of biodegradable additives, said percentages being based on the weight of component (A) plus component (B);

V.
(A) about 95% to about 99.95% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane,
(B) about 0.05% to about 5% of immiscible hydrophobic agent, said percentages being based on the weight of component (A) plus component (B).

The present invention is also directed to:

VI. An essentially linear, random, semicrystalline aliphatic-aromatic copolyester which has an inherent viscosity of about 0.5 to 1.8 deciliters/gram as measured at a temperature of 25° C. for a 0.5 g sample in 100 mL of a 60/40 parts by weight solution of phenol/tetrachloroethane and has a melting point between 75° C. and 160° C.

VII. A mixture of 50 to 99% of (VI) and about 1% to about 50% of biodegradable additives, said percentages being based on the weight of component (VI) plus biodegradable additives.

VIII. A fiber or mixture of fibers prepared from a copolyester having a dicarboxylic acid component and a diol component where the copolyester contains repeat units of the following structures:

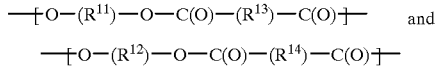

and

In the above formulas $R^{11}$ and $R^{12}$ are selected from the group consisting of $C_2$–$C_{12}$ alkylene, $C_5$–$C_{10}$ cycloalkylene, $C_2$–$C_{12}$ oxyalkylene and mixtures thereof, and $R^{11}$ and $R^{12}$ are 100% of the diol component. The dicarboxylic acid component contains an aliphatic dicarboxylic acid $R^{13}$, and an aromatic or cycloaliphatic dicarboxylic acid component $R^{14}$. $R^{13}$ is selected from the group consisting of $C_0$–$C_{10}$ alkylene or $C_2$–$C_4$ oxyalkylene and mixtures thereof and $R^{14}$ is selected from the group consisting of $C_6$–$C_{12}$ aryl and $C_5$–$C_{10}$ cycloaliphatic and mixtures thereof. The mole % of $R^{13}$ in the copolyester ranges from about 45 to 95% of the dicarboxylic acid component and the mole % of $R^{14}$ is from about 5 to 55% of the dicarboxylic acid component. The polyester can be formed in the presence of 0 to about 20 mole % of at least one amine compound selected from the group consisting of aminoalcohols, aminoacids, diamines, lactams and mixtures thereof. Such copolyesters preferably have a melting point ranging from about 75° C. to about 160° C. These copolyester fibers are in a form selected from the group consisting of melt blown, spunbond, spun fibers and combinations thereof.

IX. A composition formed from at least two polyesters with the first polyester being polylactic acid and the second polyester composition formed from a dicarboxylic acid component and a diol component such that the second polyester contains repeat units of the following structures:

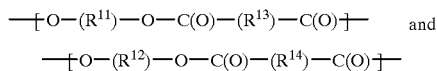

In the above formulas $R^{11}$ and $R^{12}$ are selected from the group consisting of $C_2$–$C_{12}$ alkylene, $C_5$–$C_{10}$ cycloalkylene, $C_2$–$C_{12}$ oxyalkylene and mixtures thereof, and $R^{11}$ and $R^{12}$ are 100% of the diol component. The dicarboxylic acid component of the second copolyester contains an aliphatic dicarboxylic acid $R^{13}$, and an aromatic or cycloaliphatic dicarboxylic acid component $R^{14}$. $R^{13}$ is selected from the group consisting of $C_0$–$C_{10}$ alkylene, $C_5$–$C_{10}$ cycloalkylene, or $C_2$–$C_4$ oxyalkylene and mixtures thereof, and $R^{14}$ is selected from the group consisting of $C_6$–$C_{12}$ aryl and cycloaliphatic and mixtures thereof. The mole % of $R^{13}$ ranges from about 45 to 95% of the dicarboxylic acid component and the mole % of $R^{14}$ is from about 5 to 55% of the dicarboxylic acid component.

The invention answers the problems occuring in previous polyesters and fibers by providing polyesters and fibers having enhanced elasticity properties and improved dyeing properties. The polyesters and fibers of the invention are capable of demonstrating superior thermoplastic flow characteristics while providing good bonding versatility. Furthermore, the polyesters and fibers of the invention can be used alone or they can be formulated as a polymer additive for imparting improved dyeing, finishing and printing properties to other compositions. Indeed, the polyesters of the invention are suitable for use in a wide variety of applications and are especially suitable for bonding cellulosic, polylactic acid (PLA) and other "green" (biodegradable/compostable) compositions, as well as some superabsorbent polymers (SAP), in hygiene and other absorbent products.

BRIEF DESCRIPTION OF THE DRAWINGS

FIG. 6A is the front view and FIG. 6B is a side view of the preferred quenching device.

DETAILED DESCRIPTION OF THE INVENTION

Figure 1A:
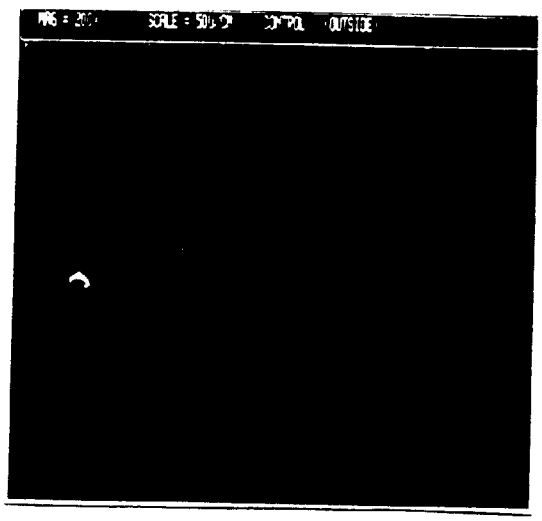
FIG. 1A Scanning electron microscopy (SEM) photograph of the outer, smooth surface of a cellulose acetate (DS=1.7) film formed by drawing a film from a 20 wt. % solution of cellulose acetate in a 50/50 (vol./vol.) mixture of water/acetone. Magnification is 200×.

We have found that cellulose esters form binary blends with aliphatic polyesters and aliphatic-aromatic copolyesters as well as ternary blends with aliphatic polyesters/polyacrylates, aliphatic polyesters/polyvinyl acetates, aliphatic polyesters/polyvinyl alcohol, aliphatic polyesters/polyvinyl chloride, aliphatic polyesters/polycarbonates, aliphatic polyesters/polyvinyl acetate-polyethylene copolymers, aliphatic polyesters/cellulose ethers, aliphatic polyesters/polyamides, aliphatic-aromatic copolyesters/polyacrylates, aliphatic-aromatic copolyesters/polyvinyl acetates, aliphatic-aromatic copolyesters/polyvinyl alcohol, aliphatic-aromatic copolyesters/polyvinyl chloride, aliphatic-aromatic copolyesters/polycarbonates, aliphatic-aromatic copolyesters/polyvinyl acetate-polyethylene copolymers, aliphatic-aromatic copolyesters/cellulose ethers, or aliphatic-aromatic copolyesters/polyamides, as well as other polymers, to produce resins which are useful as molded or extruded plastic objects, fibers, or films. Moreover, various additives can be added to the blend to enhance properties such as water vapor transmission rates or biodegradability.

The cellulose esters of the present invention generally comprise repeating units of the structure:

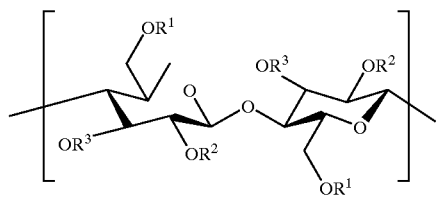

wherein $R^1$, $R^2$, and $R^3$ are selected independently from the group consisting of hydrogen or straight chain alkanoyl having from 2 to 10 carbon atoms.

The cellulose esters useful in formulating the blend can be a cellulose triester or a secondary cellulose ester. Examples of cellulose triesters include cellulose triacetate, cellulose tripropionate, or cellulose tributyrate. Examples of secondary cellulose esters include cellulose acetate, cellulose acetate propionate, and cellulose acetate butyrate. These cellulose esters are described in U.S. Pat. Nos. 1,698,049; 1,683,347; 1,880,808; 1,880,560; 1,984,147, 2,129,052; and 3,617,201, incorporated herein by reference in their entirety.

The cellulose esters useful in the present invention can be prepared using techniques known in the art or are commercially available, e.g., from Eastman Chemical Company, Inc., Kingsport, Tenn., U.S.A.

The cellulose esters useful in the present invention have at least 2 anhydroglucose rings and typically have between 2 and 5,000 anhydroglucose rings; also, such polymers typically have an inherent viscosity (IV) of about 0.2 to about 3.0 deciliters/gram, preferably about 1 to about 1.5, as measured at a temperature of 25° C. for a 0.5 gram sample in 100 ml of a 60/40 by weight solution of phenol/tetrachloroethane. In addition, the DS/AGU of the cellulose esters useful herein ranges from about 1.7 to about 3.0. Preferred esters of cellulose include cellulose acetate (CA), cellulose propionate (CP), cellulose butyrate (CB), cellulose acetate propionate (CAP), cellulose acetate butyrate (CAB), cellulose propionate butyrate (CPB), and the like. CAP and CAB are more preferred cellulose esters. The most preferred ester of cellulose is CAP.

For binary blends, the preferred esters of cellulose for blending with aliphatic-aromatic copolyesters are CAP and CAB. The preferred ester of cellulose is CAP having a DS/AGU of 2.1–2.85 wherein the DS/AGU of acetyl ester is 1–50% of the total ester content. The most preferred CAP's have a DS/AGU of 2.5–2.75 wherein the DS/AGU of acetyl ester is 4–30% of the total ester content.

For binary blends, the preferred esters of cellulose for blending with aliphatic polyesters are CA, CAP, and CAB. A preferred ester of cellulose is CA having a DS/AGU of 1.7–2.75. Another preferred ester of cellulose is CAP having a DS/AGU of 1.7–2.75 wherein the DS/AGU of acetyl ester is 1–50% of the total ester content. The most preferred CAP's have a DS/AGU of 2.1–2.6 wherein the DS/AGU of acetyl ester is 4–30% of the total ester content. It is also preferred that the CAP's have a glass transition temperature (Tg) of about 140° C. to 180° C.

For ternary blends, the preferred esters of cellulose for blending with aliphatic polyesters and/or aliphatic-aromatic copolyesters and/or polymeric compounds, biodegradable additives, or hydrophobic agents are CAP and CAB. The preferred ester of cellulose is CAP having a DS/AGU of 1.7–3.0 wherein the DS/AGU of acetyl ester is 1–50% of the total ester content. The most preferred CAP's have a DS/AGU of 2.5–2.75 wherein the DS/AGU of acetyl ester is 4–30% of the total ester content.

The aliphatic-aromatic copolyesters that are useful in blends in the present invention are random copolymers and preferably comprise repeating units of:

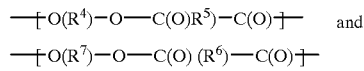

wherein $R^4$ and $R^7$ are selected from one or more of the following groups consisting of $C_2$–$C_{12}$ alkylene or oxyalkylene; $C_2$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; $C_5$–$C_{10}$ cycloalkylene substituted with one to four substituents independently selected from the group consisting of halo, $C_6$–$C_{10}$ aryl, and $C_1$–$C_4$ alkoxy; $R^5$ is selected from one or more of the following groups consisting of $C_0$–$C_{12}$ alkylene or oxyalkylene; $C_1$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; and $C_5$–$C_{10}$ cycloalkylene substituted with one to four substituents independently selected from the group consisting of halo, $C_6$–$C_{10}$ aryl, and $C_1$–$C_4$ alkoxy; $R^6$ is selected from one or more of the following groups consisting of $C_6$–$C_{10}$ aryl, $C_6$–$C_{10}$ aryl substituted with one to four substituents independently selected from the group consisting of halo, $C_1$–$C_4$ alkyl, and $C_1$–$C_4$ alkoxy.

It is preferred that said aliphatic-aromatic copolyester comprises 10 to 1,000 repeating units. Most preferred is when said aliphatic-aromatic copolyester comprises 15 to 600 repeating units.

In the present invention, the mole % of $R^5$ in the copolymer can range from 30 to 95%, and the mole % of $R^6$ can range from 5 to 70%. A more preferred range is when the mole % of $R^5$ is from about 45 to 85% and the mole % of $R^6$ is from about 15–55 mol %. The most preferred ranges, in general, depend upon the needed level of miscibility of the copolyester with the cellulose esters and the physical properties desired. The most preferred ranges for miscible blends is when $R^5$ is glutaric and the mole % of $R^5$ in the copolyester ranges from 70 to 85% and the mole % of $R^6$ ranges from 15–30 mol %. The most preferred ranges for partially miscible blends is when $R^5$ is glutaric and the mol % of $R^5$ in the copolyester ranges from 45 to 60% and the mole % of $R^6$ ranges from 40–55 mol %. The range of miscibility of a particular blend can change as the molecular weight of a blend component is changed. In general, an aliphatic-aromatic polyester having a lower molecular weight or inherent viscosity will be more miscible with a given cellulose ester relative to the higher molecular weight polyester.

It is preferred that the aliphatic-aromatic copolyester has an inherent viscosity of about 0.4 to about 1.2 as measured at a temperature of 25° C. for a 0.5 gram sample in 100 ml of a 60/40 by weight solution of phenol/tetrachloroethane.

As used herein the terms "alkyl" and "alkylene" refer to either straight or branched chain moieties such as —$CH_2$—$CH_2$—$CH_2$—$CH_2$— and —$CH_2CH(X)$—$CH_2$—. Also, all of the carbon atoms of the cycloalkyl and cycloalkylene moieties are not necessarily in the ring structure, e.g., a $C_8$ cycloalkyl group can be cyclooctyl or dimethylcyclohexyl. The term "oxyalkylene" refers to alkylene chains containing from 1 to 4 ether oxygen groups.

One type of aliphatic polyester useful in the present invention preferably comprises repeating units of:

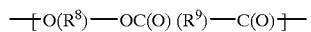

wherein $R^8$ is selected from one or more of the following groups consisting of $C_2$–$C_{12}$ alkylene or $C_2$–$C_{12}$ oxyalkylene; $C_2$–$C_{12}$ alkylene or $C_2$–$C_{12}$ oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; $C_5$–$C_{10}$ cycloalkylene substituted with one to four substituents independently selected from the group consisting of halo, $C_6$–$C_{10}$ aryl, and $C_1$–$C_4$ alkoxy; $R^9$ is selected from one or more of the following groups consisting of $C_0$–$C_{12}$ alkylene or oxyalkylene; $C_1$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; and $C_5$–$C_{10}$ cycloalkylene substituted with one to four substituents independently selected from the group consisting of halo, $C_6$–$C_{10}$ aryl, and $C_1$–$C_4$ alkoxy.

It is preferred that $R^8$ is $C_2$–$C_6$ alkylene, $C_4$–$C_8$ oxyalkylene, or $C_5$–$C_{10}$ cycloalkylene; and $R^9$ is $C_0$–$C_{10}$ alkylene, $C_2$ oxyalkylene or $C_5$–$C_{10}$ cycloalkylene.

It is more preferred that $R^8$ is $C_2$–$C_4$ alkylene, $C_4$–$C_8$ oxyalkylene, or $C_5$–$C_{10}$ cycloalkylene; and $R^9$ is $C_2$–$C_4$ alkylene, $C_2$ oxyalkylene or $C_5$–$C_{10}$ cycloalkylene.

It is preferred that said aliphatic polyester comprises 10 to 1,000 repeating units. Most preferred is when said aliphatic polyester comprises 15 to 600 repeating units. The terms "alkyl" and "alkylene" are as defined above.

A second type of aliphatic polyester includes polyhyroxyalkanoates which are comprised of repeat units of the following structure:

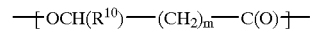

wherein m is an integer of 0 to 10, and $R^{10}$ is selected from the group consisting of hydrogen; $C_1$–$C_{12}$ alkyl; $C_1$–$C_{12}$ alkyl substituted with one to four substituents independently selected from the group consisting of halo, $C_6$–$C_{10}$ aryl, and $C_1$–$C_4$ alkoxy; $C_5$–$C_{10}$ cycloalkyl; and $C_5$–$C_{10}$ cycloalkyl substituted with one to four substituents independently selected from the group consisting of halo, $C_6$–$C_{10}$ aryl, and $C_1$–$C_4$ alkoxy.

For the purpose of this invention aliphatic polyester is defined as an aliphatic polyester which does not contain significant quantities of carbonate linkages. Furthermore, polyester is defined as a polyester prepared by a condensation process or by a biological process.

Typical polymeric compounds for ternary blends include polyacrylates such as polymethyl methacrylate (PMMA), polyethyl methacrylate (PEMA), or copolymers thereof such as those which are commercially available from Rohm and Haas. Polyvinyl acetate, polyvinyl alcohol, polyvinyl chloride, and polyvinyl acetate-polyethylene copolymers are also useful in ternary blends and are common commercial polymers which are available from companies such as Air Products and Chemicals, Inc. Polycarbonates, available from GE Plastics, are also useful in ternary blends. Cellulose ethers are commercially available from companies such as Aqualon Co. and are also useful in ternary blends. Polyamides, e.g., nylon 6 which is available from Ashley Polymers, Inc., is also highly useful in ternary blends. For this invention, preferred polyacrylates are PMMA polymers. The preferred polyvinyl alcohols are those that are 5–60% hydrolyzed and have a molecular weight of 1,000 to 30,000. The preferred cellulose esters are hydroxypropyl cellulose (HPC) and hydroxypropyl methyl cellulose (HPMC). The preferred polyvinyl acetate will have a molecular weight of 1,000 to 1,000,000.

Typical biodegradable additives for binary and ternary blends of this invention include micro-crystalline cellulose, cellulose monoacetate, starch and other carbohydrates. The preferred materials are micro-crystalline cellulose, available from FMC, or starch, available from National Starch Co., which typically have a particle size of 1–200 microns; the preferred particle size is 0.1–15 microns. Also preferred are cellulose monoacetates which have a DS/AGU of 1.2 to 0.4 and will be either water soluble or water swellable (U.S. patent applications Ser. Nos. 509,385; 509,400 (1990)).

Typical immiscible hydrophobic agents include paraffin, monoacyl carbohydrates, and monoglycerides. An example of a monoacyl carbohydrate is 6-O-sterylglucopyranoside. The preferred hydrophobic agents are monoglycerides containing C12–C18 fatty acids. These monoglycerides containing C12–C18 fatty acids may also be optionally acylated with 5–95% acetyl, propionyl, butyryl, or succinyl groups. The more preferred monoglycerides are those containing C16–C18 fatty acids. The most preferred hydrophobic agent is glyceryl monostearate.

The preparation of polyesters and copolyesters is well known in the art (U.S. Pat. No. 2,012,267, incorporated herein by reference in its entirety). Such reactions are usually carried out at temperatures from 150° C. to 300° C. in the presence of polycondensation catalysts such as titanium alkoxides, manganese diacetate, antimony oxide, dibutyl tin diacetate, zinc chloride, or combinations thereof. The catalysts are typically employed in amounts between 10 to 1000 ppm, based on total weight of the reactants. For the purpose of the present invention, a representative aliphatic polyester is the polycondensation product of dimethyl glutarate and 1,6-hexanediol. This polyester, poly (hexamethylene glutarate), is produced when dimethyl glutarate and 1,6-hexanediol are heated at approximately 210° C. for 4 hours and then at 260° C. for 1.5 hours under vacuum in the presence of 100 ppm of Ti. A representative aliphatic-aromatic copolyester is poly(tetramethylene glutarate-co-terephthalate) containing 30 mole percent terephthalate. This polyester is produced when dimethyl glutarate, dimethyl terephthalate, and 1,4-butanediol are heated at 200° C. for 1 hour then at 245° C. for 0.9 hour under vacuum in the presence of 100 ppm of Ti present initially as Ti(OiPr)$_4$.

It is preferred that said aliphatic-aromatic copolyester for use in blending is prepared from any polyester forming combination of dicarboxylic acids or derivatives thereof, and diols. Said dicarboxylic acids are selected from the group consisting of the following diacids: malonic, succinic, glutaric, adipic, pimelic, azelaic, sebacic, fumaric, 2,2-dimethylglutaric, suberic, 1,3-cyclopentanedicarboxylic, 1,4-cyclohexanedicarboxylic, 1,3-cyclohexanedicarboxylic, diglycolic, itaconic, maleic, 2,5-norbornanedicarboxylic, terephthalic, isophthalic, 2,6-naphthoic, 1,5-naphthoic, and ester forming derivatives thereof, and combinations thereof; and said diols are selected from the group consisting of ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, tetraethylene glycol, and combinations thereof.

Specific examples of preferred aliphatic-aromatic copolyesters for blending include poly(tetramethylene glutarate-co-terephthalate-co-diglycolate) [50/45/5], poly (tetramethylene glutarate-co-terephthalate) [50/50], poly (tetramethylene glutarate-co-terephthalate) [60/40], poly (tetramethylene glutarate-co-terephthalate) [70/30], poly (tetramethylene glutarate-co-terephthalate) [85/15], poly (ethylene glutarate-co-terephthalate) [70/30], poly (tetramethylene adipate-co-terephthalate) [85/15], poly (tetramethylene succinate-co-terephthalate) [85/15], and poly(tetramethylene-co-ethylene glutarate-co-terephthalate) [50/50,70/30].

The aliphatic-aromatic copolyesters (referred to as AAPE herein) that are useful in the present invention without requiring blending of a significant amount of another component are essentially linear, random copolymers and preferably comprise repeating units of:

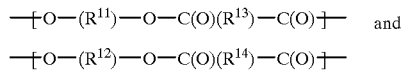 and

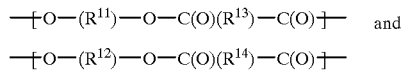

wherein $R^{11}$ and $R^{12}$ are the same and are selected from the groups consisting of C2–C8 alkylene or oxyalkylene; $R^{13}$ is selected from one or more of the groups consisting of C0–C8 alkylene or C2–C4 oxyalkylene, and the mole % of $R^{13}$ is from about 95–35%; $R^{14}$ is selected from the group of C6–C10 aryl, and the mole % of $R^{14}$ is from about 5–65%.

More preferred AAPE are those wherein $R^{11}$ and $R^{12}$ are the same and are selected from C2–C4 alkylene; $R^{13}$ is selected from one or more of the groups consisting of C2–C6 alkylene or C2 oxyalkylene, and the mole % of $R^{13}$ is from about 95–40%; $R^{14}$ is 1,4-disubstituted-C6 aryl, and the mole % of $R^{14}$ is from about 5–60%. The most preferred compositions for these AAPE are those prepared from the following diols and diacids (or polyester forming derivatives thereof) in the following mole %:

(1) Glutaric acid (30–65%); diglycolic acid (0–10 mol %); terephthalic acid (25–60%); 1,4-butanediol (100 mole %).

(2) Succinic acid (30–85%); diglycolic acid (0–10%); terephthalic acid (5–60%); 1,4-butanediol (100 mole %).

(3) Adipic acid (30–65%); diglycolic acid (0–10%); terephthalic acid (25–60%); 1,4-butanediol (100 mole %).

Specific examples of preferred AAPE for applications where blending is not required include poly(tetramethylene glutarate-co-terephthalate-co-diglycolate) [50/45/5], poly (tetramethylene glutarate-co-terephthalate) [50/50], poly (tetramethylene glutarate-co-terephthalate) [60/40], poly (tetramethylene glutarate-co-terephthalate) [40/60], poly (tetramethylene succinate-co-terephthalate) [85/15], poly (ethylene succinate-co-terephthalate) [70/30], poly (tetramethylene adipate-co-terephthalate) [85/15], and poly (tetramethylene succinate-co-terephthalate) [70/30].

It is preferred that said aliphatic polyester is prepared from any polyester forming combination of the following:

(i) hydroxy acids, (ii) dicarboxylic acids or derivatives thereof, and (iii) diols.

Said hydroxy acids are selected from the group consisting of 4-(hydroxymethyl)cyclohexanecarboxylic acid, hydroxypivalic acid, 6-hydroxyhexanoic acid, glycolic acid, lactic acid, ester forming derivatives thereof, and combinations thereof; said dicarboxylic acids are selected from the group consisting of the following diacids: malonic, succinic, glutaric, adipic, pimelic, azelaic, sebacic, fumaric, 2,2-dimethylglutaric, suberic, 1,3-cyclo-pentanedicarboxylic, 1,4-cyclohexanedicarboxylic, 1,3-cyclohexanedicarboxylic, diglycolic, itaconic, maleic, 2,5-norbornanedicarboxylic, ester forming derivatives thereof, and combinations thereof; and said diols are selected from the group consisting of ethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, diethylene glycol, triethylene glycol, tetraethylene glycol, and combinations thereof.

Specific examples of preferred aliphatic polyesters include, polyhydroxybutyrate, a copolymer of polyhydroxybutyrate and polyhydroxyvalerate, poly(hexamethylene glutarate), poly(hexamethylene adipate), poly(ethylene sebacate), poly(tetramethylene glutarate), poly (tetramethylene adipate), poly(tetramethylene sebacate), poly(ethylene glutarate), poly(ethylene succinate), poly (tetramethylene succinate), or poly(ethylene adipate).

Other aliphatic polyesters useful in the present invention are polyhydroxyalkanoates that are derived from biological sources. A number of laboratories (cf *Makromol. Chem.,* 191, 1957–1965 (1990); *J. Bacteriol.,* 154, 870 (1983); *Macromolecules,* 22, 1106 (1989)) have demonstrated that microorganisms, e.g., *Pseudomonas oleovorans, Alcali-*

*genes eutrophus, Bacillus megaterium Rhodospirillum rubrum,* can accumulate polyhydroxyalkanoates containing alkyl pendant groups when grown on either n-alkanes or n-alkanoic acids under nutrient limiting conditions. In the case of *P. oleovorans,* a polyhydroxyalkanoate with a phenyl pendant group can be produced. The polymer forms as intracellular granules which provides the cell with a reserve of fatty acid in a form that is osmotically inert. When the microorganism is faced with energy or starvation conditions the polymer is degraded as a food source; hence, bacterial polyhydroxyalkanoates are inherently biodegradable.

Polyhydroxyalkanoates derived from biological sources are rarely homopolymers. During biosynthesis, carbon segments, typically two carbon fragments, are either removed or added to the original alkanoate resulting in the formation of a copolymer (*Int. J. Biol. Macromol.,* 11, 49–55 (1989)). For example, when *P. oleovorans* is fed either n-octane or n-octanoic acid as the only carbon source, the product produced is a copolymer which contains mostly C6 and C8 units.

Any of the blends, AAPEs, films, plastic objects, and fibers of the invention can optionally additionally comprise 0.001 to 50 weight percent, based on the total weight of the composition, of at least one additional additive selected from a non-polymeric plasticizer, a thermal stabilizer, an antioxidant, a pro-oxidant, an acid scavenger, an ultraviolet light stabilizer, a promoter of photodegradation, inorganics, and colorants. Typical non-polymeric plasticizers include dioctyl adipate, phosphates, and diethyl phthalate. Representative inorganics include talc, $TiO_2$, $CaCO_3$, $NH_4Cl$, and silica. Colorants can be monomeric, oligomeric, and, of course, polymeric. Preferred polymeric colorants are aliphatic polyesters, aliphatic-aromatic copolyesters, or aromatic polyesters in which the color producing monomer, i.e., a dye, is covalently incorporated into the polymer. Such representative polymeric colorants are described by Weaver et al. in U.S. Pat. Nos. 4,892,922, 4,892,923, 4,882,412, 4,845,188, 4,826,903, and 4,749,773 and are incorporated herein by reference in their entirety. These polymeric dyes are represented by poly(tetramethylene terephthalate) containing 10% 1,5-bis(o-carboxyanilino)anthraquinone.

Of course, it is also preferred, but not required, that the blends of the invention, as well as the films, plastic objects, and fibers prepared from the blends, be compatible and/or biodegradable. The preferred blends, films, plastic objects, and fibers are compatible as evidenced by improved mechanical properties, having a single Tg, and/or being substantially clear or substantially non-hazy. It is also preferred, but not required, that the AAPE, as well as the films, plastic objects, and fibers prepared from the AAPE be biodegradable.

Films made from the blends have good tensile properties and can be very flexible depending upon the type of cellulose ester and aliphatic polyesters, aliphatic-aromatic copolyesters, and/or polymeric compound selected. Many of the films have good optical properties, i.e., are preferably substantially clear; the films can also contain significant quantities of colorant (i.e., pigment or dye). Because these films can contain dyes or pigments, extensive purification of PHA, such as PHB, to remove cellular material is not required.

For film used in environmentally non-persistent applications, it is preferred that the blend used to make the film be comprised of a cellulose ester with a DS of (2.1–2.75) and with a high Tg (140°–180° C.). Since the blends of this invention generally exhibit a Tg which can be predicted from the equation, $Tg_{12}=Tg_1 W\%_1 + Tg_2 W\%_2$, use of a cellulose ester with a higher Tg permits the incorporation of more polyester into the blend than is possible when using a cellulose ester with a lower Tg while still maintaining equivalent blend Tg's. Moreover, we have surprisingly found that because the lower DS cellulose ester generally has a higher modulus, incorporation of more polyester in the blend with the low DS cellulose ester leads to films with equivalent mechanical properties to films made from blends composed of a cellulose ester with a lower Tg and lower polyester content. Incorporation of more polyester in the blend is highly desirable since the blends with higher polyester content will biodegrade at a faster rate.

Of course, many of the AAPEs of this invention which do not require blending are also useful in film applications. While these AAPE do not have a melting point as high as that of poly(ethylene terephthalate), the AAPE have higher melting points than those generally observed with aliphatic polyesters and are therefore useful in many applications, particularly those requiring biodegradability. Succinic acid based AAPEs show particularly good utility in these applications due to their relatively high melting points. These copolyesters have been shown to be degradable even though they are semicrystalline and contain substantial amounts of aromatic groups. Furthermore, diglycolic acid has been found to be a useful comonomer for these AAPE because it aids in the initial breakup of the films.

These AAPEs are also particularly useful in molded parts, extruded objects, fibers, non-wovens, and foamed objects which benefit from being biodegradable. Films and fibers made from these copolyesters can be oriented. Orientation in many of these copolymers (especially those containing 1,4-butanediol) is accompanied by improved physical properties and a change from being opaque to being clear. AAPE films can be oriented uniaxially or biaxially and can be oriented in a blown film operation.

The blends and/or AAPE of this invention are useful in packaging applications where thin films are desirable. Many of the blends and/or AAPE of this invention are particularly useful as thin barrier films where they must function as a barrier and/or be biodegradable. For example, these blends are useful as protective barrier films and may be used in disposable absorbent articles such as infant diapers, incontinence briefs, sanitary napkins, tampons, bed liners, bedpan liners, bandages, and the like. It is preferred that the films of the invention have a tangent modulus of $2.5 \times 10^5$ psi to $0.01 \times 10^5$ psi, a tensile strength of at least about $0.5 \times 10^3$ psi, an average tear force of at least about 7.0 g/mil, and an elongation at break of at least about 5%. Also preferred is wherein said films have a thickness of about 0.1 mil to about 20 mil and a water vapor transmission rate less than about 500 g mil/m²-24 hours.

The blends and/or AAPEs of this invention can also be used in the other parts of disposable diapers. In addition to being used as a protective barrier film, these blends and/or AAPEs can be used as tabs, nonwovens, fibers, tape, and other parts needed in the construction of a diaper.

We have found that films prepared from these binary and ternary blends of cellulose esters as well as from AAPEs have desirable moisture barrier properties. With the blends, the specific rates can be modified by modification of the blend composition. For example, the water vapor transmission rates can be controlled by the amount of aliphatic polyester, aliphatic-aromatic copolyester, or polymeric compounds present in the binary or ternary blends. The water vapor transmission rates can also be controlled by the amount of aromatic dicarboxylic acid monomer present in the aliphatic-aromatic copolyester component of the blend.

Of course, the water vapor transmission rates of the blends can be additionally controlled by the addition of an immiscible hydrophobic agent.

The blends and/or AAPEs of this invention are also useful as molded plastic parts or as solid, foamed plastic objects. Examples of such parts include eyeglass frames, toothbrush handles, toys, automotive trim, tool handles, camera parts, razor parts, ink pen barrels, disposable syringes, bottles, wipes and the like. The plastic parts, especially those made by a foamed method which gives the plastic part increased surface area, of this invention are particularly useful in applications where it is desired that the plastic part be environmentally non-persistent. Injection molding bars made from the blends and/or AAPE of the invention typically have a flexural modulus of $5.0 \times 10^5$ psi to $0.1 \times 10^5$ psi, a flexural strength of $13 \times 10^3$ psi to $0.1 \times 10^3$ psi, and a notched Izod (23° C.) of 1.0 to 25 ft-lb/in. It is preferred that the molding bars have a flexural modulus of $3.8 \times 10^5$ psi to $1.5 \times 10^5$ psi, a flexural strength of $11.4 \times 10^3$ psi to $4 \times 10^3$ psi, and a notched Izod (23° C.) of 2 to 15 ft-lb/in.

The blends and/or AAPE of this invention are also useful as fibers. Examples of fiber applications include cigarette filters, diaper topsheet, sanitary napkins, wipes, fishing line, fishing nets, fiber for producing surgical clothing, hygiene articles, absorbent fibers, fibers for conveying liquids, and the like. We have found that, in addition to being spun from an appropriate solvent, the blends and/or AAPE of this invention can be melt spun to produce fibers with excellent strength. The fibers can be oriented by drawing the fiber after spinning or by orientation during the spinning (cabinet orientation). Fibers produced from the blends and/or AAPEs have excellent shape retention even for fibers with complex cross-sectional shapes. We have also found that the fibers can be readily crimped. Fiber produced from the blends and/or AAPEs typically have a denier/filament (DPF) of 30–0.1. The preferred denier is 10–1.5 DPF. For fluid management, the fiber can contain hydrophobic agents or, optionally, can be coated with hydrophobic agents.

The blends, films, plastic objects, and fibers prepared from the blends of the invention have a melt temperature between about 120° C. and about 280° C. The preferred melt temperature range from 150° C. to 190° C. Also, such blends, films, plastic objects, and fibers have a glass transition temperature (Tg) as measured by differential scanning calorimetry (DSC) or dynamic mechanical thermal analysis (DMTA) of about 25° C. to about 200° C. The preferred range for the glass transition temperatures is 50° C. to 100° C. The blends and films are also preferably non-tacky.

The preferred AAPE of this invention and products made therefrom have melting points between 75° C. and 160° C. The more preferred range is between 80° C. and 140° C.

For the blends of the invention containing cellulose esters and aliphatic-aromatic copolyesters, the preferred level of polyester in the blend depends, in general, upon the desired level of miscibility of the blend and upon the needed physical properties. A preferred range is when component I(B) is present in an amount of about 5% to about 75% and component I(A) is present in an amount of about 25% to about 95% and that component I(A) have a DS of 2.1–2.75. When it is desirable to have higher tensile strength, flexural strength, and flexural modulus in molded plastic objects and the like, a more preferred range is when component I(B) is present in an amount of about 5% to about 25% and that component I(B) has an I.V. of 0.2–2.0 and component I(A) is present in an amount of about 75% to about 95% and that component I(A) have a DS of 2.1–2.75. When it is desirable that the blend used for the molded plastic part be miscible, that is optically clear, it is preferred that component I(B) have an I.V. of 0.3–0.6 and be present in the amount of 5–25%.

When it is desirable to have lower modulus blends for applications such as films, bottles, fiber, and the like, a more preferred range is when component I(B) is present in an amount of about 30% to about 75% and component I(A) is present in an amount of about 25% to about 70% and that component I(A) have a DS of 2.1–2.75. When it is desirable to have a miscible blend useful in films, bottles, fiber, and the like, a more preferred range is when component I(B) is present in an amount of about 30% to about 55%, $R^5$ is glutaric acid present in the 70–85% range, and component I(A) is present in an amount of about 45% to about 70% and that component I(A) have a DS of 2.5–2.75. The most preferred partially miscible blend useful in films is when component I(B) is present in an amount of about 60% to about 75%, $R^5$ is glutaric acid present in the 45–60% range, and component I(A) is present in an amount of about 25% to about 40% and that component I(A) have a DS of 2.5–2.75.

For the blends of the invention containing cellulose esters and aliphatic polyesters it is preferred that component II(B) is present in an amount of about 10% to about 60% and component II(A) is present in an amount of about 40% to about 90% and that component II(A) have a DS of 2.1–2.7. Most preferred is when component II(B) is present in an amount of about 35% to about 55% and component II(A) is present in an amount of about 45% to about 65% and that component II(A) have a DS of 2.1–2.5.

For the blends of the invention containing cellulose esters and/or aliphatic polyesters and/or aliphatic-aromatic copolyesters and/or polymeric compounds it is preferred that component III(B) is present in an amount of about 10% to about 50% component III(A) is present in an amount of about 40% to about 88% and that component III(A) have a DS of 2.1–2.75, and that component III(C) is present in the amount of 2% to 10%. Also preferred is when component III(B) is present in an amount of about 2% to about 10%, component III(A) is present in an amount of about 40% to about 88% and that component III(A) have a DS of 2.1–2.75, and that component III(C) is present in the amount of 10% to 50%. Additionally preferred is when component III(B) is present in an amount of about 40% to about 88%, component III(A) is present in an amount of about 2% to about 10% and that component III(A) have a DS of 2.1–2.7, and that component III(C) is present in the amount of 10% to 50%. Also preferred is when component III(B) is present in an amount of about 10% to about 50%, component III(A) is present in an amount of about 2% to about 10% and that component III(A) have a DS of 2.1–2.7, and that component III(C) is present in the amount of 40% to 88%. Another preferred range is when component III(B) is present in an amount of about 20% to about 40%, component III(A) is present in an amount of about 20% to about 40% and that component III(A) have a DS of 2.1–2.7, and that component III(C) is present in the amount of 20% to 40%.

For the binary and ternary blends containing biodegradable additives it is preferred that component IV(B) is present in an amount of about 1% to about 10% and component IV(A) is present in an amount of about 90% to about 99%.

For the binary and ternary blends containing immiscible hydrophobic agents it is preferred that component V(B) is present in an amount of about 0.1% to about 1% and component V(A) is present in an amount of about 99% to about 99.9%.

Physical mixing of the components to form a blend can be accomplished in a number of ways such as mixing the components in the appropriate solvent (e.g., acetone, THF, $CH_2Cl_2$/MeOH, $CHCl_3$, dioxane, DMF, DMSO, AcOMe, AcOEt, pyridine) followed by film casting or fiber extrusion. The blend components can also be mixed by thermally compounding them. The most preferred method is by thermally compounding the blend in an apparatus such as a torque rheometer, a single screw extruder, or a twin screw extruder. The blends produced by thermal compounding can be converted to thin films by a number of methods known to those skilled in the art. For example, thin films can be formed by dipcoating as described in U.S. Pat. No. 4,372,311, by compression molding as described in U.S. Pat. No. 4,427,614, by melt extrusion as described in U.S. Pat. No. 4,880,592, by melt blowing, or by other similar methods. The blends can be converted to molded plastic objects by injection molding as well as by extrusion into a sheet from which an object is cut or stamped. The thermally compounded blends can be used for melt extrusion of fiber as well.

The fibers and films prepared from the blends and/or the AAPE of the present invention are useful in applications where protective barrier films are desirable. For example, they may be used in absorbent articles such as infant diapers, incontinence briefs (adult diapers), sanitary napkins, tampons, bed liners, bedpans, bedpan liners, bedpads, bandages, wipes and the like. The biodegradable films, fibers, AAPE, and blends of the invention are particularly useful in disposable articles because of environmental considerations. The blends and/or films of the invention can also be used to make non-absorbent articles such as packaging materials (for example, foam sheets for packaging), food bags, trash bags, agricultural compost sheets, film base for tape and photographic film, as well as solid plastic articles such as syringes and camera cases.

Biodegradable materials, such as the preferred barrier films of this invention, are materials that are comprised of components which, by microbial catalyzed degradation, are reduced in film or fiber strength by reduction in polymer size to monomers or short chains which are then assimilated by the microbes. In an aerobic environment, these monomers or short chains are ultimately oxidized to $CO_2$, $H_2O$, and new cell biomass. In an anaerobic environment the monomers or short chains are ultimately oxidized to $CO_2$, $H_2$, acetate, methane, and cell biomass. Successful biodegradation requires that direct physical contact must be established between the biodegradable material and the active microbial population or the enzymes produced by the active microbial population. An active microbial population useful for degrading the films and blends of the invention can generally be obtained from any municipal or industrial wastewater treatment facility in which the influents (waste stream) are high in cellulose materials. Moreover, successful biodegradation requires that certain minimal physical and chemical requirements be met such as suitable pH, temperature, oxygen concentration, proper nutrients, and moisture level. We have found that certain cellulose esters are biodegradable in conventional wastewater treatment facilities and in an in vitro enrichment system and hence are particularly useful in the preparation of blends to be used for barrier films and fibers in disposable articles. We have also found that many of the blends and AAPE degrade in a composting environment and hence are useful in the preparation of materials to be used as environmentally nonpersistent materials.

Additionally, the materials and fibers of the invention may be formed from a copolyester having a dicarboxylic acid component and a diol component where the copolyester contains repeat units of the following structures:

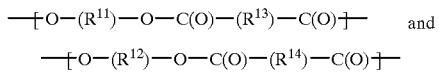

where $R^{11}$ and $R^{12}$ are selected from the group consisting of $C_2$–$C_{12}$ alkylene, $C_5$–$C_{10}$ cycloalkylene, $C_2$–$C_{12}$ oxyalkylene and mixtures thereof. $R^{11}$ and $R^{12}$ preferably comprise greater than 80 mole %, more preferably 100 mole % of the diol component. Generally, $R^{11}$ and $R^{12}$ contain at least 50 mole % of a diol component having either four or six carbon atoms, alone or in combination with another diol component. Preferably, the diol component is 1,4-butanediol or 1,6-hexanediol or a mixture thereof. Additionally, to better control the melting point of the polyesters of the invention, it is preferred that the diol component contain less than about 20 mole % of ethylene glycol or diethylene glycol. Furthermore, while the composition may contain a minor amount of ethylene glycol or diethylene glycol, it is more preferred that the amount of these glycols is less than 10 mole % and most preferably less than 6 mole % of the glycol component.

Other glycols which may be used include, but are not limited to, conventional glycols containing about 3 to about 12 carbon atoms. Suitable conventional glycols include, but are not limited to, propylene glycol, 1,3-propanediol, 1,5-pentanediol, neopentyl glycol, 2,2,4-trimethyl-1,3-propanediol, 2-ethyl-2-isobutyl-1,3-propanediol, 2,2,4,4-tetramethyl 1,3-cyclobutanediol, 2,4-dimethyl-2-ethyl-1,3-hexanediol, 2-ethyl-2-isobutyl-1,3-propanediol, 1,3-butanediol, 1,8-octanediol, 2,2,4-trimethyl-1,6-hexanediol, thiodiethanol, and 1,2-cyclohexanedimethanol, 1,3-cyclohexanedimethanol and 1,4-cyclohexanedimethanol. The cyclohexanedimethanol moieties may be present as the cis-, trans- or as a mixture of isomers. Small amounts of polymeric glycols such as poly(tetramethylene glycol) or poly(ethylene glycol) or mixtures thereof may also be used. In using such polymeric glycols, molecular weights ranging from about 150 to about 5000 are suitable.

The dicarboxylic acid component of the above formulas contains an aliphatic dicarboxylic acid $R^{13}$, and an aromatic or cycloaliphatic dicarboxylic acid component $R^{14}$. For the dicarboxylic acid, $R^{13}$ is selected from the group consisting of $C_0$–$C_{10}$ alkylene or $C_2$–$C_4$ oxyalkylene and mixtures thereof and $R^{14}$ is selected from the group consisting of $C_6$–$C_{12}$ aryl, $C_6$–$C_{12}$ cycloaliphatic and mixtures thereof.

Typically, the $R^{13}$ and $R^{14}$ dicarboxylic acid components are formed from acids, anhydrides, acid chlorides or esters of dicarboxylic acids. For example, $R^{14}$ may be formed from dicarboxylic acids containing from about 8 to about 14 carbon atoms, cycloaliphatic dicarboxylic acids having about 8 to about 14 carbon atoms or mixtures thereof. Preferably $R^{14}$ is formed from an acid or ester of terephthalic acid, naphthalenedicarboxylic acid, and 1,3- or 1,4-cyclohexanedicarboxylic acid.

It should be noted that any of the naphthalenedicarboxylic acid isomers or mixtures of isomers may be used with the 1,4-, 1,5-, 2,6- and 2,7-isomers being preferred with the 2,6-isomer being most preferred. The 1,3- or 1,4-cyclohexanedicarboxylic acid moieties may be as the cis-, trans- or cis/trans mixtures of isomers.

In the above formula, $R^{13}$ may be formed from aliphatic dicarboxylic acids containing from about 2 to about 12 carbon atoms and oxyalkylene dicarboxylic acids containing about 4 to about 6 carbon atoms or mixtures thereof. Preferably $R^{13}$ is formed from an acid or ester of succinic, glutaric, adipic, azelaic, sebacic, suberic and 1,12-dodecanedioic acid. Most preferably $R^{13}$ is formed from an acid or ester of adipic or glutaric acid.

Additionally, other dicarboxylic acids may be employed in the dicarboxylic acid component. The additional dicarboxylic acids, other than those described above, generally contain about 4 to about 40 carbon atoms, for example, an acid or ester of an aromatic, aliphatic or cycloaliphatic dicarboxylic acid. Suitable additional dicarboxylic acids or esters are described in U.S. Pat. Nos. 5,608,031 and 5,668,243, herein incorporated by reference in their entirety. Particularly preferred examples of additional dicarboxylic acid components include, but are not limited to, 1,4-cyclohexanediacetic acid, diphenyl-4,4'-dicarboxylic acid, and dimer acid. The additional dicarboxylic acid components may be added in amounts up to about 20 mole %, more preferably up to about 10 mole % of the dicarboxylic acid component.

In the above formulas, $R^{13}$ is generally present in an amount ranging from about 45 to about 95 mole % of the dicarboxylic acid component and $R^{14}$ is typically present in an amount ranging from about 5 to about 55 mole % of the dicarboxylic acid component. Preferably $R^{13}$ is present in an amount ranging from about 45 to about 65 mole % and more preferably about 50 to about 65 mole % of the dicarboxylic acid component. It is preferred that $R^{14}$ is present in an amount ranging from about 35 to about 55 mole % and more preferably about 35 to about 50 mole % of the dicarboxylic acid component. As described above, however, in one embodiment of the invention, $R^{13}$ is present in an amount of less than about 95 and greater than 60 mole % of the dicarboxylic acid component and $R^{14}$ is present in an amount greater than about 5 and less than 40 mole %, preferably ranging from less than 40 to about 25 mole % of the dicarboxylic acid component.

Amine Compounds

Additionally, it is also possible to form the polyesters and copolyesters of the invention in the presence of up to about 20 mole % of an amine compound. Suitable amine containing compounds, include, but are not limited to, aminoalcohols and diamines in an amount of up to about 20 mole % of the glycol component or amine compounds such as aminoacids and lactams in an amount of up to about 20 mole % of the dicarboxylic acid component. The presence of the aminoalcohols, aminoacids, diamines or lactams in the glycol and dicarboxylic acid components provides for the formation of polyesteramides. These polyesteramides possess good binder fiber properties and, in addition, have excellent dyeing characteristics. In particular, deeper dyeing may be achieved through the use of the polyesteramides as compared to unmodified polyethylene terephthalate having the same I.V.

Generally, aminoalcohols for the invention include, but are not limited to, 2-aminoethanol, N,N-diethyl-3-amino-1,2-propanediol and 4-aminomethylcyclohexanemethanol. Typical diamines include, but are not limited to, ethylenediamine, trimethylenediamine, tetramethylenediamine, pentamethylenediamine, hexamethylenediamine, octamethylenediamine, dodecamethylenediamine and 1,4-cyclohexane-bis-methylamine. Additionally, examples of suitable lactams include, but are not limited to, caprolactam, laurolactam and azacyclododecan-2-one.

Branching Agents

The polyesters of the invention may be linear or branched. By adding a branching agent to the reaction of the glycol component and dicarboxylic acid component, the melt strength of the resulting polyester may be increased. When using a branching agent, small amounts, typically less than about 2 mole %, of the conventional branching agents may be reacted with the glycol component and dicarboxylic acid component to form the inventive polyesters. Conventional branching agents include polyfunctional acids, anhydrides, alcohols and mixtures thereof. Examples of suitable branching agents, include, but are not limited to, trimellitic anhydride, pyromellitic dianhydride, glycerol, trimethylolpropane, pentaerythritol, 3-amino-1,2-propanediol, and 1,3-diamino-2-propanol.

Polyester Compositions with Polylactic Acid

Alternatively, the inventive materials, such as fibers, may be formed from at least two polyesters with the first polyester being polylactic acid and the second polyester composition formed from a dicarboxylic acid component and a diol component such that the second polyester contains repeat units of the following structures:

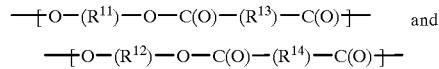

where $R^{11}$, $R^{12}$, $R^{13}$ and $R^{14}$ are defined above. Such a combination of polyesters provides good adhesive and bonding properties. Fibers formed from this polyester composition may be in the form of melt blown, spunbond, spun fibers and mixtures thereof. The fibers can be unicomponent or multicomponent fibers, such as multicomponent binder fibers. An example of a suitable fiber is a sheath/core fiber configuration where the core is polylactic acid and the sheath is formed from the second polyester. In sheath/core configurations, the inventive polyesters can be up to about 90% by weight of the total composition, however, it preferred that the polyester is all or part of the sheath which may be less than 50% of the total weight. Such fibers can be used to create a variety of products such as nonwovens, multilayered nonwovens, laminates and composites.

Reaction Process for Forming the Polyesters

In forming the polyesters of the invention, the reaction of the glycol component and the dicarboxylic acid component may be carried out using conventional polyester polymerization conditions. When preparing the polyesters by means of an ester interchange reaction, i.e., from the ester form of the dicarboxylic acid components, the reaction process may comprise two steps. In the first step, the glycol component and the dicarboxylic acid component, such as, for example, dimethyl terephthalate and dimethyl adipate, are reacted at elevated temperatures, typically, about 180° C. to about 280° C. and pressures ranging from about 0.0 to about 60 psig. Preferably, the temperature for the ester interchange reaction ranges from about 190° C. to about 240° C., more preferably about 190° C. to about 230° C. while the preferred pressure ranges from about 15 psig to about 40 psig. Thereafter, the reaction product can be heated under still higher temperatures and under reduced pressure to form polyester with the elimination of glycol, which is readily volatilized under these conditions and removed from the system. This second step, or polycondensation step, may be continued under higher vacuum and at a temperature which generally ranges from about 240° C. to about 290° C. Preferably the temperature ranges from about 245° C. to about 265° C., until a polyester having the desired degree of polymerization, determined by I.V., is obtained. In order to obtain polymers with excellent color, it is desirable to limit the final polycondensation temperature to a maximum of about 260° C. to 265° C. The polycondensation step may be conducted under reduced pressure which ranges from about 400 mm Hg (torr) to about 0.1 mm Hg (torr).

To ensure that the reaction of the glycol component and dicarboxylic acid component by an ester interchange reaction mechanism is driven to completion, it is preferred to employ a stoichiometric excess of glycol component (for example, about 1.05 to about 3 moles and more preferably about 1.1 to about 2.0 moles of glycol component to one mole dicarboxylic acid component). However, the ratio of glycol component to dicarboxylic acid component is generally determined by the design of the reactor in which the polymerization reaction process occurs.

The polyesters may be prepared by direct esterification, i.e., from the acid form of the dicarboxylic acid component. For example, polyesters may be produced by reacting at least one dicarboxylic acid selected from terephthalic acid, naphthalenedicarboxylic acid, and 1,3- or 1,4-cyclohexanedicarboxylic acid and/or one or more aliphatic dicarboxylic acids with the glycol components. The direct esterification is conducted at a pressure of from about 1 to about 200 pounds per square inch gauge pressure. To produce a low molecular weight, linear polyester product having an average degree of polymerization of from about 1.4 to about 10 it is preferred to employ a pressure of less than 100 psig. The temperatures employed during the direct esterification reaction typically range from about 180° C. to about 280° C., more preferably ranging from about 200° C. to about 260° C. This low molecular weight polymer may then be polymerized by a polycondensation reaction.

To ensure that the reaction of the glycol and dicarboxylic acid components by a direct esterification reaction mechanism is driven to completion, it is preferred to employ a stoichiometric excess of glycol component (for example, about 3.0 to 1.01 moles, more preferably 2.5 to 1.1 moles glycol component to one mole dicarboxylic acid component). However, the ratio of glycol component to dicarboxylic acid component will be determined by the design of the reactor in which the reaction process occurs.

The process of forming the polyesters of the invention may be conducted as a batch, semi-batch or continuous process. Advantageously the process is operated as a continuous process. Indeed, it is possible to produce superior coloration of the polyester when using a continuous process as the polyester may deteriorate in appearance if the polyester is allowed to reside in a reactor at an elevated temperature for too long a duration.

Catalyst System

A variety of catalyst systems are useful in promoting the reaction of the glycol component and the dicarboxylic acid component. Generally, it is preferred to employ a catalyst in the reaction as without the aid of a suitable catalyst, the polymerization reactions may not proceed at a satisfactory rate. Typically a catalyst system will contain catalytic materials and catalytic inhibitors.

Catalytic Materials

Catalytic materials which are suitable for the catalyst system include, but are not limited to, materials containing titanium, manganese, zinc, cobalt, antimony, gallium, lithium, calcium, silicon, and germanium. Such catalyst systems are described in U.S. Pat. Nos. 3,907,754, 3,962,189, 4,010,145, 4,356,299, 5,017,680, 5,668,243, and 5,681,918, herein incorporated by reference in their entirety. Generally, the catalyst system used to prepare the polyesters of the invention, comprises materials which contain titanium, manganese and/or zinc and mixtures thereof. While the amounts of the individual catalytic materials in the catalyst system will vary, it is desired that the total amount of catalytic materials in the catalyst system be below about 125 ppm, typically below about 100 ppm, preferably below about 80 ppm and most preferably below about 50 ppm. The "ppm" for the catalytic materials in the catalyst system and the catalytic inhibitor described below, refers to the weight of the element referred to and is based upon the weight of the final polyester product.

While titanium catalytic materials may be added in the form of complexed materials such as those described in U.S. Pat. No. 5,017,680, the titanium catalytic materials are suitably added in the form of an alkoxide in an amount ranging from about 1 to about 85 ppm, preferably about 3 to about 60 ppm and more preferably about 5 to about 45 ppm and most preferably up to about 35 ppm, for example about 8 to about 35 ppm. Indeed, copolyesters formed with lower levels of titanium catalytic materials have better stability when held in the melt. Suitable titanium alkoxides include, but are not limited to, acetyl triisopropyl titanate, tetraisopropyl titanate and tetraisobutyl titanate. Particularly preferred titanium catalytic materials include acetyl triisopropyl titanate and tetraisopropyl titanate. The titanium catalytic material may be added to the reaction process prior to direct esterification or ester interchange reaction or prior to the polycondensation reaction.

Manganese catalytic materials are typically added in the form of a salt, such as an organic acid salt in an amount ranging from about 0 to 70 ppm. When employing an ester interchange reaction it is preferred that the manganese is present in an amount of about 20 to about 70 ppm, more preferably about 30 to about 70 ppm and most preferably about 40 to about 70 ppm. Examples of suitable manganese catalyst salts include, but are not limited to, manganous benzoate tetrahydrate, manganese chloride, manganese oxide, manganese acetate, manganese acetylacetonate, and manganese succinate. Manganese is added to the reaction process prior to a direct esterification or ester interchange reaction.

Zinc may be added to the catalyst system in addition to the manganese or in place of the manganese catalyst. Zinc catalytic materials are typically added in the form of a salt in an amount ranging from 0 to 100 ppm, preferably about 25 to about 100 ppm and more preferably about 50 to about 80 ppm. Examples of suitable zinc compounds include, but are not limited to, zinc acetate, zinc succinate, and zinc alkoxide. Zinc is typically added to the reaction process prior to an ester interchange reaction.

If desired, a cobalt catalytic material, may also be employed as part of the catalyst system. When employed, cobalt is typically added in the form of a salt, such as an organic acid salt. Examples of suitable cobalt salts include, but are not limited to, cobaltous acetate trihydrate, cobaltous nitrate, cobaltous chloride, cobalt acetylacetonate, cobalt naphthenate, and cobalt salicylate. Cobalt may be added in an amount of up to about 100 ppm, more preferably up to about 90 ppm. As described below, the cobalt may function as both a catalytic material and as a colorant. As a colorant, cobalt is generally added to the reaction process after a direct esterification or ester interchange reaction. As cobalt is generally used as a colorant, the amount of cobalt is not considered when calculating the total amount of catalytic material.

In some embodiments antimony may be employed, however, it is preferred that the catalyst system not contain antimony. Indeed, in a preferred embodiment of the invention the copolyesters of the invention, and the fibers and binder fibers formed therefrom, do not contain any antimony catalytic materials. When used, however, suitable antimony compounds include, but are not limited to, antimonate esters of inorganic acids, antimony oxide, antimony alkoxides such as antimony isopropoxide, antimony halides, such as antimony chloride, antimony bromide and antimony fluoride, sodium or potassium antimonate, antimony carboxylates, such as antimony acetate and antimony glycolate or mixtures thereof. Preferably the antimony component is an antimony glycolate or an antimony oxide. Antimony is generally added after the ester interchange or a direct esterification reaction. When the copolyester is used to form binder fibers, antimony may be omitted from the catalyst system to avoid deposit buildup on the spinneret face caused by the presence of an antimony containing catalyst.

While less preferred, calcium, gallium and silicon catalytic materials may be used in the catalyst system. Examples of suitable calcium catalytic materials include, but are not limited to, calcium acetate, calcium glycoxide, and calcium phosphate monohydrate. Examples of suitable gallium catalytic materials include, but are not limited to, gallium chloride, gallium nitrate hydrate, gallium oxide, gallium lactate and gallium phosphide. Examples of suitable silicon catalytic materials include, but are not limited to, silicon acetate and tetraethyl orthosilicate. Germanium catalytic materials include, but are not limited to oxides, organic salts and in particular germanium glycolates.

A preferred esterification catalyst system for reacting dicarboxylic acid components with glycols contains titanium and optionally cobalt, catalytic materials. In the esterification catalyst system, the titanium is present in an amount ranging from about 1 to about 85 ppm, preferably about 3 to about 60 ppm, more preferably 5 to 45 ppm and most preferably up to about 35 ppm, for example about 8 to about 35 ppm. Additionally, in another embodiment of the esterification catalyst system, the total amount of catalytic materials in the catalyst system is less than or equal to about 125 ppm, preferably less than about 80 ppm, more preferably less than about 60 ppm and most preferably less than 45 ppm. A preferred esterification catalyst system is typically used in combination with a catalytic inhibitor comprising about 3 to about 90 ppm phosphorus; and a colorant in an effective amount, for example, about 2 to about 10 ppm of a blue and/or red substituted anthraquinone dye. Generally, the preferred esterification catalyst system is substantially free of zinc catalytic materials, more preferably contains less than 5 ppm zinc catalytic materials and most preferably is free of zinc catalytic materials. Additionally, when binder fibers are desired, the preferred esterification catalyst system is substantially free of antimony catalytic materials, more preferably contains less than 5 ppm antimony catalytic materials and most preferably is free of antimony catalytic materials.

Catalytic Inhibitor

To stabilize the effects of the catalyst system and to promote efficiency of zinc, manganese and cobalt catalytic materials, it is desirable to add a phosphorus catalytic inhibitor to the reaction process after an ester interchange or direct esterification reaction but prior to conducting the polycondensation reaction step. Typically, phosphorus is added in the form of a phosphate, such as phosphoric acid or an organic phosphate ester in an amount ranging from about 0 to 90 ppm and more preferably ranging from about 0 to 75 ppm. Typically lower amounts of phosphorus inhibitors are employed when using lower amounts of titanium catalysts in the catalyst system. Suitable phosphate esters for use in this invention include, but are not limited to, ethyl acid phosphate, diethyl acid phosphate, triethyl phosphate, arylalkyl phosphates and tris-2-ethylhexyl phosphate. One useful phosphate catalytic inhibitor is sold under the Merpol® A tradename which is commercially available from Du Pont de Nemours of Wilmington, Del.

Colorants

In forming the polyesters of the invention, colorants, sometimes referred to as toners, may be added to impart a desired neutral hue and/or brightness to the resulting polyester. This helps to offset any naturally occurring yellowness in the polyester. When colored polyesters are desired, pigments, whiteners or colorants may be added to the reaction mixture during the reaction of the glycol component and the dicarboxylic acid component or they may be melt blended with the preformed polyester. A preferred method of including colorants is to copolymerize a thermally stable organic colorant having reactive groups such that the colorant is incorporated into the polyester to improve the hue of the polyester. For example, colorants such as dyes possessing reactive hydroxyl and/or carboxyl groups, including, but not limited to, blue and red substituted anthraquinones, may be copolymerized into the polymer chain. Colorants and dyes are described in detail in U.S. Pat. Nos. 4,521,556, 4,740,581, 4,749,772, 4,749,773, 4,749,774, 4,950,732, 5,252,699, 5,384,377, 5,372,864, 5,340,910 and 5,681,918, herein incorporated by reference in their entirety. When dyes are employed as colorants, they may be added to the polyester reaction process after an ester interchange or direct esterification reaction. Furthermore, when a dye or dye mixture is employed as the toner colorant for the polyester, it is preferred that the total amount of dye is less than about 10 ppm. Additionally, in a preferred embodiment of the invention, the colorant is free of cobalt, i.e., the colorant employed produces the desired color in the absence of cobalt.

Alternatively, inorganic pigments, such as titanium dioxide and cobalt containing materials, may be added to the polyester reaction. Advantageously when a catalyst material contains cobalt, the cobalt may also act as a colorant. Care must be taken to control the level of cobalt in order to avoid opacity and dingy appearance in the polyesters of the invention. To control the level of opacity and dinginess, cobalt may be employed in an amount ranging up to about 90 ppm.

Preferred Copolyesters of the Invention

The copolyesters of the invention tend to possess good color and may accept dyes more easily than previous polyesters. Indeed, with the invention, semicrystalline or crystalline copolyester polymers may be formed and readily processed into fibers, such as binder fibers having excellent bonding properties. The copolyesters of the invention are capable of exhibiting excellent color and may accept dyes more easily than polyethylene terephthalate polyesters. Furthermore, these copolyesters are more easily dyed at lower temperatures and typically more easily printed.

The preferred copolyesters of the invention have an inherent viscosity, I.V., ranging from about 0.40 to about 1.80. Preferably these polyesters have an I.V. ranging from about 0.50 to about 1.55, and most preferably about 0.60 to about 1.40. The I.V. of the polyesters of the invention is determined by measuring the I.V. at 25° C. using 0.5 g polymer per 100 mL of a solvent consisting of 60% by weight phenol and 40% by weight tetrachloroethane. The basic method of determining the I.V. of a polyester is set forth in ASTM D-2857-95.

Generally, the selection of the glycol component and the dicarboxylic acid component may be controlled to form either crystalline or amorphous copolyesters with glass transition temperatures preferably lower than polyethylene terephthalate. In particular, it is preferred that the copolyesters of the invention are formed as semicrystalline or crystalline polyesters. Such copolyesters preferably have a melting point ranging from about 75° C. to about 160° C. It is most preferred that the semicrystalline or crystalline copolyesters have a fairly sharp melting point and melt at a temperature of less than 140° C., preferably about 105 to about 125° C. For example, by employing glycols having four or six carbon atoms, such as 1,4-butanediol or 1,6-hexanediol, it is possible to form the desired semicrystalline or crystalline polyesters and achieve superior control over its melting point.

One advantage of the copolyesters of the invention, with their controlled melting point, is their ability to bond to objects when activated by conventional means. The copolyesters of the invention, especially low I.V. copolyesters, are capable of bonding activation at lower temperatures and have improved melt flow at lower temperatures than typically modified amorphous copolyesters, as measured by the Kayeness instrument, which is similar to the Tinius Olsen Indexer. This improved melt flow may beneficially result in stronger bonds at lower temperatures or shorter exposures and allows for higher manufacturing speeds in the bonding activation step. The use of lower bonding temperatures aids in minimizing detrimental effects to higher melting point fibers when they are blended with the polyesters of the invention. For example, the use of lower bonding temperatures aids in the reduction of discoloration, shrinkage, loss of crimp and resiliency, change of tactile aesthetics, less volatilization and smoking of fiber finishes.

Another feature of the copolyesters is that when properly activated the copolyesters are capable of forming strong bonds with a wide range of polyesters as well as cellulosics (cotton, flax, pulp, cotton linter pulp, fluff pulp and wood fibers, rayons, lyocell, cellulose acetates and other natural and regenerated forms), plus other fibrous and film materials. The copolyesters of the invention can be melt spun into fibers, both staple and filament. The copolyesters are likewise suitable for use in conventional fabric or web/fabric forming extrusion processes such as spunbonding and melt blowing. As apparent, the elastic behavior of the copolyesters offers a wide variety of advantages for a number of applications and can be modified in processing steps such as spinning.

Products Formed from the Copolyesters of the Invention

The copolyesters of the invention may be used to form a variety of products. The polyesters of the invention may be used to form an article of manufacture or be used as an additive, such as a compounding additive concentrate or master batch for another polymer system. In addition, binder fibers and other articles may be formed with the cellulosics, polyesters or glass that include, but are not limited to, absorbent products, construction materials, preforms, composites, films and fibers. The inventive polyesters may be part of the articles to be formed or may form the entire article.

Conventional additives may be added to the polyesters of the invention, depending upon the desired end use of the polyester. Suitable additives for the polyesters are described in detail in U.S. Pat. Nos. 5,608,031 and 5,773,554 herein incorporated by reference in their entirety. Typical additives for the polyesters include pigments, antioxidants, stabilizers, nucleating agents, tougheners, flame retardants, delustrants, mold release agents, epoxy compounds, impact modifiers, adhesion promoters, plasticizers, conducting or antistatic agents, wetting agents, liquid repellent agents, antimicrobial agents, free radical stabilizers, other surface modifiers, lubricants, viscosity modifiers, flow agents, and other processing agents.

One preferred article of the invention is a fiber. The fibers of the invention may be prepared in any desired length known in the art and generally in the form of a continuous filament or staple fiber. Fibers may be made from the copolyesters of the invention through any conventional means available including, but not limited to, melt spinning into fibers or directly into fabrics, the latter including spunbond and melt blown nonwovens. Depending upon the end use, any desired denier may be formed with the fibers employing polyesters of the invention, including fibers having a denier value ranging from microdenier to about 300 denier, more particularly up to about 100, preferably up to about 75 denier, more preferably from about microdenier up to about 20 denier and most preferably about 1 to about 15 denier.

Fibers formed by melt extruding and spinning the inventive copolyesters are easier to dye and are deeper dyeing as compared to polyethylene terephthalate homopolymers when employing the same aqueous dyeing conditions. Indeed, dyeing of the inventive copolyesters to a deeper depth of shade is possible when employing similar dyeing conditions. Conversely, the same depths of shade can be achieved with lower dyeing costs as compared to the dyeing of polyethylene terephthalate homopolymers. Lower dyeing temperatures and energy costs may also be possible. When these fibers are formed into fabrics, they are also more readily printed compared to unmodified PET fabrics.

Fibers formed from the polyesters of the invention may possess higher elastic properties than polyethylene terephthalate polyester fibers as measured by ASTM D 1774-94. Because of this distinct property improvement, the fibers of the invention can create highly recoverable, elastic bonds in laminated, molded and other bonded structures. These elastic bonds are less susceptible to cracking, stress fissures and failing when subjected to repeated flexing. Accordingly, fibers formed from the inventive copolyesters, such as binder fibers, are generally capable of maintaining the shape, appearance and dimensional stability of a bonded product over time.

The inventive copolyesters may be used to form fibers including, but not limited to, melt blown, spunbond, various spun fibers and combinations thereof. Spun fibers include staple or continuous filaments. The fibers may be formed into any desired configuration known in the art. The polyesters of the invention are preferably in the form of binder fibers having the form, or incorporated into, a fibrous structure. A preferred binder fiber is a crystallizable binder fiber. A major advantage of binder fibers is that bonded products containing the binder fibers can be obtained by applying heat, microwave frequencies, radio frequencies, ultrasonic frequencies or other sealing band-width energies to a web or unbonded batting of filaments, with or without pressure. Upon activation, the polyester in the binder fiber softens and flows and upon cooling forms a solid bond with neighboring fibers. The binder fibers of the invention are particularly suited for bonding to cellulosic fibers, such as cotton, rayon, lyocell, acetate and pulp-based fibers, flax, scoured wool, polyester, acrylic, nylon, carbon and glass. Typically, the binder fibers formed with the polyesters of the invention will have deniers of about less than about 300, more particularly less than about 100, preferably less than about 75, and more preferably about 1.2 to about 15. However, it is understood that other fibrous forms such as melt blown webs, spunbonded materials or separatable, segmented spun fiber configurations may also have microdenier sizes. Furthermore, the fibers of the invention may be crimped, for example with a sawtooth, stuffer box or helical crimp.

The binder fibers of the invention may be in the form of unicomponent or bicomponent binder fibers or other multicomponent forms. For example, tricomponent fibers are also a possibility, utilizing a variety of polymers and polymer variants, sometimes with the intermediate layer being a tie-layer to promote interfacial adhesion. The tie-layer can be the polyester of the invention or blends of this polyester with other polymers. Similarly, the polyester of this invention can be used as a tie-layer in laminating and extrusion coating.

Multicomponent binder fibers, such as bicomponent binder fibers, may have a sheath/core, side by side, or other configuration known in the art. For example, shaped binder fibers may be formed with the cross-sectional legs capped with binder materials during extrusion. The process of preparing and bonding a low melting point bicomponent binder fiber is described in detail in U.S. Pat. No. 3,589,956, herein incorporated by reference in its entirety. A typical bicomponent fiber of the invention may contain about 10 to about 90 wt % of the polyesters of the invention. In a preferred bicomponent fiber of the invention, the polyesters of this invention will be present in amounts of about 10 to about 75 weight % of the bicomponent fiber. The other component may be from a wide range of other polymeric materials including, but not limited to, polyesters such as polyethylene terephthalate (PET), polytrimethylene terephthalate (PTT), polybutylene terephthalate (PBT), polycyclohexylenedimethylene terephthalate polyesters (PCT), polyethylene naphthalenedicarboxylate (PEN), and polylactic acid (PLA) based polymers or mixtures thereof. Bicomponent binder fibers may be blended with other fibers or used alone to make nonwoven fabrics and high loft battings having various properties. Generally, bicomponent binder fibers contain a polymer having a high melting point to ensure structural integrity during the bonding process and a lower melting or amorphous polymer to facilitate bonding. Sometimes, economics may dictate that a much less expensive core material be used. In select cases, both the sheath and core may be required to meet certain biodegradable or compostable requirements.

Fibers of this invention, particularly binder fibers, are readily blended with a wide range of other fibers and polymers and subsequently heat or energy activated to provide nonwoven fabrics having good integrity and strength. For example, other polymers in the blends may include, but are not limited to polyester, polyamide, polycarbonate, polyolefins, functionalized polyolefins, acrylic, nylon, glass, cellulosic (cotton, pulp-based fibers, cellulose ester fibers etc.) as well as other synthetic and natural polymers and fibers. The melt blends can be made in a variety of forms, such as films, molded objects, nonwovens, textile/industrial yarns and fabrics, composites, laminates or powders. Incorporation in nonwovens can also aid lamination to other fabrics, films and some metallic surfaces. The amount of binder fiber in a nonwoven blend will generally be in the range of about 5 to about 30 weight %, although amounts as little as 2 weight % can also be used. In some instances, fabrics are formed using 100% binder fibers.

Another fibrous structure which may be made with the polyesters of the invention is a fiber which is formed by melt blending less than about 50% of the polyester with a polyolefin or functionalized polyolefin or a polyester other than the polyester of the invention. When melt blending, suitable compatibilizers may be employed for their desired effects. The melt blended polyester/polyolefin may be spun as a fiber to form a fibrous structure. This melt blending allows polyolefins to be spun in a natural state and dyed in separate subsequent operations, something which cannot be satisfactorily achieved with unmodified polyolefins such as polypropylene and polyethylene.

An advantage of the invention is that fibers containing the polyesters of this invention are capable of possessing a deeper dyeability and enhanced printability compared to a fiber grade polyethylene terephthalate homopolymer. Indeed, when tested according to the AATCC Crockmeter Test, the fibers of the invention are capable of achieving the highest ratings for colorfastness. More particularly, the AATCC Crockmeter Test is a method designed to determine the amount of color transferred from the surface of a colored textile material to other surfaces by rubbing. It is applicable to textiles made from all fibers in the form of yarn or fabric whether dyed, printed or otherwise colored. The test procedures in principle involve rubbing a colored test specimen with white crock test cloth under controlled conditions. The color transferred to the white test cloth is assessed by a comparison with the Gray Scale for Staining or the Chromatic Transference Scale and a grade is assigned. When tested for colorfastness to crocking on a scale of 1.0 to 5.0 (5.0 being the best grade) using the AATCC Crockmeter Test Method 8-1981, the fibers of the invention are capable of achieving superior wet and dry crock ratings of from 4.0 to 5.0.

The polyesters may also be used as an additive in polyethylene terephthalate (PET), polytrimethylene terephthalate (PTT), polybutylene terephthalate (PBT), polyethylene naphthalenedicarboxylate (PEN), polycyclohexylenedimethylene terephthalate polyesters (PCT) or other polyesters to enhance fiber disperse dye uptake and make it deeper dyeable, thus improving the depth of color with the same amount of dye under the same conditions employed for dyeing polyesters other than those of the invention, for example a polyethylene terephthalate polymer. This technique can also improve printability as compared to a fiber grade polyethylene terephthalate homopolymer.

The fibrous structures of the invention are particularly useful for processing into a wide variety of nonwoven, textile and tufted forms which may be activated in many different ways, including dry and sometimes wet heat, as well as ultrasonic and radio frequency energy. They are also suitable for use in making a wide variety of products including, but not limited to, high loft battings, needlepunched fabrics, flat nonwovens, spunbonds, hydroentangled fabrics, stitch-bonded fabrics, wet-laid nonwovens and paper, woven and knitted fabrics, apparel, wipes, absorbent cores, coverstock, multilayer nonwovens, medical and agricultural fabrics, filter media, face masks, interlinings, bath mats, scatter rugs, cotton and polyester carpeting, cellulosic insulation, furniture and auto seating and upholstery, footwear, handwear, particle board, fiber board, fiberglass composites, ribbons, decorative yams and fabrics, and a wide variety of laminates and molded articles.

In addition to binder fibers, adhesive powders may be produced from the polyesters of this invention, suitable for the powder bonding of nonwovens and lining fabrics. Another suitable use for the polyesters of the invention is as a compounding carrier material. For example, the polyester of the invention may be mixed with additives, including colorants, optical brighteners and UV stabilizers, to form a concentrate or masterbatch where this polyester is a carrier material. This concentrate or masterbatch may be combined with another polymer in a later process to provide color, opacity, durability, flame retardancy or other beneficial properties. Polyesters of the invention will accept higher levels of additives, such as pigments, than polyethylene terephthalates of similar inherent viscosities. The polyester may be blended or mixed by any suitable technology known in the art.

The polyesters of the invention may also be blended with a wide range of other polymers as a component of the masterbatch but not the carrier material. Such other polymers include other polyesters, polyamides, cellulose esters, polycarbonates, polyolefins and the like. Such masterbatches may subsequently be blended with more of the same or different polymers to be used in fibers, molded articles, sheeting or films to alter or to enhance properties. Polyesters of the invention will accept high levels of additives, such as pigments. The polyesters may be blended or mixed by any suitable technology known in the art. Additionally, the polyesters of the invention may be in the form of an additive which is a melt blend of the inventive polyesters and a first polymer, wherein the additive when blended with a second polymer, which may be the same or different from the first polymer, is capable of forming a fiber. Thus, any fiber or article which contains, in whole or in part, the polyesters of the invention, is encompassed by this invention.

Optional Quenching Device for Extrusion of Fibers

The inventive copolyesters may be spun on many types of fiber spinning lines to form the fibers of the invention. On some equipment, however, the filaments can become fused immediately below the spinneret face. In such situations, it may be beneficial to more efficiently quench the fibers to reduce their tendency to fuse together. To aid in the quenching of filaments, a quenching fluid may be used to cool the molten filaments by more rapid heat transfer than obtained by air quenching methods.

Figure 6:
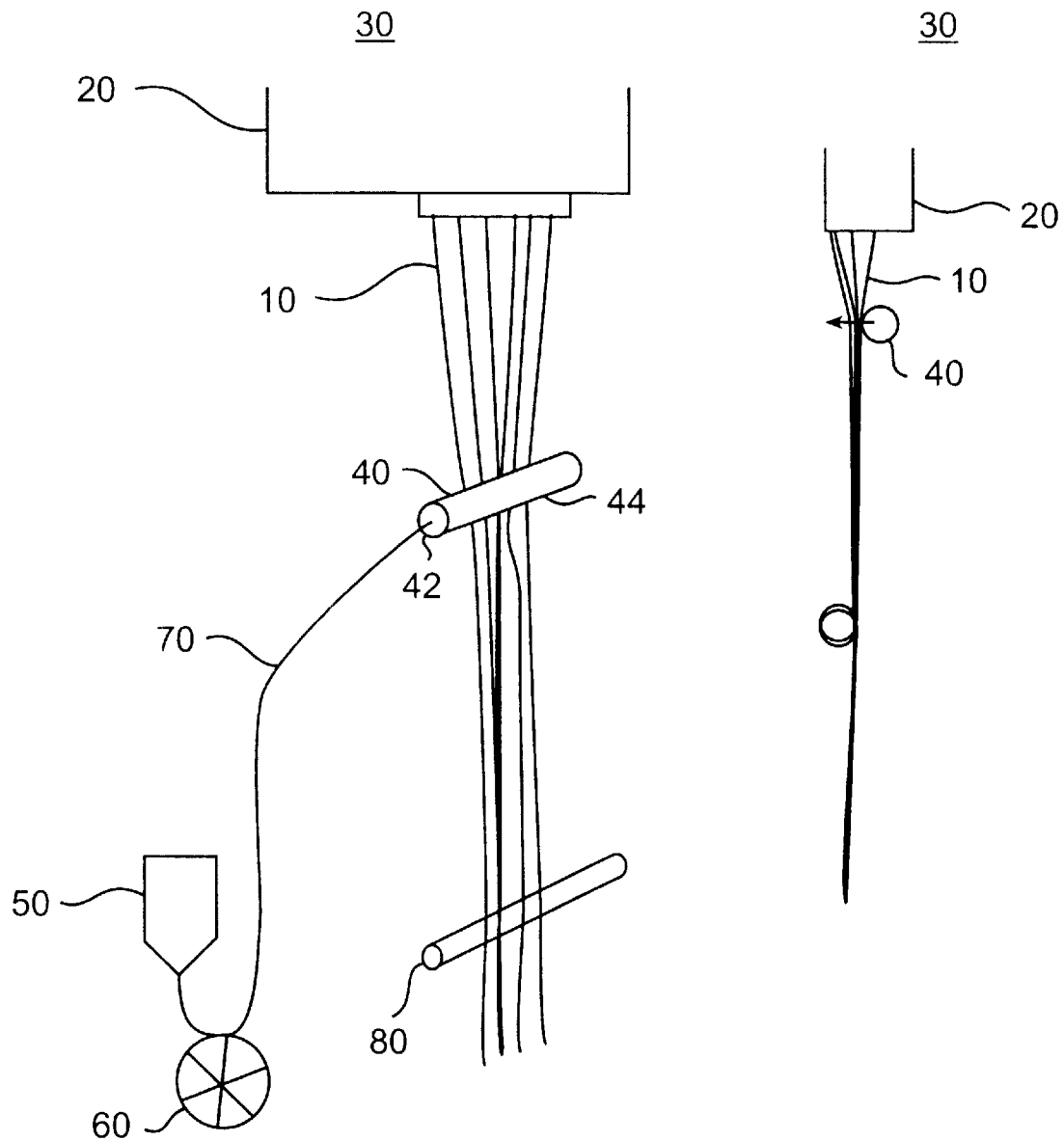
FIG. 6 Is a schematic of a preferred quenching device which may be used in the manufacture of fibers to overcome the fusing of filaments directly below a spinneret face.
Figure 7:
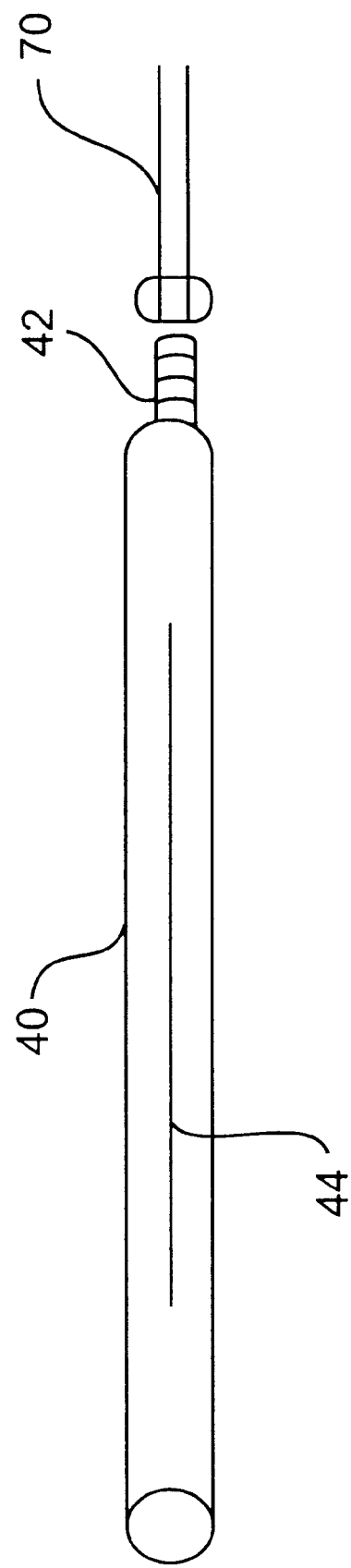
FIG. 7 Is a schematic of a preferred quenching device which may be used in the manufacture of fibers to overcome the fusing of filaments directly below a spinneret face.

One method of quenching fibers involves the use of the quenching device depicted in FIGS. 6 and 7. The use of such a quenching device in spin columns can aid in the formation of fibers, including but not limited to the inventive fibers discussed herein. The quenching device finds particular use in the melt extrusion processing of certain difficult to quench fibers which are tacky, amorphous or slow to solidify or cure by conventional air quenching methods during fiber spinning. It is also quite useful with polymers having low glass transition temperatures (Tg), especially with those having Tg values below 0° C. Furthermore, the quenching device is capable of preserving desired fiber cross-sections where faster quenching is required.

It is envisioned that difficult to quench fibers may be advantageously quenched through the use of the quenching device. Such difficult to quench fibers include, but are not limited to, polylactic acid (PLA) polymers, cellulose esters, polycaprolactone (PCL), other degradable polymers/copolymers, other copolyesters, low melting or amorphous polymers/copolymers derived from polyolefins, polyethers, polyamides (nylons) and the like. Polymer blends can also be spun into useful fibers with this improved quenching process. Such blends may include aliphatic-aromatic copolyester blends with cellulose esters, aliphatic copolyesters, polyvinyl alcohol/acetate, microcrystalline cellulose, starch derivatives and the like.

FIGS. 6 and 7 depict a preferred quenching device in a spinning column for making fibers. As depicted, filaments 10 can be extruded through extruder block 20 passing through a spinneret 30. The filaments 10 are then passed by a precision cut slot 44 in a quenching device 40 where they come into contact with a quenching fluid. The quenching device 40 contains a fluid inlet 42 which allows the quenching fluid to enter the tubular base and exit slot 44 such that the quenching fluid contacts the filaments. The filaments and the uniformly applied quenching fluid continue to move down the column at high speed. Slot 44 can be one long slit or a multitude of precision cut slits. In a preferred embodiment, the quenched filaments are kept in proximity to the quenching device through the use of a placement bar 80. To optimize the quenching process, the quenching device may be mounted such that the quenching device is capable of moving up or down, in or out or rotated. A particularly preferred quenching device is a 21 inch long, ¾ inch hollow steel tube with a 12 inch long, 0.067 mm width filament slot. Slot dimensions can be constant or change slightly along the slot length. Dimensions may also be different for different spinning column sizes or equipment.

As depicted in FIG. 6, the quenching fluid may be supplied from a quenching fluid source 50. From the fluid source 50, the quenching fluid may be pumped at a controlled rate using pump 60 through quenching line 70 into the quenching fluid inlet 42. In addition to FIGS. 6 and 7, other applicator designs are also possible.

The quenching fluid can be water or other suitable fluids such that the quenching fluid does not substantially dissolve the filaments. Furthermore, it is understood that the quenching fluid may contain suitable additives such as antistatic agents, lubricants, emulsifiers, etc. The presence of the additives may be used to enhance performance or reduce or eliminate downstream processing operations. In a preferred embodiment, the quenching fluid is room temperature demineralized water, although other temperatures may also be used to quench the filaments.

EXAMPLES

In the following examples, the blends were prepared by three general methods:
(i) the blend components are shaken together before compounding at the appropriate temperature a in a Rheometrics Mechanical Spectrometer. The resulting resin is typically ground to 5 mm particle size and a portion is pressed between two metal plates at a temperature above the melt temperature of the resin to form a melt pressed film;
(ii) blends of the cellulose esters and polyesters were prepared by compounding on a 30 mm Werner-Pfleiderer twin screw extruder. The typical procedure is as follows: Two separate feed systems, one for the cellulosic and one for the polyester were utilized for this method of melt blending. The cellulose ester was added as a dry powder in Zone 1 and the polyester was added as a viscous liquid in Zone 3. The cellulose ester was added at the desired rate using an AccuRate feeder through a hopper into the barrel of the extruder. The polyester was pre-heated under nitrogen and was poured into a heated feed tank. The polyester was maintained under a nitrogen atmosphere and gravity fed through a stainless steel line to a gear pump which transferred the molten material through a stainless steel line (½ inch outer diameter) into the barrel of the extruder. All lines for this feed system were heated and insulated. The production rate of the extruder is in the range of 10–50 pounds/hr. The zone temperatures are set depending on the exact nature of the polyester and the cellulose ester and generally vary in the range of about 100° C. to 250° C. Afterwards, the two strands of material exiting the extruder were quenched in water and chopped with a CONAIR JETRO pelletizer.

(iii) blends of the cellulose esters and polyesters were prepared by compounding on a 30 mm Werner-Pfleiderer twin screw extruder. The typical procedure is as follows: A single feed system was utilized for this method of melt blending. The cellulose ester and the polyester were dry blended and added as a solid in Zone 1. The dry blend was added at the desired rate using an AccuRate feeder through a hopper into the barrel of the extruder. The production rate of the extruder is in the range of 10–50 pounds/hr. The zone temperatures are set depending on the exact nature of the polyester and the cellulose ester and generally vary in the range of about 100° C. to 250° C. Afterwards, the two strands of material exiting the extruder were quenched in water and chopped with a CONAIR JETRO pelletizer.

The tensile strength, break to elongation, and tangent modulus of the films are measured by ASTM method D882; the tear force is measured by ASTM method D1938; the oxygen and water vapor transmission rates are measured by ASTM methods D3985 and F372, respectively. The tensile strength and elongation at break for molded pieces are measured by ASTM method D638; the flexural strength and modulus by ASTM method D790; the Izod impact strength by ASTM method D256; the heat deflection temperature by ASTM method D648. Inherent viscosities are measured at a temperature of 25° C. for a 0.5 gram sample in 100 ml of a 60/40 by weight solution of phenol/tetrachloroethane. Dynamic mechanical thermal analysis (DMTA) spectra were collected using a Polymer Laboratories Mk II at 4° C./min and 1 Hz.

Abbreviations used herein are as follows: "I.V." is inherent viscosity; "g" is gram; "psi" is pounds per square inch; "cc" is cubic centimeter; "m" is meter; "rpm" is revolutions per minute; "DSPr" is degree of substitution per anhydroglucose unit for propionyl; "DSAc" is degree of substitution per anhydroglucose unit for acetyl; "DSBu" is degree of substitution per anhydroglucose unit for butyryl; "BOD" is biochemical oxygen demand; "vol." or "v" is volume; "wt." is weight; "mm" is millimeter; "NaOAc" is sodium acetate; "nm" is not measured; "CE" is cellulose ester; "PE" is polyester; "DOA" is dioctyl adipate; "HDT" is heat deflection temperature; "WVTR" is water vapor transmission rate; "mil" is 0.001 inch. Relative to the clarity of the films, "+" indicates a transparent film characteristic of a miscible blend; "±" indicates a hazy film characteristic of a partially miscible film; "−" indicates an opaque film characteristic of an immiscible blend; "AAPE" is aliphatic-aromatic copolyester and, as used herein, refers to the copolyesters where blending is not required. Relative to naming of the cellulose ester, "CAP" is cellulose acetate propionate; "CA" is cellulose acetate; "CAB" is cellulose acetate butyrate. Relative to naming of the polyester, representative examples are: "PTS (T) [85/15]" is poly(tetramethylene succinate-co-terephthalate) where the mole percent of succinate to terephthalate is 85/15; "PTA(T) [85/15]" is poly(tetramethylene adipate-co-terephthalate) where the mole percent of adipate to terephthalate is 85/15; "PTG (T) [85/15]" is poly(tetramethylene glutarate-co-terephthalate) where the mole percent of glutarate to terephthalate is 85/15; "PTG(T)(D) [60/35/5]" is poly(tetramethylene glutarate-co-terephthalate-co-diglycolate) where the mole percent of glutarate to terephthalate to diglycolate is 60/35/5; "PTG(N) [85/15]" is poly(tetramethylene glutarate-co-naphthalate) where the mole percent of glutarate to naphthalate is 85/15; "PES" is poly(ethylene succinate); "PHS" is poly (hexamethylene succinate); "PEG" is poly (ethylene glutarate); "PTG" is poly (tetramethylene glutarate); "PHG" is poly (hexamethylene glutarate); "PT (E) G [50/50]" is poly (tetramethylene-co-ethylene glutarate) where the mole % of tetramethylene to ethylene is 50/50; "PEA" is poly (ethylene adipate); "PDEA" is poly(diethylene adipate); "PHA" is poly(hexamethylene adipate). Other abbreviations are: "TEGDA" is triethylene glycol diacetate; "PVA" is poly(vinyl acetate); "PMMA" is poly(methyl methacrylate); "PEMA" is poly(ethyl methacrylate). MYVAPLEX 600 is the trade name for concentrated glyceryl monostearates and is available from Eastman Chemical Company. MYVAPLEX concentrated glyceryl monostearate is a 90% minimum distilled monoglyceride produced from hydrogenated soybean oil which is composed primarily of stearic acid esters. MYVACET is the trade name for distilled acetylated monoglycerides of modified fats. The per cent acetylation of MYVACET 507 ranges from 48.5 to 51.5; the percent acetylation of MYVACET 707 ranges from 66.5 to 69.5; the percent acetylation of MYVACET 908 is a minimum of 96, MYVEROL is the trade name for concentrated glyceryl monostearates and is available from Eastman Chemical Company. MYVEROL is very similar to MYVAPLEX except that the distilled monoglyceride is produced from different fat sources.

Example 1

Blends of cellulose acetate propionate ($DS_{Ac}$=0.10, $DS_{Pr}$=2.64, IV=1.3) and aliphatic-aromatic copolyesters and films made from the blends were prepared using the standard procedures. Glass transition temperature were measured by DMTA and were calculated using the Fox-Flory equation. The results are given in Tables I and II.

TABLE I

Tg, I.V., and Clarity of CAP/Aliphatic-Aromatic Copolyester Blends

| Entry | Polyester | Tg (exp) °C. | Tg (cal) °C. | I.V. PE | I.V. Blend | Clarity |
|---|---|---|---|---|---|---|
| 1 | 20% PTS(T) [85/15] | 124 | 110 | 1.0 | 1.1 | + |
| 2 | 40% PTS(T) [85/15] | 93 | 75 | 1.0 | 1.1 | + |
| 3 | 20% PTA(T) [85/15] | 125 | 110 | 0.7 | 1.0 | + |
| 4 | 40% PTA(T) [85/15] | 87 | 76 | 0.7 | 0.9 | + |
| 5 | 20% PEG(T) [85/15] | 139 | 110 | 0.6 | 0.9 | + |
| 6 | 40% PEG(T) [85/15] | 75 | 78 | 0.6 | 1.0 | + |
| 7 | 10% PEG(T) [70/30] | 146 | 143 | 0.9 | 1.0 | + |
| 8 | 20% PEG(T) [70/30] | 136 | 113 | 0.9 | 1.0 | + |
| 9 | 30% PEG(T) [70/30] | 126* | 97 | 0.9 | 1.0 | + |
| 10 | 40% PEG(T) [70/30] | 82 | 83 | 0.6 | 1.0 | + |
| 11 | 55% PEG(T) [70/30] | 62 | 59 | 0.6 | 0.9 | + |
| 12 | 70% PEG(T) [70/30] | 25, 85, 98 | 34 | 0.9 | 0.9 | + |
| 13 | 40% PTG(T) [95/5] | 93 | 66 | 1.2 | nm | + |
| 14 | 20% PTG(T) [90/10] | 127 | 105 | 0.9 | nm | + |
| 15 | 40% PTG(T) [90/10] | 88 | 65 | 0.9 | 1.0 | + |
| 16 | 40% PT(E)G(T) [50/50, 85/15] | 71 | 72 | 0.7 | 1.0 | + |
| 17 | 20% PT(E)G(T) [50/50, 70/30] | 125 | 110 | 0.7 | 1.0 | + |
| 18 | 40% PT(E)G(T) [50/50, 70/30] | 76 | 77 | 0.7 | 1.0 | + |
| 19 | 40% PTG(T) [85/15] | 75 | 71 | 0.7 | 1.0 | + |
| 20 | 20% PTG(T) [70/30] | 135 | 110 | 0.7 | 1.0 | + |
| 21 | 40% PTG(T) [70/30] | 82 | 73 | 0.7 | 1.0 | + |
| 22 | 20% PTG(T) [60/40] | 143 | 113 | 1.5 | 1.1 | + |
| 23 | 40% PTG(T) [60/40] | 130* | 78 | 1.5 | 1.2 | + |
| 24 | 60% PTG(T) [60/40] | 3, 76, 112 | 43 | 1.5 | 1.0 | ± |
| 25 | 70% PTG(T) [60/40] | 2, 108 | 26 | 1.5 | 1.2 | ± |
| 26 | 80% PTG(T) [60/40] | 5 | 9 | 1.5 | 0.9 | ± |
| 27 | 20% PHG(T) [80/20] | 143 | 106 | 1.2 | 1.2 | + |
| 28 | 40% PHG(T) [80/20] | 105* | 66 | 0.7 | 0.9 | + |
| 29 | 20% PEG(N) [85/15] | 138 | 111 | 0.8 | 1.0 | + |
| 30 | 40% PEG(N) [85/15] | 102* | 77 | 0.8 | 0.9 | + |

*Broad transitions with shoulders

TABLE II

Mechanical Properties, Tear Strength, and Water Vapor Transmission Rates
Of Cellulose Ester/Aliphatic-aromatic Copolyester Blends

| Sample | Polyester | | Elongation at Break (%) | Tangent Modulus ($10^5$ psi) | Tensile Strength ($10^3$ psi) | Tear Strength (g/mil) | WVTR (g mil/100) in$^2$-24 hours |
|---|---|---|---|---|---|---|---|
| 1 | 20% | PTS(T)] | [85/15 | 8 | 2.11 | 5.97 | 14.8 | 222 |
| 2 | 40% | PTS(T) | [85/15] | 82 | 0.22 | 2.83 | 14.7 | 173 |
| 3 | 20% | PTA(T) | [85/15] | 6 | 1.86 | 5.03 | 12.0 | nm |
| 4 | 40% | PTA(T) | [85/15] | 61 | 0.19 | 1.62 | 10.3 | nm |
| 5 | 20% | PEG(T) | [85/15] | 4 | 2.21 | 6.11 | 8.0 | nm |
| 6 | 40% | PEG(T) | [85/15] | 91 | 0.31 | 2.89 | 14.4 | 253 |
| 7 | 10% | PEG(T) | [70/30] | 3 | 2.21 | 4.90 | 10.0 | 172 |
| 8 | 20% | PEG(T) | [70/30] | 4 | 2.21 | 6.29 | 7.5 | 216 |
| 9 | 30% | PEG(T) | [70/30] | 18 | 1.35 | 4.24 | 11.5 | 184 |
| 10 | 40% | PEG(T) | [70/30] | 47 | 0.59 | 2.83 | 10.9 | 145 |
| 11 | 55% | PEG(T) | [70/30] | 54 | 0.06 | 1.16 | 12.6 | 272 |
| 12 | 70% | PEG(T) | [70/30] | 114 | 0.02 | 0.42 | 25.8 | nm |
| 13 | 40% | PTG(T) | [95/5] | 75 | 0.10 | 1.70 | 9.3 | nm |
| 14 | 20% | PTG(T) | [90/10] | 21 | 1.78 | 5.33 | 11.4 | nm |
| 15 | 40% | PTG(T) | [90/10] | 77 | 0.12 | 2.02 | 9.9 | nm |
| 16 | 40% | PT(E)G(T) | [50/50, 85/15] | 81 | 0.27 | 2.58 | 14.1 | 216 |
| 17 | 20% | PT(E)G(T) | [50/50, 70/30] | 3 | 2.15 | 5.58 | 7.2 | nm |
| 18 | 40% | PT(E)G(T) | [50/50, 70/30] | 61 | 0.43 | 2.81 | 13.7 | 175 |
| 19 | 40% | PTG(T) | [85/15] | 83 | 0.24 | 2.48 | 11.5 | 246 |
| 20 | 20% | PTG(T) | [70/30] | 5 | 1.23 | 6.26 | 12.4 | 188 |
| 21 | 40% | PTG(T) | [70/30] | 50 | 0.37 | 2.05 | 16.3 | 238 |
| 22 | 20% | PTG(T) | [60/40] | 8 | 1.13 | 3.47 | 20.2 | 364 |
| 23 | 40% | PTG(T) | [60/40] | 82 | 0.99 | 4.01 | 23.6 | 275 |
| 24 | 60% | PTG(T) | [60/40] | 72 | 0.28 | 1.89 | 14.9 | nm |
| 25 | 70% | PTG(T) | [60/40] | 63 | 0.21 | 1.32 | 19.1 | nm |
| 26 | 80% | PTG(T) | [60/40] | 207 | 0.09 | 1.11 | 59.2 | nm |
| 27 | 20% | PHG(T) | [80/20] | 30 | 1.5 | 4.87 | 4.6 | nm |
| 28 | 40% | PHG(T) | [80/20] | 45 | 0.25 | 1.35 | 10.5 | nm |
| 29 | 20% | PEG(N) | [85/15] | 12 | 2.14 | 6.05 | 11.1 | 175 |
| 30 | 40% | PEG(N) | [85/15] | 69 | 0.38 | 2.66 | 14.4 | 308 |

The I.V. data from Table I illustrates that the molecular weight of the blend components are preserved in the blending process. As the clarity indicates, the films were transparent which is characteristic of miscible blends.

Table I demonstrates that each of the blends involving 20% aliphatic-aromatic copolyester (entries 1, 3, 5, 8, 14, 17, 20, 22, 27, and 29) had an experimental $Tg_{12}$ which was 14° to 37° C. higher than the $Tg_{12}$ calculated for each blend. The 40% aliphatic-aromatic copolyester blends involving a C4 diacid (entry 2), a C6 diacid (entry 4), or a C10 aromatic diacid (entry 30) also showed a 18, 11, and 25° C., respectively, positive deviation of the experimental $Tg_{12}$ from the theoretical $Tg_{12}$. Within the family of 40% aliphatic-aromatic copolyester involving a C5 aliphatic diacid, the experimental $Tg_{12}$ of entries 6, 10, 16, 19, and 21 (15–30% C6 aromatic diacid) showed good agreement with the theoretical $Tg_{12}$ (±10° C.). In contrast, the experimental $Tg_{12}$'s of the 40% PTG(T) blends containing 5, 10, and 40% C6 aromatic diacid showed a 27, 23, and 52° C., respectively, positive deviation from the calculated value. In the series of 10–70% PEG(T) [70/30] (entries 7–12), the 10–30% blends showed a positive deviation of the experimental T12 from the calculated values, the 40–55% blends had $Tg_{12}$'s which showed excellent agreement with the calculated $Tg_{12}$'s, and the 70% blend showed multiple Tg's characteristic of a partially miscible blend. In contrast, the series of 20–70% PTG(T) [60/40] blends (entries 22–25) either had multiple $Tg_{12}$'s or Tg12's that were quite different from theoretical. At very high levels of aliphatic-aromatic copolyester (cf. entry 26), single Tg's were observed. Analysis of this type suggests that blends of cellulose esters with aliphatic-aromatic copolyester involving a C5 aliphatic diacid are generally miscible in approximately the 30–55% range when the aromatic portion of the copolyesters is approximately 15–30%. Aliphatic-aromatic copolyester blends involving a C5 aliphatic diacid outside of the 30–55% range exhibit varying levels of miscibilities. Blends involving other aliphatic diacids also exhibit varying levels of miscibilities through a wider range.

Blend miscibility is also strongly dependent upon the molecular weight of the polyester. In general, a low I.V. polyester will give a wider window of miscibility.

Cellulose esters typically have high WVTR (>500 g mil/100 in$^2$-24 h). As Table II shows, all of the CAP/aliphatic-aromatic copolyester blends have WVTR less than 500 g mil/100 in$^2$-24 h. Table II also demonstrates that a wide range of physical properties for materials prepared from the blends are possible depending upon the blend components and blend composition. Many of the aliphatic-aromatic copolyester blends gave unexpected and unusual physical properties. For example, the tangent modulus (Table II) for the 20% blends were, for the most part, surprisingly high relative to the CAP ($2.1\times10^5$ psi). With the exception of the blends involving PTG(T) [70/30] and PTG(T) [60/40], the tangent moduli all remained above $1.5\times10^5$ psi. Even more surprising was the tensile strength for the 20% blends. With the exception of the PTG(T) [60/40] blend, the tensile strength of these blends were all above $5.0\times10^3$ psi; in some cases the tensile strength was improved relative to the CAP ($5.5\times10^3$). In general, with the exception of the PTG(T) [60/40] blends, all of the blends involving 20% aliphatic-aromatic copolyester behaved very similar to the blend major component, cellulose acetate propionate. In effect, we were able to substitute 20% of a copolyester, which generally has much different physical properties than the cellulose ester blend component, for cellulose ester without lowering, and in some case improving, the mechanical properties inherent to the cellulose acetate propionate.

Example 2

Blends of cellulose esters and succinate polyesters and films therefrom were prepared using the standard procedures. The results are given in Tables III and IV.

TABLE III

DS/AGU, I.V., and Clarity of Cellulose Ester/Polyester Blends: C4 Diacids

| Entry | Polyester | $DS_{Ac}$ | $DS_{Pr}$ | $DS_{Bu}$ | I.V. CE | I.V. PE | I.V. Blend | Clarity |
|---|---|---|---|---|---|---|---|---|
| 31 | 10% PES | 2.50 | — | — | 1.2 | 1.0 | 1.25 | + |
| 32 | 20% PES | 2.50 | — | — | 1.2 | 1.0 | 1.18 | + |
| 33 | 20% PES | 0.10 | 2.64 | — | 1.3 | 1.1 | 1.18 | + |
| 34 | 40% PES | 0.10 | 2.64 | — | 1.3 | 1.0 | 1.11 | + |
| 35 | 20% PHS | 0.10 | 2.64 | — | 1.3 | 1.0 | 1.16 | + |
| 36 | 40% PHS | 0.10 | 2.64 | — | 1.3 | 1.0 | 1.11 | + |

TABLE IV

Mechanical Properties and Tear Strength of Films Prepared From Cellulose Ester/Polyester Blends: C4 Diacids

| Entry | Polyester | Elongation at Break | Tangent Modulus ($10^5$ psi) | Tensile Strength ($10^3$ psi) | Tear Strength (g/mil) |
|---|---|---|---|---|---|
| 31 | 10% PES | Nm | nm | Nm | nm |
| 32 | 20% PES | Nm | nm | Nm | nm |
| 33 | 20% PES | 11 | 1.92 | 5.45 | nm |
| 34 | 40% PES | 48 | 0.71 | 2.97 | nm |
| 35 | 20% PHS | 36 | 1.70 | 4.68 | nm |
| 36 | 40% PHS | 87 | 0.26 | 2.32 | 12.2 |

The I.V. data from Table III illustrates that the molecular weight of the blend components are preserved in the blending process. As the clarity indicates, the films were transparent which is characteristic of miscible blends. Furthermore, the Tg of the blend was measured for representative samples. Entries 34 and 36 had a single Tg of 80° C. and 70° C., respectively. A single Tg is also characteristic of miscible blends. As Table IV demonstrates, a very wide range of physical properties for materials prepared from the blends are possible by proper selection of the blend composition.

Example 3

Blends of cellulose esters and glutarate polyesters and films therefrom were prepared using the standard procedures. The results are given in Tables V and VI.

TABLE V

DS/AGU, I.V., and Clarity of Cellulose Ester/Polyester Blends: C5 Diacids

| Entry | Polyester | $DS_{Ac}$ | $DS_{Pr}$ | $DS_{Bu}$ | I.V. CE | I.V. PE | I.V. Blend | Clarity |
|---|---|---|---|---|---|---|---|---|
| 37 | 50% PEG | 2.50 | — | — | 1.2 | — | Nm | + |
| 38 | 20% PEG | 0.10 | 2.64 | — | 1.3 | 1.2 | 1.21 | + |
| 39 | 40% PEG | 0.10 | 2.64 | — | 1.3 | 1.2 | 1.19 | + |
| 40 | 35% PEG | 0.34 | 2.15 | — | 1.6 | 0.9 | Nm | + |
| 41 | 40% PEG | 0.34 | 2.15 | — | 1.6 | 0.9 | Nm | + |
| 42 | 45% PEG | 0.34 | 2.15 | — | 1.6 | 0.9 | Nm | + |
| 43 | 35% PEG | 0.12 | 2.14 | — | 1.3 | 1.1 | Nm | + |
| 44 | 40% PEG | 0.12 | 2.14 | — | 1.3 | 0.9 | Nm | + |
| 45 | 35% PEG | 0.11 | 2.05 | — | 1.6 | 0.9 | Nm | + |
| 46 | 40% PEG | 0.11 | 2.05 | — | 1.6 | 0.9 | Nm | + |
| 47 | 45% PEG | 0.11 | 2.05 | — | 1.6 | 0.9 | Nm | + |
| 48 | 20% PDEG | 0.10 | 2.64 | — | 1.3 | 1.1 | 1.21 | + |
| 49 | 40% PDEG | 0.10 | 2.64 | — | 1.3 | 1.1 | Nm | + |
| 50 | 40% PT(E)G [50,50] | 0.10 | 2.64 | — | 1.3 | 0.7 | Nm | + |
| 51 | 10% PTG | 0.10 | 2.64 | — | 1.3 | 0.5 | 1.20 | + |
| 52 | 20% PTG | 0.10 | 2.64 | — | 1.3 | 0.5 | 1.21 | + |
| 53 | 30% PTG | 0.10 | 2.64 | — | 1.3 | 0.6 | 1.07 | + |
| 54 | 35% PTG | 0.10 | 2.64 | — | 1.3 | 0.5 | 1.07 | + |
| 55 | 40% PTG | 0.10 | 2.64 | — | 1.3 | 0.5 | 1.11 | + |
| 56 | 40% PTG | 0.10 | 2.64 | — | 1.3 | 0.6 | 1.06 | + |
| 57 | 40% PTG | 0.10 | 2.64 | — | 1.3 | 1.1 | Nm | + |
| 58 | 20% PTG | 0.10 | 2.64 | — | 1.3 | 1.7 | 1.25 | + |
| 59 | 25% PTG | 0.10 | 2.64 | — | 1.3 | 1.7 | 1.27 | + |
| 60 | 30% PTG | 0.10 | 2.64 | — | 1.3 | 1.7 | 1.25 | + |
| 61 | 35% PTG | 0.10 | 2.64 | — | 1.3 | 1.7 | 1.25 | + |
| 62 | 40% PTG | 0.10 | 2.64 | — | 1.3 | 1.7 | 1.31 | + |
| 63 | 50% PTG | 0.10 | 2.64 | — | 1.3 | 1.7 | 1.30 | + |
| 64 | 40% PTG | 0.17 | 2.29 | — | 1.7 | 1.1 | Nm | + |
| 65 | 40% PTG | 0.04 | 2.28 | — | 1.6 | 1.7 | Nm | + |
| 66 | 40% PTG | 0.34 | 2.15 | — | 1.6 | 1.1 | Nm | + |
| 67 | 35% PTG | 0.34 | 2.15 | — | 1.6 | 1.1 | Nm | + |
| 68 | 40% PTG | 0.10 | 2.16 | — | 1.0 | 1.1 | Nm | + |
| 69 | 40% PTG | 0.12 | 2.14 | — | 1.3 | 1.1 | Nm | + |
| 70 | 35% PTG | 0.11 | 2.05 | — | 1.6 | 1.1 | Nm | + |
| 71 | 40% PTG | 0.11 | 2.05 | — | 1.6 | 1.1 | Nm | + |
| 72 | 45% PTG | 0.11 | 2.05 | — | 1.6 | 1.1 | Nm | + |

TABLE V-continued

DS/AGU, I.V., and Clarity of Cellulose Ester/Polyester Blends: C5 Diacids

| Entry | Polyester | $DS_{Ac}$ | $DS_{Pr}$ | $DS_{Bu}$ | I.V. CE | I.V. PE | I.V. Blend | Clarity |
|---|---|---|---|---|---|---|---|---|
| 73 | 30% PHG | 0.10 | 2.64 | — | 1.3 | 0.5 | 1.06 | + |
| 74 | 40% PHG | 0.10 | 2.64 | — | 1.3 | 0.5 | 0.99 | + |
| 75 | 35% PTG | 1.01 | — | 1.67 | 1.2 | — | Nm | + |
| 76 | 40% PTG | 2.04 | — | 0.70 | 1.2 | — | Nm | + |

TABLE VI

Mechanical Properties and Tear Strength for Films Prepared From Cellulose Ester/Aliphatic Polyester Blends: C5 Diacids

| Entry | Polyester | Elongation at Break (%) | Tangent Modulus ($10^5$ psi) | Tensile Strength ($10^3$ psi) | Tear Strength (g/mil) |
|---|---|---|---|---|---|
| 37 | 50% PEG | nm | Nm | nm | nm |
| 38 | 20% PEG | 30 | 1.60 | 4.79 | nm |
| 39 | 40% PEG | 95 | 0.24 | 2.49 | 13.3 |
| 40 | 35% PEG | 80 | 0.52 | 3.44 | 18.5 |
| 41 | 40% PEG | 84 | 0.33 | 2.78 | 10.0 |
| 42 | 45% PEG | 104 | 0.21 | 2.56 | 15.9 |
| 43 | 35% PEG | 33 | 0.38 | 1.80 | 12.6 |
| 44 | 40% PEG | 19 | 0.24 | 1.07 | 9.8 |
| 45 | 35% PEG | 51 | 0.48 | 3.04 | 13.3 |
| 46 | 40% PEG | 86 | 0.32 | 2.80 | 10.4 |
| 47 | 45% PEG | 77 | 0.20 | 1.61 | 12.7 |
| 48 | 20% PDEG | 24 | 1.41 | 3.54 | 5.1 |
| 49 | 40% PDEG | 60 | 0.14 | 1.08 | 19.8 |
| 50 | 40% PT(E)G [50,50] | 76 | 0.15 | 1.73 | 9.1 |
| 51 | 10% PTG | 30 | 1.70 | 5.49 | 12.7 |
| 52 | 20% PTG | 43 | 1.20 | 3.72 | nm |
| 53 | 20% PTG | 65 | 0.73 | 2.97 | 16.7 |
| 54 | 35% PTG | 88 | 0.25 | 2.54 | 14.9 |
| 55 | 40% PTG | 53 | 0.15 | 1.18 | 11.8 |
| 56 | 40% PTG | 61 | 0.13 | 1.26 | 12.4 |
| 57 | 40% PTG | 71 | 0.12 | 1.59 | 13.3 |
| 58 | 20% | 18 | 1.68 | 4.64 | 12.5 |
| 59 | 25% | 67 | 1.27 | 4.41 | 18.7 |
| 60 | 30% | 69 | 0.96 | 3.31 | 21.5 |
| 61 | 35% | 72 | 0.45 | 2.36 | 22.9 |
| 62 | 40% | 128 | 0.13 | 2.68 | 18.0 |
| 63 | 50% | 117 | 0.05 | 2.14 | 23.0 |
| 64 | 40% | 113 | 0.22 | 2.67 | 15.8 |
| 65 | 40% | 42 | 0.21 | 1.29 | nm |
| 66 | 40% | 97 | 0.27 | 2.50 | 19.9 |
| 67 | 35% | 92 | 0.59 | 3.94 | 19.8 |
| 68 | 40% | 37 | 0.16 | 1.09 | 12.2 |
| 69 | 40% PTG | 36 | 0.22 | 1.27 | 15.4 |
| 70 | 35% PTG | 54 | 0.43 | 2.45 | 12.8 |
| 71 | 40% PTG | 53 | 0.26 | 1.97 | 12.9 |
| 72 | 45% PTG | 47 | 0.19 | 1.32 | 9.3 |
| 73 | 30% PTG | 57 | 0.68 | 2.43 | 17.4 |
| 74 | 40% PTG | 60 | 0.16 | 1.23 | 12.4 |
| 75 | 35% PTG | 93 | 0.32 | 2.99 | 12.4 |
| 76 | 40% PTG | 27 | 0.86 | 0.35 | 12.6 |

The I.V. data from Table V illustrate that the molecular weight of the blend components are preserved in the blending process. As the clarity indicates, the films were transparent which is characteristic of miscible blends. Furthermore, the Tg of the blend was measured for resentative samples. Entries 37, 49, 51, 54, 55, 59, and 74 had a single Tg of 120°, 70°, 125°, 72°, 66°, 108°, and 70° C., respectively. A single Tg is also characteristic of miscible blends. As Table VI demonstrates, a very wide range of physical properties for materials prepared from the blends are possible by proper selection of the blend composition.

Example 4

Blends of cellulose esters and adipate polyesters and films therefrom were prepared using the standard procedures. The results are given in Tables VII and VIII.

TABLE VII

DS/AGU, I.V., And Clarity of Cellulose Ester/Aliphatic Polyester Blends: C6 Diacids

| Entry | Polyester | $DS_{Ac}$ | $DS_{Pr}$ | $DS_{Bu}$ | I.V. CE | I.V. PE | I.V. Blend | Clarity |
|---|---|---|---|---|---|---|---|---|
| 77 | 20% PEA | 0.10 | 2.64 | — | 1.3 | 0.6 | 1.16 | + |
| 78 | 25% PEA | 0.10 | 2.64 | — | 1.3 | X | 1.11 | + |
| 79 | 30% PEA | 0.10 | 2.64 | — | 1.3 | 0.6 | 1.08 | + |
| 80 | 35% PEA | 0.10 | 2.64 | — | 1.3 | 0.6 | 1.04 | + |
| 81 | 40% PEA | 0.10 | 2.64 | — | 1.3 | 0.6 | 1.00 | + |
| 82 | 45% PEA | 0.10 | 2.64 | — | 1.3 | 0.6 | 0.96 | + |
| 83 | 50% PEA | 0.10 | 2.64 | — | 1.3 | 0.6 | 0.92 | + |
| 84 | 20% PDEA | 0.10 | 2.64 | — | 1.3 | 0.7 | 1.15 | + |
| 85 | 40% PDEA | 0.10 | 2.64 | — | 1.3 | 0.7 | 1.11 | + |
| 86 | 20% PHA | 0.10 | 2.64 | — | 1.3 | 0.7 | 1.17 | + |
| 87 | 40% PHA | 0.10 | 2.64 | — | 1.3 | 0.5 | 1.05 | + |

TABLE VIII

Mechanican Properties and Tear Properties of Films Prepared From Cellulose Ester/Polyester Blends: C6 Diacids

| Entry | Polyester | Elongation at Break (%) | Tangent Modulus ($10^5$ psi) | Tensile Strength $10^3$ psi | Tear Strength (g/mil) |
|---|---|---|---|---|---|
| 77 | 20% PEA | 13 | 1.39 | 3.95 | 4.1 |
| 78 | 25% PEA | 43 | 0.99 | 3.37 | 14.1 |
| 79 | 30% PEA | 74 | 0.57 | 2.76 | 16.6 |
| 80 | 35% PEA | 90 | 0.32 | 2.44 | 12.6 |
| 81 | 40% PEA | 75 | 0.14 | 1.37 | 13.0 |
| 82 | 45% PEA | 62 | 0.06 | 1.20 | 4.1 |
| 83 | 50% PEA | 75 | 0.03 | 1.03 | 4.7 |
| 84 | 20% PDEA | 24 | 1.46 | 4.05 | 6.0 |
| 85 | 40% PDEA | 64 | 0.12 | 1.11 | 13.3 |
| 86 | 20% PHA | 18 | 1.30 | 3.60 | 15.2 |
| 87 | 40% PHA | 81 | 0.14 | 1.36 | 13.6 |

The I.V. data from Table VII illustrate that the molecular weight of the blend components are preserved in the blending process. As the clarity indicates, the films were transparent which is characteristic of miscible blends. Furthermore, the Tg of the blend was measured for representative samples. Entries 80 and 84 had a single Tg of 78° and 130° C., respectively. A single Tg is also characteristic of miscible blends. As Table VIII demonstrates, a very wide range of physical properties for materials prepared from the blends are possible by proper selection of the blend composition.

Example 5

Blends of cellulose esters and aliphatic polyesters containing different additives and films therefrom were prepared using the standard procedures. The film of entries 96–101, 104, and 105 are blown film where T means transverse direction and M means machine direction. The results are given Tables IX and X.

TABLE IX

DS/AGU, I.V., Clarity of Cellulose Ester/Aliphatic Polyester Blends Containing Representative Additives

| Entry | Polyester/ Additive | $DS_{Ac}$ | $DS_{Pr}$ | $DS_{Bu}$ | I.V. CE | I.V. PE | Clarity |
|---|---|---|---|---|---|---|---|
| 88 | 39.9% PTG 0.1% Iron Stearate | 0.10 | 2.64 | — | 1.3 | 1.1 | + |
| 89 | 39.9% PTG 0.1% Zinc Stearate | 0.10 | 2.64 | — | 1.3 | 1.1 | + |
| 90 | 39.9% PTG 0.1% Mg Octanoate | 0.10 | 2.64 | — | 1.3 | 1.1 | + |
| 91 | 39.9% PTG 1% $CaCO_3$ | 0.10 | 2.64 | — | 1.3 | 1.1 | + |
| 92 | 39% PTG 1% $CaCO_3$ | 0.10 | 2.64 | — | 1.3 | 1.1 | + |
| 93 | 37.5% PTG 2.5% $CaCO_3$ | 0.10 | 2.64 | — | 1.3 | 1.1 | 1 |
| 94 | 39.75% PTG 0.25% Zeolite | 0.10 | 2.64 | — | 1.3 | 1.1 | + |
| 95 | 39% PTG 1% Zeolite | 0.10 | 2.64 | — | 1.3 | 1.1 | + |
| 96 | 40% $PTG^M$ 1% Microcrystalline Cellulose | 0.10 | 2.64 | — | 1.3 | 1.1 | + |
| 97 | 40% $PTG^T$ 1% Microcrystalline Cellulose | 0.10 | 2.64 | — | 1.3 | 1.1 | + |
| 98 | 40% $PTG^M$ 2% Microcrystalline Cellulose | 0.10 | 2.64 | — | 1.3 | 1.1 | + |
| 99 | 40% $PTG^T$ 2% Microcrystalline Cellulose | 0.10 | 2.64 | — | 1.3 | 1.1 | + |
| 100 | 40% $PTG^M$ 1% Microcrystalline Cellulose, 1% Silica, 1% $TiO_2$ | 0.10 | 2.64 | — | 1.3 | 1.1 | 1 |
| 101 | 40% $PTG^T$ 1% Microcrystalline Cellulose, 1% Silica, 1% $TiO_2$ | 0.10 | 2.64 | — | 1.3 | 1.1 | 1 |
| 102 | 20% PTG 10% TEGDA | 0.10 | 2.64 | — | 1.3 | 1.7 | + |
| 103 | 40% PTG 2.5% Cellulose Monoacetate, 0.5% MYVAPLEX 600 | 0.10 | 2.64 | — | 1.3 | 1.1 | + |
| 104 | 41% $PTG^M$ 0.5% PBT dye, 2% $TiO_2$, 1% MYVAPLEX 600 | 0.10 | 2.64 | — | 1.0 | Nm | |
| 105 | 41% $PTG^T$ 0.5% PBT dye, 2% $TiO_2$, 1% MYVAPLEX 600 | 0.10 | 2.64 | — | 1.0 | Nm | 1 |

1 Films were opaque or colored due to the additive

TABLE X

Mechanical Properties and Tear Strength of Films Prepared From Cellulose Ester/Polyester Blends Containing Representatives Additives

| Entry | Polyester/ Additive | Elongation at Break (%) | Modulus ($10^5$) | Strength ($10^3$) | Strength (g/mil) |
|---|---|---|---|---|---|
| 88 | 39.9% PTG 0.1% Iron Stearate | 83 | 0.18 | 2.22 | 10.8 |
| 89 | 39.9% PTG 0.1% Zinc Stearate | 68 | 0.14 | 1.70 | 11.1 |
| 90 | 39.9% PTG 0.1% Mg Octanoate | 74 | 0.14 | 1.97 | 11.5 |
| 91 | 39.9% PTG 0.1% $CaCO_3$ | 56 | 0.12 | 1.42 | 12.7 |
| 92 | 39% PTG 0.1% CaCO3 | 51 | 0.11 | 1.17 | 13.2 |
| 93 | 37.5% PTG 2.5% $CaCO_3$ | 52 | 0.19 | 1.38 | 14.2 |
| 94 | 39.75% PTG 0.25% Zeolite | 64 | 0.08 | 1.67 | 12.8 |
| 95 | 39% PTG 1% Zeolite | 52 | 0.13 | 1.27 | 12.4 |
| 96 | 40% $PTG^M$ 1% Microcrystalline Cellulose | 67 | 0.27 | 2.46 | 7.0 |
| 97 | 40% $PTG^T$ 1% Microcrystalline Cellulose | 36 | 0.30 | 1.09 | 6.8 |
| 98 | 40% $PTG^M$ 2% Microcrystalline Cellulose | 43 | 0.22 | 1.56 | 7.1 |
| 99 | 40% $PTG^T$ 2% Microcrystalline Cellulose | 59 | 0.27 | 1.89 | 6.8 |
| 100 | 40% $PTG^M$ 1% Microcrystalline Cellulose, 1% Silica, 1% TiO2 | 65 | 0.37 | 2.11 | 7.9 |
| 101 | 40% $PTG^T$ 1% Microcrystalline Cellulose, 1% Silica, 1% TiO2 | 48 | 0.24 | 1.76 | 8.3 |
| 102 | 20% PTG 10% TEGDA | 79 | 0.42 | 1.87 | 12.7 |
| 103 | 40% PTG 2.5% Cellulose Monoacetate, 0.5% MYVAPLEX 600 | 56 | 0.14 | 1.06 | 13.7 |

TABLE X-continued

Mechanical Properties and Tear Strength of Films Prepared From Cellulose Ester/Polyester Blends Containing Representatives Additives

| Entry | Polyester/ Additive | Elongation at Break (%) | Modulus ($10^5$) | Strength ($10^3$) | Strength (g/mil) |
|---|---|---|---|---|---|
| 104 | 41% PTG$^M$ 0.5% PTT dye, 2% TiO$_2$, 1% MYVAPLEX 600 | 80 | 0.17 | 3.40 | 10.0 |
| 105 | 41% PTG$^T$ 0.5% PTT dye, 2% TiO$_2$, 1% MYVAPLEX 600 | 68 | 0.30 | 4.48 | 7.5 |

As Table IX demonstrates, the blends of this invention can contain many different types of additives ranging from pro-oxidants (cf. entries 88–90), inorganics (cf. entries 91–95, 104,105), organic additives which are highly biodegradable (cf. 96–101, 103), polymer dyes and pigments (cf. 104 or 105), to monomeric plasticizers (cf.102) among others. Entries 88–90, 102 were transparent while entries 91–99, 103 were transparent but, as expected, hazy due to the inorganics or organics added to the blend. Entries 99 and 100 were white because of the TiO$_2$ while 104 and 105 were blue because of the TiO$_2$ and dye; these examples show that the blends can be readily pigmented or dyed. As can be seen from Table X, these additives have little or no effect on the mechanical properties or tear strength of films prepared from the blends (cf. Tables X and VI). Hence, additives e.g., CaCO$_3$ or microcrystalline cellulose which promote biodegradation can be added to the blends while maintaining a wide range of physical properties for materials prepared from the blends by proper selection of the blend composition.

Example 6

Ternary blends of cellulose acetate propionate with a DS/AGU of 2.74, aliphatic polyesters, and a third polymer component were prepared using the standard procedures. Table XI gives the mechanical properties, tear strength, and clarity of the films made from the blends.

TABLE XI

Mechanical Properties, Tear Strength, and Clarity of Films Prepared From CAP (DS/AGU = 2.75)/Aliphatic Polyester or Aliphatic-Aromatic Copolyester/Polymer Ternary Blends

| Entry | Polyester/Polymer | (%) | ($10^5$) | ($10^3$) | (g/mil) | Clarity |
|---|---|---|---|---|---|---|
| 106 | 40% PTG 2% Polyvinyl Alcohol (100% hydrolyzed, MW = 115,000) 0.5% Myvaplex 600 | 29 | 0.09 | 0.70 | 13.6 | − |
| 107 | 40% PTG 5% Polyvinyl Alcohol (100% hydrolyzed, MW = 115,000) 0.5% Myvaplex 600 | 31 | 0.05 | 0.60 | 14.4 | − |
| 108 | 40% PTG 5% Polyvinyl Alcohol (98–99% Hydrolyzed, MW = 31,000–50,000) 0.5% Myvaplex 600 | 68 | 0.05 | 1.28 | 11.3 | − |
| 109 | 40% PTG 2% Polyvinyl Alcohol (87–89% hydrolyzed, MW = 124,00–186,000) 0.5% Myvaplex 600 | 35 | 0.14 | 0.67 | 12.2 | − |
| 110 | 40% PTG 5% Polyvinyl Alcohol (87–89% hydrolyzed, MW = 124,000–186,000) 0.5% Myvaplex 600 | 37 | 0.10 | 0.70 | 14.4 | − |
| 111 | 40% PTG 5% Polyvinyl Alcohol (87–89% hydrolyzed, MW 31,000–50,000) 0.5% Myvaplex 600 | 67 | 0.11 | 1.32 | 11.9 | − |
| 112 | 40% PTG 5% Polyvinyl Alcohol (80% Hydrolyzed MW = 9,000–10,000) | 93 | 0.08 | 1.93 | 10.1 | + |
| 113 | 38% PTG 2% ECDEL 9810 | 49 | 0.06 | 0.65 | 12.7 | +/− |
| 114 | 35% PTG 5% Nylon 6 | 74 | 0.32 | 2.11 | 15.0 | − |
| 115 | 37.5% PTG 2.5% Nylon | 92 | 0.09 | 1.09 | 13.7 | +/− |
| 116 | 40% PTG 2% PVA, 0.5% MYVAPLEX 600 | 72 | 0.17 | 1.38 | 15.0 | + |
| 117 | 40% PTG 5% PVA, 0.5% MYVAPLEX 600 | 93 | 0.11 | 1.56 | 18.3 | + |
| 118 | 40% PTG 10% PVA | 88 | 0.10 | 1.55 | 14.4 | +/− |
| 119 | 28% PEG 52% PVA | 306 | 0.05 | 1.28 | NT | +/− |
| 120 | 31% PEG 59% PVA | 509 | 0.02 | 1.06 | NT | +/− |
| 121 | 40% PTG 5% PMMA, 0.5% MYVAPLEX 600 | 86 | 0.12 | 1.45 | 17.4 | + |
| 122 | 40% PTG 2% PMMA, 0.5% MYVAPLEX 600 | 61 | 0.17 | 1.15 | 12.4 | + |
| 123 | 40% PTG 10% PMMA | 75 | 0.10 | 1.48 | 11.3 | + |
| 124 | 40% PTG 5% PEMA, 0.5% MYVAPLEX 600 | 48 | 0.17 | 0.93 | 16.2 | + |
| 125 | 40% PTG 2% PEMA, 0.5% MYVAPLEX 600 | 71 | 0.19 | 1.23 | 13.2 | + |
| 126 | 40% PTG 10% PEMA | 57 | 0.10 | 0.94 | 13.9 | + |
| 127 | 35% PTG 5% Hydroxypropyl Cellulose (MW = 100,000) | 70 | 0.20 | 1.80 | 20.3 | + |
| 128 | 39% PTG 1% Hydroxypropyl Cellulose (MW = 1,000,000) | 80 | 0.15 | 1.71 | 21.2 | + |
| 129 | 35% PTG 5% Hydroxypropyl Cellulose (MW = 1,000,000) | 80 | 0.22 | 1.74 | 16.9 | + |
| 130 | 40% PTG 2% Ethylene/Vinyl Acetate Copolymer (40% Vinyl Vcetate) | 81 | 0.02 | 0.60 | 11.1 | + |

TABLE XI-continued

Mechanical Properties, Tear Strength, and Clarity of Films Prepared From CAP (DS/AGU = 2.75)/Aliphatic Polyester or Aliphatic-Aromatic Copolyester/Polymer Ternary Blends

| Entry | Polyester/Polymer | (%) | ($10^5$) | ($10^3$) | (g/mil) | Clarity |
|---|---|---|---|---|---|---|
| 131 | 35% PTG 2% Ethylene/Vinyl Acetate Copolymer (40% Vinyl Acetate) | 59 | 0.29 | 1.92 | 11.5 | + |
| 132 | 35% PTG 5% Ethylene/Vinyl Acetate Copolymer (40% Vinyl Acetate) | 43 | 0.20 | 1.40 | 10.9 | + |
| 133 | 35% PTG 10% Ethylene/Vinyl Acetate Copolymer (40% Vinyl Acetate) | 44 | 0.08 | 0.98 | 8.8 | +/− |
| 134 | 35% PTG 2% Ethylene/Vinyl Acetate Copolymer (50% Vinyl Acetate) | 35 | 0.46 | 1.09 | 8.0 | + |
| 135 | 35% PTG 5% Ethylene/Vinyl Acetate Copolymer (50% Vinyl Acetate) | 35 | 0.13 | 1.03 | 8.7 | + |
| 136 | 35% PTG 10% Ethylene/Vinyl Acetate Copolymer (50% Vinyl Acetate) | 28 | 0.05 | 0.80 | 10.4 | ± |
| 137 | 35% PTG 2% Ethylene/Vinyl Acetate Copolymer (70% Vinyl Acetate) | 68 | 0.28 | 1.93 | 13.3 | + |
| 138 | 35% PTG 5% Ethylene/Vinyl Acetate Copolymer (70% Vinyl Acetate) | 67 | 0.24 | 1.86 | 14.5 | + |
| 139 | 35% PTG 10% Ethylene/Vinyl Acetate Copolymer (70% Vinyl Acetate) | 79 | 0.17 | 1.67 | 12.5 | ± |
| 140 | 40% PTG 2% Lexan ® Polycarbonate | 75 | 0.07 | 1.40 | nm | − |
| 141 | 40% PTG 5% Lexan ® Polycarbonate | 70 | 0.08 | 1.28 | nm | − |
| 142 | 40% PTG 10% Lexan ® Polycarbonate | 65 | 0.04 | 1.15 | nm | − |

As Table XI shows, cellulose esters and aliphatic polyesters or aliphatic-aromatic copolyesters can be blended with other polymers to form either miscible or partially miscible ternary blends which have excellent physical properties. Entries 112, 116, 117, 119–130, 132, 133, 135, and 136 are examples of miscible ternary blends while the remaining examples are ternary blends which are partially miscible. These blends can, of course, contain immiscible additives demonstrated in Example 5 or in Example 7 (vide infra).

Example 7

Ternary blends of cellulose esters and aliphatic polyesters or aliphatic-aromatic copolyester, and a hydrophobic additive were prepared using the standard procedures. Tables XII and XIII gives the DS/AGU, I.V., and clarity of the blends as well as the mechanical properties, tear strength, and water vapor transmission rates of the films made from the blends.

TABLE XII

DS/AGU, I.V., and Clarity of Cellulose Ester/Polyester Blends Containing Hydrophobic Additives

| Entry | Polyester/Hydrophobic Additive | $DS_{Ac}$ | $DS_{Pr}$ | $DS_{Bu}$ | I.V. CE | I.V. PE | Blend | Clarity |
|---|---|---|---|---|---|---|---|---|
| 143 | 39.95% PTG 0.05% MYVAPLEX 600 | 0.10 | 2.64 | — | 1.3 | 1.1 | nm | + |
| 144 | 39.9% PTG 0.1% MYVAPLEX 600 | 0.10 | 2.64 | — | 1.3 | 1.1 | nm | + |
| 145 | 39.75% PTG 0.25% MYVAPLEX 600 | 0.10 | 2.64 | — | 1.3 | 1.1 | nm | |
| 146 | 39.5% PTG 0.5% MYVAPLEX 600 | 0.10 | 2.64 | — | 1.3 | 1.1 | nm | + |
| 147 | 39.25% PTG 0.75% MYVAPLEX 600 | 0.10 | 2.64 | — | 1.3 | 1.1 | nm | + |
| 148 | 39% PTG 1% MYVAPLEX 600 | 0.10 | 2.64 | — | 1.3 | 1.1 | 1.19 | + |
| 149 | 38.5% PTG 1.5% MYVAPLEX 600 | 0.10 | 2.64 | — | 1.3 | 1.1 | 1.22 | + |
| 150 | 38% PTG 2% MYVAPLEX 600 | 0.10 | 2.64 | — | 1.3 | 1.1 | 1.18 | + |
| 151 | 39% PTG 1% MYVACET 507 | 0.10 | 2.64 | — | 1.3 | 1.1 | 1.23 | + |
| 152 | 39% PTG 1% MYVACET 707 | 0.10 | 2.64 | — | 1.3 | 1.1 | 1.22 | + |
| 153 | 39% PTG 1% MYVACET 908 | 0.10 | 2.64 | — | 1.3 | 1.1 | 1.23 | + |

TABLE XII-continued

DS/AGU, I.V., and Clarity of Cellulose Ester/Polyester Blends Containing Hydrophobic Additives

| Entry | Polyester/Hydrophobic Additive | $DS_{Ac}$ | $DS_{Pr}$ | $DS_{Bu}$ | I.V. CE | I.V. PE | Blend | Clarity |
|---|---|---|---|---|---|---|---|---|
| 154 | 39% PTG<br>1% MYVEROL 18–07 | 0.10 | 2.64 | — | 1.3 | 1.1 | nm | + |
| 155 | 39% PTG<br>1% MYVEROL 18–35 | 0.10 | 2.64 | — | 1.3 | 1.1 | nm | + |
| 156 | 39% PTG<br>1% MYVEROL 18–99 | 0.10 | 2.64 | — | 1.3 | 1.1 | nm | + |
| 157 | 39% PTG<br>1% paraffin | 0.10 | 2.64 | — | 1.3 | 1.1 | 1.21 | + |
| 158 | 38% PTG<br>2% paraffin | 0.10 | 2.64 | — | 1.3 | 1.1 | 1.18 | + |
| 159 | 49% PEG(T) (70/30)<br>1% MYVAPLEX 600 | 0.10 | 2.64 | — | 1.3 | 0.6 | 0.89 | + |

TABLE XIII

Mechanical Properties, Tear Strength, Water Vapor Transmission Rates of Films Prepared from Cellulose Ester/Polyester Blends Containing Hydrophobic Additives

| Entry | Polyester/Hydrophobic Additive | Elongation at Break (%) | Tangent Modulus ($10^5$) | Tensile Strength ($10^3$) | Tear Strength (g/mil) | (g mil/100 in$^2$-24 hours) |
|---|---|---|---|---|---|---|
| 143 | 39.95% PTG<br>0.05% MYVAPLEX 600 | 75 | 0.13 | 1.66 | 9.6 | 306 |
| 144 | 39.9% PTG<br>0.1% MYVAPLEX 600 | 92 | 0.17 | 2.06 | 11.6 | <500 |
| 145 | 39.75% PTG<br>0.25% MYVAPLEX 600 | 78 | 0.16 | 1.64 | 9.5 | 244 |
| 146 | 39.5% PTG<br>0.5% MYVAPLEX 600 | 93 | 0.11 | 2.10 | 14.9 | 227 |
| 147 | 39.25% PTG<br>0.75% MYVAPLEX 600 | 81 | 0.11 | 1.67 | 12.8 | 171 |
| 148 | 39% PTG<br>1% MYVAPLEX 600 | 71 | 0.11 | 1.47 | 10.8 | 103 |
| 149 | 38.5% PTG<br>1.5% MYVAPLEX 600 | 75 | 0.12 | 1.71 | 14.0 | 159 |
| 150 | 38% PTG<br>2% MYVAPLEX 600 | 62 | 0.11 | 1.45 | 9.8 | 178 |
| 151 | 39% PTG<br>1% MYVACET 507 | 82 | 0.11 | 1.76 | 12.7 | 200 |
| 152 | 39% PTG<br>1% MYVACET 707 | 64 | 0.09 | 1.69 | 9.5 | 261 |
| 153 | 39% PTG<br>MYVACET 908 | 75 | 0.09 | 2.39 | 12.6 | 258 |
| 154 | 39% PTG<br>1% MYVEROL 18–07 | 62 | 0.15 | 1.27 | 12.5 | 146 |
| 155 | 39% PTG<br>1% MYVEROL 18–35 | 92 | 0.07 | 2.04 | 12.2 | 181 |
| 156 | 39% PTG<br>1% MYVEROL 18–99 | 75 | 0.08 | 1.32 | 13.7 | 397 |
| 157 | 39% PTG<br>1% paraffin | 105 | 0.10 | 2.35 | 15.9 | 238 |
| 158 | 38% PTG<br>2% paraffin | 65 | 0.15 | 1.66 | 17.1 | 231 |
| 159 | 49% PEG(T)[70/30]<br>1% MYVAPLEX 600 | 48 | 0.10 | 1.35 | 7.6 | 106 |

The examples of Tables XII and XIII illustrate that hydrophobic additives can be added to blends of cellulose esters and aliphatic polyesters or aliphatic-aromatic copolyesters to control water vapor transmission rates of materials prepared from the blends without loss of mechanical properties or tear strength. For example, the WVTR of the films prepared from a CAP/PTG blend containing 0.25–1% MYVAPLEX 600 was controlled between 244 to 103 g mil/100 in$^2$–24 hours (cf entries 143–146). With increasing hydrophobic additive, the WVTR decreased until the WVTR leveled off at around 1% additive.

Example 8

Preparation of a 65/35 blend of CAP($DS_{Ac}$=0.10, $DS_{Pr}$=2.64)/poly(tetramethylene glutarate) on the 30 mm W-P twin screw extruder was performed under the following conditions according to the general procedure.

Feed rate for poly(tetramethylene glutarate)=15.0 lb/hr
Feed rate for CAP=28.0 lb/hr Total output from extruder=43 lb/hr
Feed Line temperature=190° C.
RPM of the Screw–207
Torque=30%
Extruder zone temperatures: Zone 1=180° C.; Zones 2–7=230° C.

Example 9

Other blends, including 10, 20, and 40 wt. % polytetramethylene glutarate with CAP (DS$_{Ac}$=0.10, DS$_{Pr}$=2.64) were also prepared on the W-P extruder according to the general procedure except that the polyester was added by mixing solid poly(tetramethylene glutarate) with CAP(DS$_{Ac}$=0.10, DS$_{Pr}$=2.64) and feeding both materials into Zone 1 of the extruder under otherwise similar conditions.

Example 10

Blends prepared as in Examples 8 and 9 were molded on a Toyo 90 injection molding machine under the following conditions. These conditions should not be considered the ideal conditions, but are typical of those that can be used on blends of this type.
Nozzle temperature=200° C.
Zone 1 temperature=210° C.
Zone 2 temperature=210° C.
Zone 3 temperature=190° C.
Zone 4 temperature=180° C.
Melt temperature=215° C.
Injection and Hold Pressures=750 psig
Mold temperature=14° C.
Screw speed=75 rpm

TABLE XIV

Physical Properties of Blends of CAP (Ds$_{AC}$ = 0.10, DS$_{Pr}$ = 2.64) and Poly(Tetramethylene Glutarate)

| Property (units) | 10% PTG | * 20% PTG | 35% PTG | 40% PTG | 12% DOA |
|---|---|---|---|---|---|
| Tensile Strength (10$^3$ psi) | 7.9 | 5.3 | 2.8 | 2.3 | 4.76 |
| Elongation at break (%) | 14 | 41 | 72 | 93 | 27 |
| Flexural Modulus (10$^5$ psi) | 3.3 | 2.1 | 0.78 | 0.18 | 2.16 |
| Izod Impact 23° (ft-lb/in) | 1.7(C) | 4.6(C)* | 15.4 (PB) | 12.9 (NB) | 7.43 |
| HDT (° C.) | 81 | 54 | 41 | NT | 67 |

This example demonstrates that aliphatic polyester blend components are very effective non-volatile, non-extractable polymeric additives. These blends offer many superior physical properties relative to a CAP containing a monomeric plasticizer. For example, relative to a CAP containing 12% DOA, the blend containing 10% PTG has superior tensile strength, flexural modulus, and a higher heat deflection temperature.

Example 12

The physical properties of blends prepared as in Example 10 are shown in Table XIV.

TABLE XV

Physical Properties of Blends of CAP (DS$_{Ae}$ = 0.10, DS$_{Pr}$ = 2.64) and Aliphatic Aromatic Polyesters as well as Physical Properties of the CAP Containing 12% Monomeric Plasticizer

| Property (units) | 8% PEG(T) [70/30] | 16% PEG(T) [70/30] | 24% PEG(T) [70/30] | 8% PTG(T) [60/40] | 16% PTG(T) [60/40] | 24% PTG(T) [60/40] | 12% DOA |
|---|---|---|---|---|---|---|---|
| Tensile Strength (10$^3$ psi) | 8.32 > | 8.79 | 7.46 | 8.67 | 8.64 | 7.79 | 4.76 |
| Elongation at break (%) | 8 | 8 | 14 | 11 | 11 | 17 | 27 |
| Flexural Modulus (10$^3$ psi) | 3.53 | 3.23 | 2.52 | 3.43 | 3.25 | 2.72 | 2.16 |
| Flexural Strength (10$^3$ psi) | 10.43 | 9.98 | 7.97 | 10.82 | 10.32 | 8.74 | 5.67 |
| Izod Impact 23° C. (ft-lb/in) | 1.63 | 1.70 | 1.82 | 3.00 | 2.69 | 2.96 | 7.43 |
| Izod Impact –40° C. (ft-lb/in) | 0.77 | 0.76 | 0.25 | 2.16 | 2.11 | 2.23 | 2.94 |
| HDT 66 psi (° C.) | 82 | 68 | 52 | 93 | 74 | 59 | 67 |

Example 11

The physical properties of the blends prepared as in Example 10 are shown in Table XIV as well as physical properties of the CAP containing 12% monomeric plasticizer.

This example demonstrates that aliphatic-aromatic polyester blend components are very effective non-volatile, non-extractable polymeric additives. These blends offer many superior physical properties relative to a CAP containing a monomeric plasticizer. For example, relative to the a CAP containing 12% DOA, all of the above blends at similar polymer content have superior tensile strengths, flexural moduli, and flexural strengths as well as higher heat deflection temperatures. This example also teaches some of the physical property differences between a miscible, i.e., PEG(T) [70/30], cellulose ester/aliphatic-aromatic blend and a partially miscible, i.e., PEG(T) [60/40], cellulose ester/aliphatic-aromatic blend. In general, the partially miscible blend offers superior Izod impact strengths, particularly at −40° C.

Example 13

TABLE XVI

Inherent Viscosity, Water Vapor Transmission Rates, Mechanical Properties and Tear Strength of Films Prepared From Aliphatic-Aromatic Copolyesters

| Entry | Polyester | Elongation at Break (%) | Tangent Modulus psi | Tensile Strength psi | Tear Strength (g/mil) | I.V. | WVTR (g/100 in² 24 hours) |
|---|---|---|---|---|---|---|---|
| 160 | PHG(T) [50/50] | 357 | 0.09 | 0.73 | 26 | 0.72 | 65 |
| 161 | PTG(T) [60/40] | 908 | 0.05 | 1.95 | 214 | 1.15 | 137 |
| 162 | PTG(T) [40/60] | 642 | 0.23 | 3.07 | 115 | 0.94 | 52 |
| 163 | PTS(T) [70/30] | 722 | 0.41 | 4.48 | 59 | nm | nm |
| 164 | PTS(T) [85/15] | 732 | 0.28 | 3.99 | 42 | 1.03 | 42 |
| 165 | PTG(T) [55/45] | 738 | 0.08 | 3.54 | 142 | 1.11 | nm |
| 166 | PTG(T)(D) [50/45/5] | 927 | 0.05 | 5.22 | 126 | 1.23 | nm |

These examples illustrate that films prepared from aliphatic-aromatic copolyesters have very high elongation, high tear strengths, low WVTR, and low moduli and hence are useful in film applications.

Example 14
The Physical Properties of AAPE Molded Bars

TABLE XVII

Physical Properties of AAPE

| Property (units) | PTS(T) [85/15] | PTS(T) [70/30] | PTG(T) [50/50] |
|---|---|---|---|
| Tensile Strength (10³ psi) | 2.89 | 1.79 | 1.51 |
| Elongation at break (%) | >482 | 384 | 437 |
| Flexural Modulus (10⁵ psi) | 0.57 | 0.20 | 0.13 |
| Izod Impact 23° C. (ft-lb/in) | 6.0 (NB) | 6.5 (NB) | 3.2 (NB) |
| Izod impact −40° C. (ft-lb/in) | 0.44 (CB) | 0.86 (CB) | 8.23 (NB) |

This example demonstrates that AAPEs have very high elongation at break, low flexural modulus and excellent Izod impact strengths.

Example 15

A variety of conditions are available for producing melt blown films from the blends of this invention. Temperature set points for the extruders can vary depending on the level of additives, if any. For this example, all heater zones were set between 190° and 200° C. with a screw rpm of 25 to 30. This produced a measured melt temperature of 183° C. Heater temperatures must be increased, especially in the die area, by 5° to 10° C. if higher levels of $TiO_2$ (or any antiblock agents such as talc or diatomaceous earth) are used in order to prevent clogging of the die.

Temperature settings will also vary depending on the type of screw used and the size of the extruder. The preferred temperatures are 175°–215° C. Blowing conditions can be characterized by the blow up ratio (BUR), the ratio of bubble diameter to die diameter which gives an indication of hoop or transverse direction (TD) stretch; or the draw-down ratio (DDR), which is an indication of the axial or machine direction (MD) stretch. If the BUR and DDR are equal then the amount of stretch in the MD and TD is approximately the same resulting in "balanced" film.

Blown film was produced from a blend consisting of 98% of a 60/40 blend of cellulose acetate propionate ($DS_{Ac}$=0.10, $DS_{Pr}$=2.64) and poly(tetramethylene glutarate), and 2% $TiO_2$. The $TiO_2$, added in the form of a masterbatch (blended at a level of 20% and pelletized), was added in order to obtain an opaque film. The blown film was produced using a laboratory scale blown film line which consisted of a Killion 1.25 inch extruder with a 15:1 gear reducer. The screw was a Maddock mixing type with an L/D of 24 to 1 although a general purpose screw has also been used. Compression ratio for the mixing screw was 3.5:1. A 1.21 inch die with a 5 mil die gap was used. The air ring was a Killion single-lip, No. 2 type. Prior to processing, the blends were dried overnight at 50° C. in dehumidified air dryers.

For this example, the BUR was 2.20 and the DDR was 1.13 resulting in a film with an average thickness of 2 mils. This produced a film with average tear strengths of 8.9 and 7.5 g/mil in the MD and TD, respectively. Additionally, elongation to break values for these directions are 101 and 79%, tangent moduli are 30 and 24 ksi, and break stresses are 3.9 and 3.6 ksi. BUR values have been tried ranging from 2 to 3.9 and DDR values from 0.5 to 20 by changing blow conditions and also going to a thicker die gap. Increasing these parameters generally results in improved properties except for % elongation which is reduced. For example, a 0.5 mil film with a BUR of 2.76 and a DDR of 3.89 had average tear strengths of 31.3 and 29.7 g/mil, elongation to break values of 74 and 37%, moduli of 57 and 86 ksi, and break stresses of 3.2 and 4.9 ksi for the MD and TD, respectively.

Example 16

Blown film was produced from blends consisting of cellulose acetate propionate ($DS_{Ac}$=0.10, $DS_{Pr}$=2.64) and poly(tetramethylene glutarate-co-terephthalate). The blown film was produced using a laboratory scale blown film line which consisted of a Killion 1.25 inch extruder with a 15:1 gear reducer. The screw was a Maddock mixing type with an L/D of 24 to 1 although a general purpose screw has also been used. Compression ratio for the mixing screw was 3.5:1. A 1.21 inch die with a 25 mil die gap was used. The air ring was a Killion single-lip, No. 2 type. Prior to processing, the blends were dried overnight at 50° C. in dehumidified air dryers. The results are given in Table XVII.

TABLE XVIII

Conditions and Results for Blown Film of a Cellulose Acetate Propionate and Poly(tetremethylene Glutarate-co-terephthalate)

| Entry[a] | Description[b] | Film Thickness (mils) | BUR | DDR | Tear[c] Strength (g/mil) | Elongation (%) | Tangent Modulus ksi) |
|---|---|---|---|---|---|---|---|
| 167 | 35/65 [50/50] | 2.41 * | 3.2 * | 3.9 13.4 | 50.8 156 | 80 37 | 55 |
| 168 | 25/75 [50/50] | 1.21 | 3.1 | 8.1 | 57.7 49.0 | 121 257 | 24 19 |
| 169 | 35/65 [55/45] | 2.11 | 2.6 | 4.6 | 74.8 15.5 | 123 161 | 36 33 |
| 170 | 25/75 [55/45] | 1.95 | 2.6 | 4.9 | 101.1 59.7 | 121 344 | 35 23 |
| 171 | 35/65 [60/40] | 2.19 | 2.6 | 4.4 | 36.6 29.4 | 124 178 | 18 9 |

[a]Each sample contained inorganics.
[b]The first ratio (e.g., 35/65) is the ratio of cellulose ester to copolyester in the blend. The second ratio (e.g., [50/50]) is the ratio of glutarate to terephthalate in the copolyester.
[c]The first value is for the machine direction and the second value is for the transverse direction.

The entries of this example demonstrate that film blown from blends of cellulose acetate propionate and aliphatic-aromatic copolyesters have very high tear strengths and elongation at break. Moreover, physical properties such as tear strength can be high in one direction or can be roughly equal in both directions demonstrating that this film can be oriented. In general, a balanced film is obtained by choice of the DDR/BUR ratio.

Example 17

An 80/20 blend of cellulose acetate propionate ($DS_{Ac}$=0.10, $DS_{Pr}$=2.64)/poly(tetramethylene glutarate) was used to spin fibers using a 54 hole round and Y jet (55 micron equivalent diameter) at an extrusion temperature of 215° C. and a takeup of 250 m/m or 600 m/m. Packages were doffed and plied together onto cones making 270 filament yarn. A two step draw process was used to make drawn fiber. Table XV gives representative data for both drawn and undrawn fiber. Photomicrographs showed that the fibers had excellent cross-sectional stability.

TABLE XIX

Strand Tensiles of Fiber Melt-Spun From an 80/20 Blend of Cellulose Acetate Propionate/Poly(Tetramethylene Glutarate)

| Entry | Temp (° C.)/Draw Ratio | Denier | Tenacity | Elongation | g/ Denier | g/ Denier |
|---|---|---|---|---|---|---|
| 172 | undrawn | 905 | 0.42 | 38 | 16 | 0.14 |
| 172B | 70/1.82 | 486 | 0.98 | 4 | 45 | 0.02 |
| 173 | undrawn | 1478 | 0.54 | 49 | 16 | 0.21 |
| 173B | 85/1.75 | 892 | 0.93 | 5 | 41 | 0.03 |
| 174 | undrawn | 877 | 0.66 | 26 | 19 | 0.14 |
| 174B | 70/1.33 | 673 | 1.02 | 4 | 42 | 0.03 |

TABLE XIX-continued

Strand Tensiles of Fiber Melt-Spun From an 80/20 Blend of Cellulose Acetate Propionate/Poly(Tetramethylene Glutarate)

| Entry | Temp (° C.)/Draw Ratio | Denier | Tenacity | Elongation | g/ Denier | g/ Denier |
|---|---|---|---|---|---|---|
| 175 | undrawn | 898 | 0.55 | 26 | 17 | 0.12 |
| 175B | 70/1.40 | 655 | 0.88 | 3 | 42 | 0.01 |

Biodegradation Studies

Figure 1B:
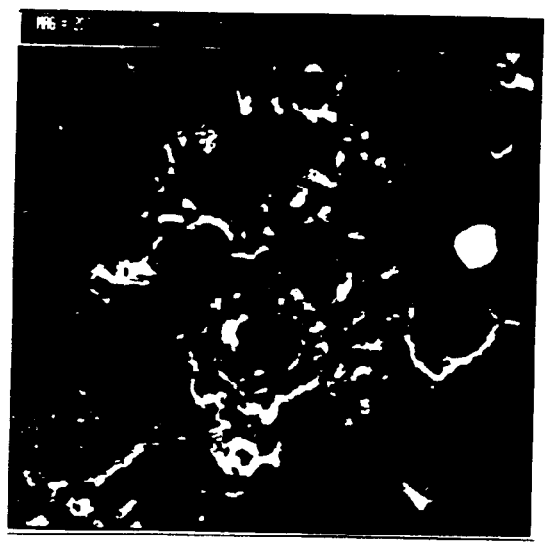
FIG. 1B SEM photograph of the outer, smooth surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system. Magnification is 200×.
Figure 2A:
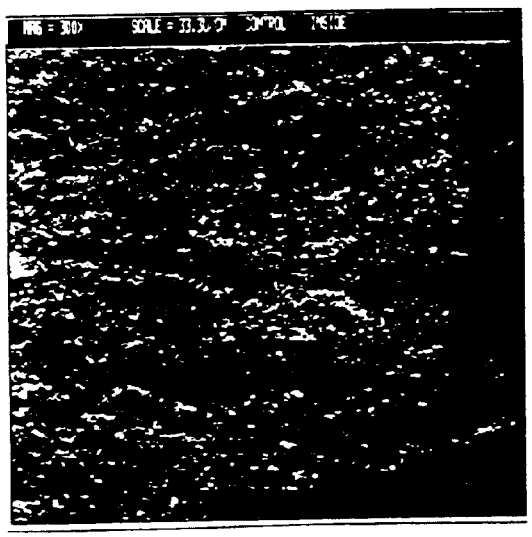
FIG. 2A SEM photograph of the inner, rough surface of a cellulose acetate (DS=1.7) film formed by drawing a film from a 20 wt. % solution of cellulose acetate in a 50/50 (vol./vol.) mixture of water/acetone. Magnification is 300×.
Figure 2B:
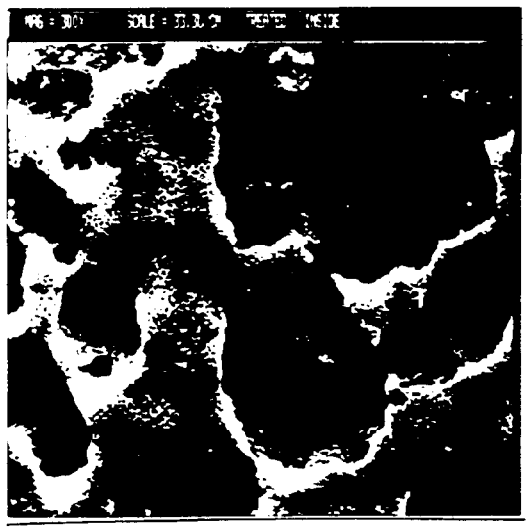
FIG. 2B SEM photograph of the inner, rough surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system. Magnification is 300×.
Figure 3:
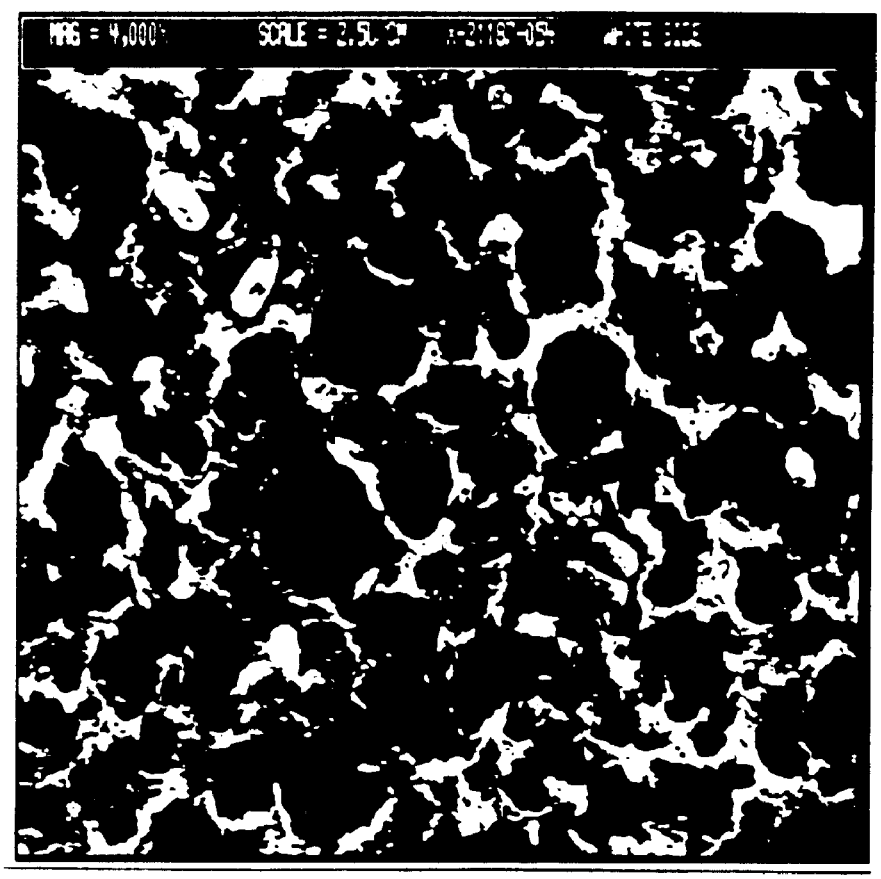
FIG. 3 SEM photograph of the outer, smooth surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system from which the bacteria has not been washed. Magnification is 4,000×.
Figure 4:
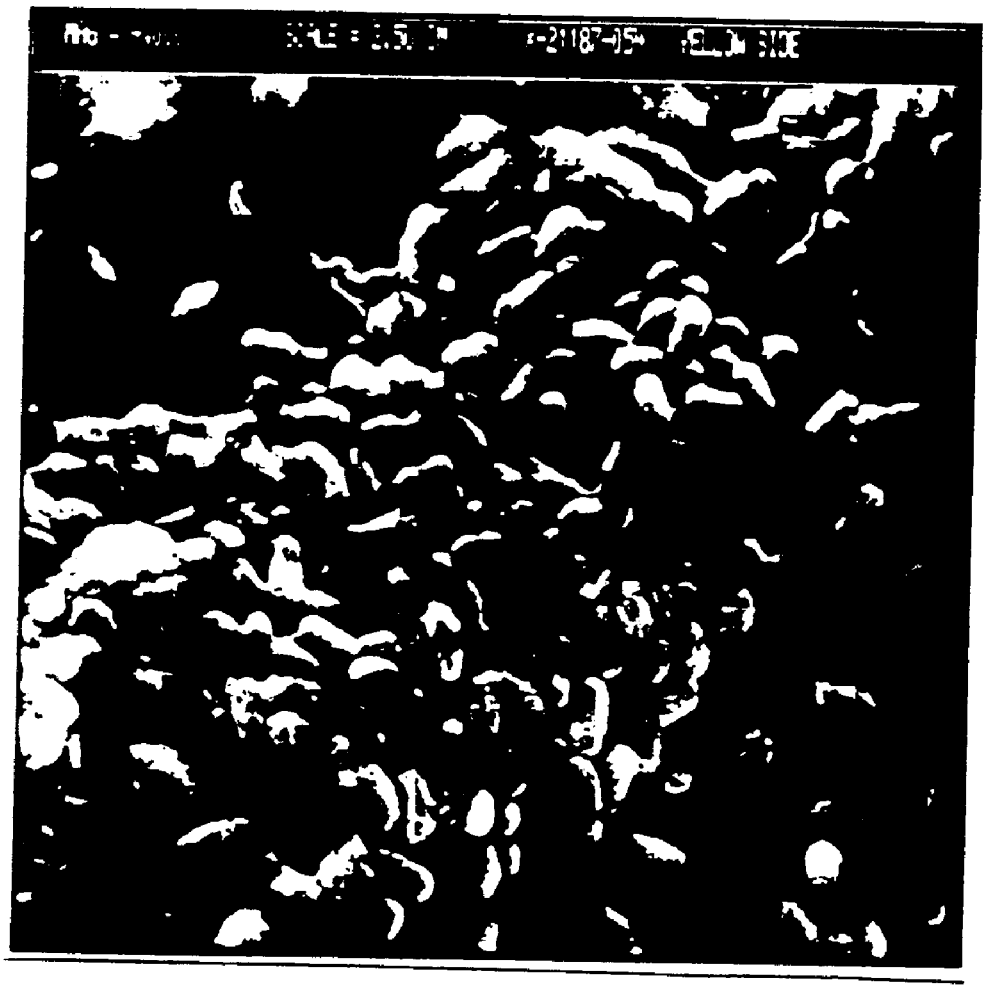
FIG. 4 SEM photograph of the inner, rough surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system from which the bacteria have not been washed. Magnification is 4,000×.

Although it is evident that polyhydroxyalkanoates are biodegradable under the appropriate conditions, it is not known in the art that cellulose esters are biodegradable since it is widely believed that the acyl substituents shield the cellulose backbone from microbial attack. We have found that when films of cellulose acetate having a degree of substitution of 1.7 were immersed in Eastman Chemical Company (Kingsport, Tenn., U.S.A.) wastewater treatment facility, extensive degradation of the films occurred within 27 days. In addition, a culture consisting of a mixed population of microbes isolated from the activated sludge obtained from the same wastewater treatment facility were grown in the presence of films of the same cellulose acetate (DS=1.7). In this case, extensive degradation of the cellulose acetate films was observed after 5 days. FIGS. 1A, 1B, 2A, and 2B show scanning electron microscopy (SEM) photographs of the two sides of cellulose acetate films formed by drawing a film from a solution consisting of 20% cellulose acetate (DS=1.7) by weight in a 50/50 mixture of water/acetate. FIGS. 1A and 2A are of a control film while FIGS. 1B and 2B are of a film on which the culture, consisting of a mixed population of microbes isolated from the activated sludge, was grown for 4 days. In FIGS. 1B and 2B, extensive degradation of the cellulose acetate film is evident. Comparison of the control films in FIGS. 1A and 2A shows that the film sides are different. FIG. 1A shows the outer, smooth surface of the film which results from shearing by the draw blade while FIG. 2A shows the inner, rough surface of the film which was in contact with the surface on which the film was cast. Comparison of FIGS. 1B and 2B shows that the rough or inner side of the film was more extensively degraded. A rough surface area promotes attachment of the bacteria leading to a more rapid rate of degradation. Processes, such as foamed films and the like, which promote rough surfaces are desirable in the practice of this invention. FIGS. 3 and 4 show SEM photographs of the smooth and rough sides of a cellulose acetate film from which the bacteria were not washed. In addition to showing extensive pitting of the film surface due to degradation of the cellulose acetate, these films show the attached microbes in the cavities where degradation is occurring.

In vitro Enrichment System: fresh composite samples of activated sludge are obtained from the AA 03 aeration basins in Eastman Chemical Company (Kingsport, Tenn., U.S.A.) wastewater treatment plant which has a design capacity of receiving 25 million gallons of waste per day with BOD concentration up to 200,000 pounds per day. The major waste components consist largely of methanol, ethanol, isopropanol, acetone, acetic acid, butyric acid, and propionic acid. The sludge operating temperatures vary between 35° C. to 40° C. In addition, a dissolved oxygen concentration of 2.0 to 3.0 and a pH of 7.1 are maintained to insure maximal degradation rates. The activated sludge serves as the starting inoculum for the stable mixed population of microbes used in this invention. A stable population is obtained by serially transferring the initial inoculum (5% v/v) to a basal salt media containing glucose or cellobiose, acetate, and cellulose acetate (DS=2.5).

Cellulose ester film degrading enrichments are initiated in a basal salts medium containing the following ingredients per liter: 50 mL of Pfennig's Macro-mineral solution, 1.0 mL of Pfennig's trace element solution, 0.1% (wt/vol) Difco yeast extract, 2 mM $Na_2SO_4$, 10 mM $NH_4Cl$ which supplements the ammonia levels provided by Pfennig's Macro-mineral solution, 0.05% (wt/vol) cellobiose, 0.05% (wt/vol) NaOAc. This solution is adjusted to pH 7.0 and a final volume of 945 mL before being autoclaved at 121° C. at 15 psi for 15 minutes. After cooling to room temperature, 50 mL of sterile 1M phosphate buffer and 5 mL of a complex vitamin solution which has been filtered through a 0.02 mm filter are added. The test cellulosic film is then added and the flask is inoculated (5% v/v) with a stable mixed population enrichment. The flask is placed in a New Brunswick incubator and held at 30° C. and 250 rpm for the appropriate period. Initially, the films are often observed to turn cloudy and to be coated with a yellow affinity substance (*Current Microbiology*, 9, 195 (1983)), which is an indication of microbial activity. After 4 to 12 days, the films are broken into small pieces at which time they are harvested by pouring the media through a filter funnel. The pieces are collected and washed with water. The film pieces are suspended in a neutral detergent solution at 90° C. for 30–60 minutes before washing extensively with water. The films are placed in a vacuum oven at 40° C. until dry before weighing. In each experiment, control experiments are conducted in which the films are subjected to the same experimental protocol except inoculation with the microbes.

| | Cellulose Acetate, DS = 1.7 | | |
|---|---|---|---|
| Film Number | Original Weight (mg) | Final Weight (mg) | Weight Loss |
| 1* | 190 | 181 | 5 |
| 2* | 233 | 220 | 6 |
| 3* | 206 | 196 | 5 |
| 4 | 134 | 2 | 99 |
| 5 | 214 | 35 | 84 |
| 6 | 206 | 16 | 92 |
| 7* | 195 | 184 | 5 |
| 8* | 187 | 175 | 6 |
| 9 | 177 | 3 | 98 |
| 10 | 181 | 5 | 97 |
| 11* | 167 | 164 | 2 |
| 12* | 174 | 173 | 1 |
| 13* | 188 | 185 | 2 |
| 14 | 192 | 30 | 84 |
| 15 | 154 | 5 | 97 |

Films 1–6, 7–10, and 11–15 represent the results for three separate experiments. Films 1–6 and 11–15 are shaken for 4 days while Films 7–10 are shaken for 5 days. The films with the * represent control films.

In every case, weight loss of 84–99% is observed for the inoculated films and only 0.6–6.4% for the control films.

| | Cellulose Actetate, DS = 2.5 | | |
|---|---|---|---|
| Film Number | Original Weight (mg) | Final Weight (mg) | % Weight Loss |
| 1* | 135 | 136 | 0 |
| 2* | 161 | 161 | 0 |
| 3* | 132 | 131 | 0.8 |
| 4 | 147 | 148 | 0 |
| 5 | 146 | 40 | 73 |
| 6 | 169 | 60 | 65 |
| 7 | 175 | 81 | 54 |
| 8 | 157 | 36 | 77 |

Each film is shaken for 12 days. The films with the * represent control films. In every case, weight losses of 54–77% are observed for the inoculated films and 0–0.8% for the control films. As expected, the films with a higher degree of substitution exhibit greater resistance to microbial attack.

Figure 5:
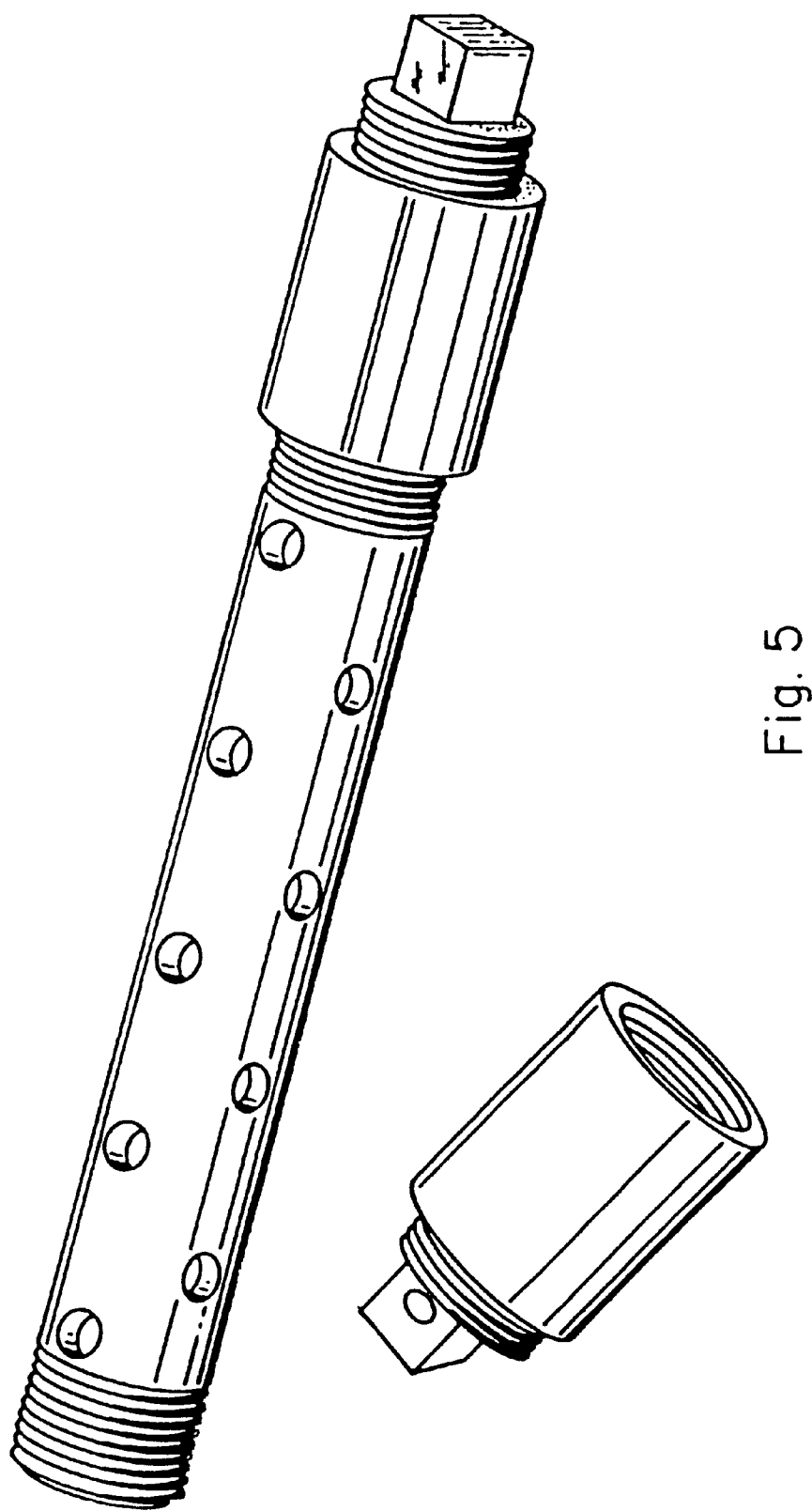
FIG. 5 The type of cylinder used for suspending film strips in wastewater basins. Strips of film 0.5 inch wide and 6 inches long of known weight and thickness were placed in the cylinder which was attached to a steel cable and immersed in a wastewater basin.

Wastewater Treatment Studies: Fifteen numbered cylinders, such as the one shown in FIG. 5, containing one cellulose acetate film each are attached to a steel cable and suspended in Eastman Chemical Company's AD02 basin. Films 1–4 are harvested after 21 days while Films 5–14 are harvested after 27 days. The harvested films are suspended in a neutral detergent solution at 90° C. for 30–60 minutes before washing extensively with water. The films are placed in a vacuum oven at 40° C. until dry before weighing.

| | Cellulose Acetate, DS = 1.7 Biodegradation of Cellulose Acetate (DS = 1.7) | | | | | |
|---|---|---|---|---|---|---|
| Film No. | Original Wt. (mg) | Final Wt. (mg) | % Wt. Loss | Original Thickness | Final Thickness | % Thickness Loss |
| 1 | 223 | 176 | 21 | 6.40 | 5.28 | 18 |
| 2 | 217 | 172 | 21 | 6.33 | 5.59 | 12 |
| 3 | 187 | 150 | 20 | 5.61 | 5.30 | 6 |
| 4 | 249 | 200 | 20 | 5.96 | 5.48 | 8 |
| 5 | 186 | 51 | 73 | 5.56 | 4.08 | 21 |
| 6 | 243 | 75 | 69 | 6.95 | 4.78 | 31 |
| 7 | 220 | 62 | 72 | 6.35 | — | — |
| 8 | 243 | 78 | 68 | 6.29 | 4.55 | 28 |
| 9 | 201 | 19 | 91 | 5.40 | 4.30 | 19 |
| 10 | 146 | 28 | 81 | 5.97 | 4.08 | 32 |
| 11 | 201 | 21 | 90 | 5.79 | 3.83 | 34 |
| 12 | 160 | 44 | 73 | 5.66 | 4.65 | 18 |
| 13 | 197 | 70 | 65 | 6.59 | 4.93 | 25 |
| 14 | 199 | 50 | 75 | 5.71 | 4.92 | 14 |

The films tested after 21 days show a weight loss of 20–21% while the films tested after 27 days show a weight loss of 65–91%. The large loss in film weight and thickness between days 21 and 27 is typical. Generally, an induction period is observed during which microbial attachment is occuring. When the bacteria are attached and enough degradation has occurred to expose more surface area, the rate of degradation increases. Films 2–4 are intact enough so that testing of mechanical properties and comparison to control films (A–C) is possible:

| Film Number | Tangent Modulus ($10^5$ psi) | Tensile Strength ($10^3$ psi) |
|---|---|---|
| 2 | 1.47 | 2.62 |
| 3 | 1.25 | 1.49 |
| 4 | 1.44 | 2.62 |
| A | 2.63 | 4.85 |
| B | 2.91 | 6.04 |
| C | 2.41 | 5.09 |

In each case, substantial loss in the tangent modulus and tensile strength is observed which illustrates how the microbial degradation of the test films leads to loss in film properties.

Compost Biodegradation Assays: Composting can be defined as the microbial catalyzed degradation and conversion of solid organic waste into soil. One of the key characteristics of compost piles is that they are self heating; heat is a natural by-product of the metabolic breakdown of organic matter. Depending upon the size of the pile, or its ability to insulate, the heat can be trapped and cause the internal temperature to rise.

Efficient degradation within compost piles relies upon a natural progression or succession of microbial populations to occur. Initially the microbial population of the compost is dominated by mesophilic species (optimal growth temperatures between 20°–45° C.). The process begins with the proliferation of the indigenous mesophilic microflora and metabolism of the organic matter. This results in the production of large amounts of metabolic heat which raises the internal pile temperatures to approximately 55°–65° C. The higher temperature acts as a selective pressure which favors the growth of thermophilic species on one hand (optimal growth range between 45°–60° C.), while inhibiting the mesophiles on the other. Although the temperature profiles are often cyclic in nature, alternating between mesophilic and thermophilic populations, municipal compost facilities attempt to control their operational temperatures between 55°–60° C. in order to obtain optimal degradation rates. Municipal compost units are also typically aerobic processes, which supply sufficient oxygen for the metabolic needs of the microorganisms permitting accelerated biodegradation rates.

In order to assess the biodegradation potential of the test films, small-scale compost units were employed to simulate the active treatment processes found in a municipal solid waste composter. These bench-scale units displayed the same key features that distinguish the large-scale municipal compost plants. The starting organic waste was formulated to be representative of that found in municipal solid waste streams: a carbon to nitrogen ratio of 25:1, a 55% moisture content, a neutral pH, a source of readily degradable organic carbon (e.g., cellulose, protein, simple carbohydrates, and lipids), and had a particle size that allowed good air flow through the mass. Prior to being placed in a compost unit, all test films were carefully dried and weighed. Test films were mixed with the compost at the start of an experiment and incubated with the compost for 10 to 15 days. The efficiency of the bench scale compost units was determined by monitoring the temperature profiles and dry weight disappearance of the compost. These bench scale units typically reached 60°–65° C. within 8 hours. After 15 days of incubation there was typically a 40% dry weight loss in the compost. Films were harvested after 10 or 15 days of incubation and carefully washed, dried, and weighed to determine weight loss. The following is representative of the results of such composting experiments:

| Film Composition | Weight Loss | Film Thickness (mil) |
|---|---|---|
| Composting Results: 15 Day Composting Trial | | |
| 55/45 CAP (DS = 2.15)/PEG | 36% | 0.63 |
| 55/45 CAP (DS = 2.15)/PTG | 29% | 0.68 |
| 60/40 CAP (DS = 2.7)/PTG + 1% microcrystalline cellulose | 16% | 2.77 |
| 60/40 CAP (DS = 2.7)/PTG | 14% | 2.38 |
| Composting Results: 10 Day Composting Trial | | |
| 45/55 CAP (DS = 2.09)/PEG | 47% | 0.45 |
| 55/45 CAP (DS = 2.15)/PEG | 29% | 0.61 |
| 55/45 CAP (DS = 2.49)/PTG | 26% | 0.56 |
| 60/40 CAP (DS = 2.7)/PTG + 2.5% CaCO3 | 22% | 0.98 |
| 60/40 CAP (DS = 2.7)/PTG + 2% cellulose monoacetate | 20% | 5.31 |
| PTG(T) [60/40] | 17% | 2.95 |
| PTG(T)(D) [60/35/5] | 16% | 19.2 |

Example 18

A 3-mil multilayer blown film was produced from a polybutylene adipate (PBA) copolyester containing 43 mole % terephthalic acid and 100 mole % 1,4-butanediol in combination with a polylactic acid (PLA) polymer from Cargill-Dow identified as 4200D. The coextruded film structure consisted of a core of PLA and skin layers of the PBA aliphatic-aromatic copolyester. The layer ratios of PBA copolyester/PLA/PBA copolyester were about 15/70/15. Similarly good films were produced in layer ratios of about 33/33/33 in a 1.5-mil total film thickness and of 5/90/5 in a 3-mil total film thickness. The coextruded blown film was produced on a laboratory scale blown film line that consisted of two 2 inch extruders and one 2-½ inch extruder. All extruders were 24:1 L:D ratio and a 3:1 compression ratio. A spiral mandrel die with a dual-lip air ring was employed.

The film samples were evaluated for interfacial adhesion strength using a 180 degree T-peel test as described in ASTM procedure D 1876. The test involves initial separation of the layers for mounting in an Instron machine for subsequent separation and evaluation of adhesion strength. Freshly made and after aging three (3) years, the layers could not be de-laminated indicating outstanding adhesion of the PBA copolyester to the PLA, an aliphatic polyester.

The 3-mil films were also evaluated for tensile modulus and strength using ASTM procedure D 882. As indicated in the attached table, the film exhibited good film tensile properties.

| | Coextruded Films of PBA copolyester/PLA/PBA copolyester | |
|---|---|---|
| Property | 5/90/5 freshly made | 15/70/15 after aging |
| Tensile Strength, Mpa | 42 | 11 |
| Elongation, % | 350 | 324 |
| Tangent Modulus, Mpa | 105 | 99 |
| Secant Modulus, Mpa | 70 | 58 |

Example 19
Polyester Containing Adipic Acid—Fibers Spun at 3000 m/m

A multifilament yarn was made from a polybutylene adipate (PBA) copolyesters containing 43 mole % terephthalic acid. The crystallized copolyester pellets (1.15 I.V., 115° C. melting point) were dried 8 hours at 50° C. in a rotary vacuum dryer. The dried pellets were then fed into an extruder and spun into fibers at a melt temperature of 170° C., using a 30-hole spinneret (0.35 mm round orifices) and standard air quench (back to front, 145 cfm, 21° C. air) in the spin cabinet. Take-up speed was 3000 meters/minute. Threadup was directly to the high-speed winder, bypassing the godet rolls. The 150/30 multifilament yarn was not drafted.

This undrafted yarn exhibited elastic properties and a softer but distinctly different hand than expected from polyester. A skein of this yarn developed helical or spiral crimp when exposed 5 minutes at 90° C. in a convection oven.

Example 20
Polyester Containing Adipic Acid—Fibers Spun at 1500 m/m

Polybutylene adipate (PBA) copolyester containing 41 mole % and 46 mole % terephthalic acid were melt spun as follows: The crystallized pellets, having an I.V. of about 1.1–1.25, were dried four hours at 50° C. in a rotary vacuum dryer. The dried pellets were then fed into an extruder and spun into fibers at a melt temperature of 158° C., at an extrusion rate of 29 pounds/hour, using a 154-hole spinneret (shaped, nominal 1.0 mm orifices) and standard air quench (back to front, 145 cfm, 21° C. air) in the spinning cabinet. Take-up speed using godet rolls was 1500 m/m. The fiber cross-section was multi-legged, exhibited a high surface area, and was more ellipical than round in configuration. Depending on the orientation of the cross-section to quench air flow, more or less anisotropy can be introduced. The 9 denier as-spun filaments were single-stage drafted through a 145° C. heated chamber using a 1.5:1 draw ratio, allowed to shrink and develop helical crimp while relaxed on an apron while passing through a 90° C. oven, and then cut into 1.5-inch (38 mm) staple fiber. The helically crimped fiber exhibited good bulk. Some uncrimped short cut [0.25-inch (6 mm) and 0.5-inch (12 mm)] fiber was also produced, but the oven was turned off during this run.

A tow sample was also stuffer-box crimped using no steam, with the crimper roll pressure set at 12 psi. After crimping, fibers were cut to 1.5 inches in length. When blended at 20% by weight with PET staple fibers, the blend produced a satisfactory carded web. Carded webs were also prepared with cotton. Finer binder fibers (less than 6 denier) made to have moderate elasticity are also useful for blending with cellulosics in card-bonded nonwovens, as well as in wood fiber, particle and pressed board composites.

In addition, round cross-section fibers were produced from a similar composition having an I.V. of 0.86 using a 140° C. melt temperature, a radial air quench in spinning, and single-stage drafting through a 135° C. heated chamber with a 1.7:1 draw ratio.

Example 21
Polyester Containing Adipic Acid—Fibers Spun with Optional Quenching Device Crystallized pellets of PBA copolyester containing 43 mole % terephthalic acid (1.2 I.V.) were dried in a rotary vacuum dryer at 40° C. overnight. The dried pellets were melt spun using a spinneret having 332 holes (0.55 mm round orifices) at a melt temperature of 179° C., an extrusion rate of 88 pounds/hour at takeup speeds ranging from 500 to 750 m/m. The spun filaments were quenched using a low air flow and the device described in this invention (see FIGS. 6 and 7), placed 10 inches below the spinneret face. Water was pumped and metered through the slot to rapidly cool the filaments as they come in contact with this quench fluid at the bar. A guide bar about 3 feet below the spinneret positioned the filaments against the fluid at the slot opening of the quenching bar. The multifilament yarn emerging from the spinning cabinet was taken up on a package using godet rolls and a conventional traversing, positive driven winder. With this production spinneret, no fusing of individual filaments was observed.

Example 22
Preparation of Nonwoven Batting

A 6 denier/filament (d/f) unicomponent binder fiber (slightly cold drawn, crimped staple) from the multifilament produced in Example 21 was uniformly blended with 6 d/f PET staple fiber, at 20% by weight of binder fiber. A three ounce/yard$^2$ intimately blended batting was formed using a chute-fed garnett and a crosslapper. The binder fibers in the batting were then activated on-line by passing through an air flow-through oven (two minutes at 140° C.). A strong and resilient bonded fibrous structure resulted.

Binder fibers from compositions of this invention demonstrated radiant infrared, radio frequency and ultrasonic activatability. Similarly beneficial results may be achieved when the binder fiber is a PBT copolyester containing 20 mole % terephthalic acid and 20 mole % 2,6-naphthalenedicarboxylic acid (1.12 I.V.); 25 mole % 1,4-cyclohexanedicarboxylic acid and 15 mole % 1,6-hexanediol (0.93 I.V.); a polybutylene glutarate (PBG) copolyester containing 30 mole % terephthalic acid and 12 mole % 1,6-hexanediol (1.28 I.V.); or a polyhexamethylene glutarate (PHG) copolyester containing 21 mole % terephthalic acid (0.97 I.V.).

Example 23
Seating Products

A 6 d/f unicomponent binder fiber (slightly cold drawn, staple) from the multifilament produced in Example 21 was uniformly blended with 25 d/f PCT [poly (1,4-cyclohexylenedimethylene terephthalate)] polyester staple fiber, at 20% binder fiber by weight. A nonwoven batting was produced and layered into a 15"×15" mold in sufficient amount and under sufficient pressure to obtain a test block density of 2 lbs/ft$^3$. It was then thermally bonded at 140° C. for 30 minutes and cooled prior to removing from the mold. Strong, durable bonds were obtained. The test sample incorporating the elastic properties of the PBA binder fiber exhibited very good recovery from compression and resistance to permanent deformation in simulated seating tests. Samples were tested initially and then after two years. Successfully bonded test samples were also produced when the PCT was replaced with PEN [poly(ethylene naphthalenedicarboxylate)] or PET polyester staple fiber.

Example 24
Sheath/Core Bicomponent Fiber

A 40/60 sheath/core bicomponent fiber was made using polypropylene (18 melt flow rate (MFR) at 230° C.) as the core and a PBA copolyester similar to that described in Example 20 as the sheath. The bicomponent fiber was formed as follows: Polypropylene (PP) pellets were melted in an extruder and fed as the core at a melt temperature of 235° C. For the sheath, dried pellets of the PBA copolyester were melted in a second extruder and fed to the block at a melt temperature of 170° C. The molten streams were coextruded through a spinneret having a sheath/core hole configuration at metering rates adjusted to produce fibers having a 40% copolyester sheath/60% PP core. The tow was drawn on rolls to produce 4 d/f. For staple, the fibers were then stuffer-box crimped and cut into 1.5-inch (38 mm) lengths. In another combination, a PLA based polymer was substituted for PP in the core and fed to the spinneret block at a melt temperature of 240° C.

These bicomponent binder fibers are useful in making nonwovens, laminates and absorbent articles when combined with cellulosics, superabsorbent polymer particles (SAP), polyesters and other matrix fibers, fabrics or films. For some nonwoven structures, these binder fibers can also be used in 100% form. Some of these sheath/core or side-by-side bicomponent polymer combinations may also be biodegradable or compostable.

Example 25
Melt Blown Nonwoven Web

A 24 gram/meter$^2$ (gsm) melt blown web was successfully produced from a PBA copolyester modified with 43 mole % terephthalic acid (0.86 I.V.). The predried copolyester was melt blown at a 220° C. die temperature and a 220° C. air temperature, with an air flow rate of 14 SCFM/inch-die at die-to-collector distances of 6–8 inches. The resultant web performed well as an adhesive layer in lamination tests.

A 30 gsm melt blown web was made having filament sizes in the 4–8 micron range. The web exhibited good color and appearance, elastic properties and a soft hand. Webs from the same composition were also overblown onto polyester and cotton nonwovens.

Similarly good results were obtained with slightly higher I.V. polymer samples (0.95, 1.01, 1.10) of the same composition, as well as 0.95 I.V. samples compounded with a nucleating agent and with a plasticizing agent. With 1.10 I.V., slightly higher 230° C. die and air temperatures were used.

Example 26
Disperse Dyeable Polypropylene Fiber

A polyester fiber was made from a melt containing 95% by weight polypropylene (18 MFR) and 5% PBA copolyester modified with 43 mole % terephthalic acid (1.15 I.V.). The crystallized PBA copolyester pellets were dried at 50° C. overnight in a rotary vacuum dryer and then blended with the PP pellets. The pellet blend was fed into an extruder and spun into fibers at a melt temperature of 235° C., using a 10-hole spinneret (0.8 mm round orifices), a standard air quench (back to front, 145 cfm air flow, 21° C. air) and a take-up speed of 300 m/m. The 19 d/f as-spun fiber was separately single-stage drafted to 17 and 15 d/f. In another spinning experiment, a lower d/f was produced from the 95/5 blend at the same melt temperature, using a 10-hole spinneret (0.35 mm round orifices), same air quench as above, at a take-up speed of 500 m/m. Some of as-spun 5.2 d/f fiber was subsequently drafted to 3.1 d/f. Good results were also observed when the PBA copolyester pellets were not predryed.

Standard PP fibers are not disperse dyeable. However, the PP fibers incorporating the polyesters of this invention were aqueously dyed to a medium shade at 210° F. with Disperse Blue 27. A deeper shade was obtained from fibers similarly made from a 90/10 blend of the same components.

Example 27
In Fabric Helical Crimping and Bulking, Plus Bonding

A 6 d/f unicomponent binder fiber (slightly cold drawn, uncrimped staple) from the multifilament fiber produced in Example 21 was blended with cotton in a Spinlab® fiber opener to form a 80/20 cotton/PBA copolyester fiber blend. The blended open stock was then laid on a non-stick surface and placed in a 95° C. convection oven for five minutes, where shrinkage and bulk development occurred. Then the sample was placed in a 135° C. oven for two minutes, to more fully activate the bonding. This two-step post treatment produced a nonwoven that exhibited good bulk and good recovery from flexing and moderate deformation.

A carded web of the same blend was also needlepunched and the binder fiber was activated in an air flow-through oven, 2 minutes at 140° C. Bulk development was minimal but the machine and cross direction tensile properties significantly increased.

Example 28
Preparation of Air-laid Nonwoven

Air-laid nonwoven samples were prepared from a blend of 20% by weight of uncrimped, short-cut fibers made from a PBA copolyester containing 43 mole % terephthalic acid and 80% by weight fluff pulp (50% hard wood/50% soft wood), using laboratory equipment. Some of these intimately blended webs were activated by carefully placing them on a belt and passing them through an infrared oven followed immediately by a slightly gapped nip. Another set of these webs was bonded on a hot press, with the upper and lower heated plate touching the sample at a very low pressure and a slight gap. The bonding cycle on the press was 1 minute at 120 ° C. plate temperatures. Although there was some linting, the bonded air-laid webs exhibited good structural integrity and handleability, plus much better wet strength and wet bulk retention than normally associated with fluff pulp.

A nonwoven web of 100% fluff pulp was also air-laid on a screen. Adhesive particles of a PBA copolyester containing 43 mole % terephthalic acid were introduced as uniformly as possible onto the layer of fluff pulp to achieve 18% adhesive by weight. The particle or bonding points were activated by carefully passing the sample through an infrared oven and an ungapped low pressure nip. The bonded fluff pulp sample exhibited a significant increase in dry and wet strength.

Example 29
Nonwoven Blends of PLA with PBA Copolyester and Other Binder Fibers Nonwoven fabric battings were formed at weights of 4.5 ounce per square yard using a blend of 75% 6 d/f×1.5 inch PLA fiber and 25% 4 d/f×1.5 inch PBA copolyester binder fiber. Both fibers were unicomponent, round cross-section and crimped; the 1.15 IV PBA contained 43 mol % terephthalic acid and was spun at 1500 m/m. Similar batts were made for comparison by substituting either 3 d/f×1.5 inch fiber from 0.47 IhV PETG copolyester binder fiber or 3 d/f×1.5 inch bicomponent half PET core and half 0.47 IhV PETG copolyester sheath.

The battings were then bonded on a press using top and bottom heated platens and compress-bonded with slight pressure. Bonding occurred at temperatures (°F.) of 250, 275, and 300 for the PBA Copolyester blends and 275 and 300 for the other binder fiber blends. Two inch×ten inch strips were cut in the machine direction of each bonded fabric. Instron test results at a five inch gauge length and 12 inches/min extension rate showed generally equal or better tensile strength and much superior (higher) elongation properties. The higher elongation properties manifest themselves in the more elastic nature of the nonwoven fabric containing the PBA binder fiber versus the other two that exhibit lower elastic stretch and relax properties. The attached table shows the actual results:

Nonwoven Tensile Properties of PBAA Copolyester vs.
Uni- and Bi-component Binder Fibers Blended with PLA Fiber

| Description | 75% PLA 25% PBA Copolyester | | 75% PLA 25% PETG Copolyester | | 75% PLA 25% PET/PETG Copolyester Bico | |
|---|---|---|---|---|---|---|
| Bond Temp. °F. | 250 | 275 | 300 | 275 | 300 | 275 | 300 |
| Break Force, g | 5,115 | 10,228 | 17,619 | 3,370 | 9,451 | 11,269 | 14,905 |
| Elongation, % | 60 | 41 | 51 | 9 | 6 | 22 | 19 |

We claim:

1. A fiber prepared from a copolyester having a dicarboxylic acid component and a diol component, the copolyester comprising repeat units of the following structures:

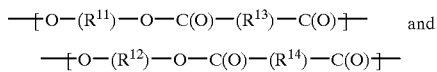 and

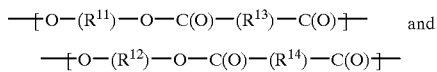

wherein the diol component comprises —O—$R^{11}$—O— and —O—$R^{12}$—O—, where $R^{11}$ and $R^{12}$ are selected from the group consisting of $C_2$–$C_{12}$ alkylene, $C_5$–$C_{10}$ cycloalkylene, $C_2$–$C_{12}$ oxyalkylene and mixtures thereof;

wherein the dicarboxylic acid component contains both aliphatic dicarboxylic acid —O—C(O)—$R^3$—C(O)—, and an aromatic or cycloaliphatic dicarboxylic acid component —O—C(O)—$R^{14}$—C(O)—, wherein $R^{13}$ is selected from the group consisting of $C_0$–$C_8$ alkylene, $C_2$–$C_4$ oxyalkylene and mixtures thereof, wherein the mole % of $R^{13}$ is less than about 95% and is greater than 60% of the dicarboxylic acid component; and $R^{14}$ is selected from the group consisting of $C_6$–$C_{10}$ aryl, $C_5$–$C_{10}$ cycloaliphatic and mixtures thereof wherein the mole % of $R^{14}$ is from greater than about 5% and is less than 40% of the dicarboxylic acid component.

2. The fiber of claim 1, wherein the diol component is selected from the group consisting of 1,4-butanediol, 1,6-hexanediol, 1,3-cyclohexanedimethanol, 1,4-cyclohexanedimethanol, 2,2,4-trimethyl-1,6-hexanediol, 2,2,4,4-tetramethyl-1,3-cyclobutanediol, and mixtures thereof.

3. The fiber of claim 1, wherein the aliphatic dicarboxylic acid component is an acid or ester of glutaric acid, succinic acid, adipic acid or mixtures thereof; and wherein the aromatic or cycloaliphatic dicarboxylic acid component is an acid or ester of terephthalic acid, 1,3-cyclohexanedicarboxylic acid, 1,4-cyclohexanedicarboxylic acid, 2-5-norbornanedicarboxylic acid, 1,3-cyclopentanedicarboxylic acid, 1,5-naphthalenedicarboxylic acid, 2,6-naphthalenedicarboxylic acid or mixtures thereof.

4. The fiber of claim 1, wherein the aromatic or cycloaliphatic dicarboxylic acid is present in a mole % amount ranging from less than 40% to about 25%.

5. The fiber of claim 1, wherein the copolyester is linear, random, semicrystalline and has an inherent viscosity ranging from 0.4 to 1.8 deciliters/gram.

6. The fiber of claim 1, wherein the fiber has a denier ranging from about 30 to about 0.1.

7. A textile or nonwoven article containing at least one fiber of claim 1.

8. A copolyester comprising repeat units of the following structures:

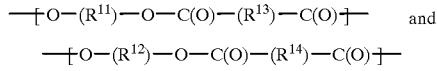 and

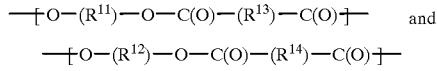

wherein the diol component comprises —O—$R^{11}$—O— and —O—$R^{12}$—O—, where $R^{11}$ and $R^{12}$ are selected from the group consisting of $C_2$–$C_{12}$ alkylene, $C_5$–$C_{10}$ cycloaklene, $C_2$–$C_{12}$ oxyalkylene and mixtures thereof;

wherein the dicarboxylic acid component contains an aliphatic dicarboxylic acid $R^{13}$, and an aromatic or cycloaliphatic dicarboxylic acid component $R^{14}$;

wherein $R^{13}$ is selected from the group consisting of $C_0$–$C_8$ alkylene or $C_2$–$C_4$ oxyalkylene or mixtures thereof, wherein the mole % of $R^{13}$ is less than about 95% and is greater than 60% of the dicarboxylic acid component; and $R^{14}$ is selected from the group consisting of $C_6$–$C_{10}$ aryl, cycloaliphatic and mixtures thereof wherein the mole % of $R^{14}$ is from greater than about 5% and is less than 40% of the dicarboxylic acid component; and wherein the copolyester has a melting point ranging from about 75° C. to about 160° C.

9. The copolyester of claim 8, wherein the aromatic or cycloaliphatic dicarboxylic acid is present in a mole % amount ranging from less than 40% to about 25%.

10. The copolyester of claim 8, wherein the copolyester is linear, random, semicrystalline and has an inherent viscosity ranging from 0.4 to 1.8 deciliters/gram.

11. The copolyester of claim 8, wherein the copolyester is in the form of a powder.

* * * * *